United States Patent
Hirth et al.

(12) 
(10) Patent No.: US 6,331,555 B1
(45) Date of Patent: Dec. 18, 2001

(54) TREATMENT OF PLATELET DERIVED GROWTH FACTOR RELATED DISORDERS SUCH AS CANCERS

(75) Inventors: Klaus P. Hirth, San Francisco; Elaina Mann, Alameda; Laura K. Shawyer, San Francisco, all of CA (US); Axel Ullrich, Munchen (DE); Istvan Szekely, Dunakeszi (HU); Tamas Bajor, Budapest (HU); Janis Haimichael, Budapest (HU); Laszlo Orfi, Budapest (HU); Alex Levitzki; Aviv Gazit, both of Jerusalem (IL); Peng Cho Tang, Moraga, CA (US); Reiner Lammers, Munchen (DE)

(73) Assignees: University of California, Oakland, CA (US); Yissum Research Development Company of the Hebrew University of Jerusalem, Jerusalem (IL); Biosignal LTD, Budapest (HU); Sugen, Inc., Redwood City, CA (US); Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 0 days.

(21) Appl. No.: 09/363,237

(22) Filed: Jul. 27, 1999

Related U.S. Application Data

(63) Continuation of application No. 08/456,957, filed on Jun. 1, 1995, now abandoned.

(51) Int. Cl.$^7$ .......................... A61K 31/42; A61K 31/135; A61K 31/13; A61K 31/415; A61K 31/12
(52) U.S. Cl. ........................... 514/378; 514/649; 514/613; 514/407; 514/394; 514/415; 514/709; 514/711; 514/688; 514/438; 514/371; 514/576
(58) Field of Search .................................. 514/378, 380, 514/649, 613, 407, 314, 415, 709, 711, 688, 438, 371, 576

(56) References Cited

U.S. PATENT DOCUMENTS

| | | |
|---|---|---|
| 4,087,535 | 5/1978 | Heubach et al. . |
| 4,284,786 | 8/1981 | Kämmerer et al. . |
| 4,351,841 | 9/1982 | Kämmerer et al. . |
| 4,992,271 | 2/1991 | Fernandez et al. . |
| 5,217,999 | 6/1993 | Levitzki et al. . |
| 5,268,382 | 12/1993 | Bartlett et al. . |
| 5,314,685 | 5/1994 | Tyle et al. . |
| 5,371,099 | 12/1994 | Bartlett et al. . |
| 5,468,468 | 11/1995 | LaRochelle et al. . |
| 5,494,911 | 2/1996 | Bartlett et al. . |
| 5,514,711 | 5/1996 | Kitano et al. . |
| 5,532,259 | 7/1996 | Bartlett et al. . |
| 5,547,971 | 8/1996 | Weithmann et al. . |
| 5,556,870 | 9/1996 | Weithmann et al. . |
| 5,610,173 | 3/1997 | Schwartz et al. . |
| 5,629,315 | 5/1997 | Blanco et al. . |
| 5,677,335 | 10/1997 | Robertson et al. . |
| 5,700,823 | * 12/1997 | Hirth et al. .......................... 514/380 |
| 5,990,141 | 11/1999 | Hirth et al. . |

FOREIGN PATENT DOCUMENTS

| | | |
|---|---|---|
| 3101093 | 1/1993 | (AU) . |
| 2524929 | 12/1976 | (DE) . |
| 0413329 | 8/1990 | (EP) . |
| 0520722 | 6/1992 | (EP) . |
| 0537742 | 4/1993 | (EP) . |
| 0607775 | 7/1994 | (EP) . |
| 0607776 | 7/1994 | (EP) . |
| 0607777 | 7/1994 | (EP) . |
| 0665013 | 8/1995 | (EP) . |
| 2240104 | 7/1991 | (GB) . |
| 8704436 | 7/1987 | (WO) . |
| 9001800 | 10/1990 | (WO) . |
| 9117748 | 11/1991 | (WO) . |
| 9221641 | 4/1992 | (WO) . |
| 9203736 | 5/1992 | (WO) . |
| 9218481 | 10/1992 | (WO) . |
| 9220642 | 11/1992 | (WO) . |
| 9202444 | 4/1993 | (WO) . |
| 9426260 | 11/1994 | (WO) . |
| 9521613 | 8/1995 | (WO) . |

OTHER PUBLICATIONS

Thoenes et al., "Leflunomide (HWA 486) Inhibits Experimental Autoimmune Tubulointerstitial Nephritis in Rats," *Int. J. Immunopharmacol.* 11:921–929 (1989).

Ueno et al., "Inhibition of PDGT β Receptor Signal Transduction by Coexpression of a Truncated Receptor," *Science* 252:844–252 (1991).

Ulrichs et al., "Suppression of Natural Xenophile Antibodies With the Novel Immunomodulating Drug Leflunomide," *Transplant Proc.* 24:718–719 (1992).

Wada et al., "Anti–receptor antibodies reverse the phenotype of cells transformed by two interacting proto–oncogene encoded receptor proteins," *Oncogene* 5:489–495 (1990).

(List continued on next page.)

*Primary Examiner*—Theodore J. Criares
(74) *Attorney, Agent, or Firm*—Foley & Lardner

(57) ABSTRACT

The present invention concerns compounds which can inhibit platelet derived growth factor receptor (PDGF-R) activity, preferably such compounds also inhibit the activity other members of the PDGF-R super family and are selective for members of the PDGF-R super family. The PDGF-R super family includes PDGF-R and PDGF-R related kinases Flt, and KDR. The featured compounds are active on cell cultures to reduce the activity of the PDGF-R and preferably one or more PDGF-R related kinases. An example of a featured compound, A10 (see FIG. 1a), and its ability to inhibit growth of tumor cells in vivo is described below. Using the present application as guide other compounds able to inhibit PDGF-R and preferably Flt and/or KDR can be obtained. Such compounds are preferably used to treat patients suffering from cell proliferative disorders characterized by inappropriate PDGF-R activity.

15 Claims, 35 Drawing Sheets

OTHER PUBLICATIONS

Waltenberger et al., "Different Signal Transduction Properties of KDR and Flt1, Two Receptors for Vascular Endothelial Growth Factor," *J. Biol. Chem.* 269:26988–26995 (1994).

Warri et al., "Estrogen Suppression of erbB2 Expression is Associated with Increased Growth Rate of ZR–75–I Human Breast Cancer Cells In Vitro and in Nude Mice," *Int. J. Cancer* 49:616–623 (1991).

Weithmann et al., "Effect of leflunomide on constitutive and inducible pathways of cellular eiconsanoid generation," *Agents Actions* 41:164–170 (1994).

Williams et al., "Immunosuppressive Effects of Leflunomide in a Cardiac Allograft Model," *Transplantation Proc.* 25:745–746 (1993).

Williams et al., "Leflunomide in Experimental Transplantation," *Transplantation* 57:1223–1231 (1994).

Xiao et al., "Effect of Leflunomide in Control of Acute Rejection in Hamster–to–Rat Cardiac Xenografts," *Transplantation Proceedings* 26:1263–1265 (1994).

Xiao et al., "Leflunomide Controls Rejection in Hamster of Rat Cardiac Xenografts," *Transplantation* 58:828–834 (1994).

Yaish et al., "Blocking of EGF–Dependent Cell Proliferation by EGF Receptor Kinase Inhibitors," *Science* 242:933–935 (1988).

Yoneda et al., "The Antiproliferative Effects of Tyrosine Kinase Inhibitors Tyrphostins on a Human Squamous Cell Carcinoma in Vitro and in Nude Mice," *Cancer Research* 51:4430–4435 (1991).

Zeillinger et al., "EGF–R and Steroid Receptors in Breast Cancer: A Comparison with Tumor Grading, Tumor Size, Lymph Node Involvement, and Agen," *Clin. Biochem.* 26:221–227 (1993); Andrews et al. (American Veterinary Medicine Association Panel on Euthanasia), "1993 Report of the AVMA Panel on Euthanasia," *J. American Veterinary Medicine Association* 202(2):229–249 (1993).

Zielinski et al., "Effects of leflunomide (HWA 486) on expression of lymphocyte activation markers," *Agents Actions* 38:(Special Conference Issue) C80–C82 (1993).

Walia et al., "Ethanol Inhibition of Cell–Mediated Lysis of Antibody–Sensitized Target Cells at a Calcium–Dependent Step," *Society for Experimental Biology and Medicine,* vol. 2, No. 2 (1989) pp. 177–181, Williams & Wilkins.

Hansen et al., "Re–examination and further development of a precise and rapid dye method for measuring cell growth/cell kill," *Journal of Immunological Methods* 119 (1989) pp. 203–210, Elsevier.

Bartlett et al., *Agents and Actions,* 32:10–21 (1991).

DeVita et al., "Section 22.4. Monoclonal Antibodies for Immunodiagnosis and Immunotherapy of Epithelial Ovarian Cancer," in *Biological Therapy of Cancer,* pp. 550–563, J. B. Lippincott Company (1990).

Gazit et al., *J. Med. Chem.,* 36:3336–3564 (1993).

Gottardis et al., *J. Steroid Biochem.* 30:311–314 (1988).

Ueno et al., *Science,* 252:844–848 (1991).

Zeillinger et al., *Clin. Biochem.* 26:221–227 (1993).

Ueno et al., "Inhibition of PDGF β Receptor Signal Transduction by Coexpression of a Truncated Receptor," *Science* 252:844–252 (1991).

Yoneda et al., "The Antiproliferative Effects of Tyrosine Kinase Inhibitors Tyrphostins on a Human Squamous Cell Carcinoma in Vitro and in Nude Mice," *Cancer Research* 51:4430–4435 (1991).

Bristol Laboratories Oncology Products, "VePesid (Etoposide) for Injection and Capsules," Dec. 1992.

Kaur, "Tyrphostin induced growth inhibition: correlation with effect on $p210^{bcr-abl}$ autokinase activity in K562 chronic myelogenous leukemia," *Anti–Cancer Drugs* 5:213–222 (1994).

Kovalenko et al., "Selective Platelet–derived Growth Factor Receptor Kinase Blockers Reverse sis–Transformation," *Cancer Research* 54:6106–6114 (1994).

Mattar et al., "Effects of leflunomides active metabolite, A771726, on signal transduction pathways necessary for proliferation," *Immunobiology* 186(1–2):43 (1992) (abstract).

Andrews et al. (American Veterinary Medicine Association Panel on Euthanasia), "1993 Report of the AVMA Panel on Authanasia," *J. American Veterinary Medicine Association* 202(2):229–249 (1993).

Bartlett et al., "Leflunomide (HWA 486), a novel immunomodulating compound for the treatment of autoimmune disorders and reactions leading to transplantation rejection," *Agents and Actions* 32:10–21 (1991).

Bartlett et al., "Effects of leflunomide on immune responses and models of inflammation," *Springer Semin. Immunopathol.* 14:381–394 (1993).

Bartlett et al., "Leflunomide: A novel immunomodulating drug" in *Nonsteroidal Anti–Inflammatory Drugs* $2^{nd}$ ed. pp. 349–366, Lewis Furstk eds., Dekker, NY NY (1990).

Baselga et al., "Antitumor Effects of Doxorubicin in Combination With Anti–epidermal Growth Factor Receptor Monoclonal Antibodies," *J. of Natl. Cancer Institute* 85(16):1327–1333 (1993).

Baudy et al., "Potent Quinoxaline–Spaced Phosphono α–Amino Acids of the AP–6 Type as Competitive NMDA Antagonists: Synthesis and Biological Evaluation," *J. Med. Chem.* 36:331–342 (1993).

Bilder et al., "Tyrphostins inhibit PDGF–induced DNA synthesis and associated early events in smooth muscle cells," *Am. J. Physiol.* 260 (Cell Physiol.29):C721–C730 (1991).

Birchall et al., "Compositions for killing internal parasites containing 3–teri–alkyl–4–hydroxy–5–halobenzylidene–malononitriles," *Chemical Abstracts* 88:535 (1978).

Bryckaert et al., "Inhibition of Platelet–Derived Growth Factor–Induced Mitogenesis and Tyrosine Kinase Activity in Cultured Bone Marrow Fibroblasts by Tyrphostins," *Exp. Cell Research* 199:255–261 (1992).

Bustelo and Barbacid, "Tyrosine Phosphorylation of the vav Proto–Incogene Product in Activated B Cells," *Science* 256:1196–1199 (1992).

Caraglia et al., "Cytosine arabinoside increases the binding of $^{125}$I–labeled epidermal growth factor and $^{125}$I–transferrin and enhances the in vitro targeting of human tumor cells with anti–(growth factor receptor)mAb," *Cancer Immunol. Immunother.* 37:150–156 (1993).

Carboni et al., "Cyanocarbon Chemistry, XI. Malononitrile Dimer," *J. Am. Chem. Soc.* 80:2838–2840 (1958).

*Cecil Textbook of Medicine,* eds. Wyngaarden, Smith, Bennett, W.B. Saunders (1992) p. 2220.

Chen and Okayama, "Calcium Phosphate–Mediated Gene Transfer: A Highly Efficient Transfection System for Stably Transforming Cells with Plasmid DNA," *BioTech.* 6:632–638 (1988).

Cherwinski et al., "The Immunosuppressant Leflunomide Inhibits Lymphocyte Progression Through Cell Cycle by a Novel Mechanism," *J. Pharmacology and Exp. Therap.* 272:460–468 (1995).

Chong et al., "Leflunomide, a Novel Immunosuppressive Agent," *Transplantation* 55:1361–1366 (1993).

Chong et al., "Leflunomide, a Novel Immunomodulatory agent: In Vitro Analyses of the Mechanism of Immunosuppression," *Transplant Proc.* 25:747–749 (1993).

Conn et al., "Purification of a glycoprotein vascular endothelial cell mitogen from a rat glimo–derived cell line," *Proc. Natl. Acad. Sci. USA* 87:1323–1327 (1990).

Dati et al., "Inhibition of a c–erbB–2 oncogene expression by estrogens in human breast cancer cells," *Oncogene* 5:1001–1006 (1990).

Decker and Lohmann–Matthes, "A quick and simple method for the quantitation of lactate dehydrogenase release in measurements of cellular cytotoxicity and tumor necrosis factor (TNF) activity," *J. Immunol. Methods* 115:61–69 (1988).

Ehrlich and Bogert, "Experiments in the Veratrole and Quinoxaline Groups," *J. Org. Chem.* 12:522–534 (1947).

Ferris et al., "Synthesis of Zuinazoline Nucleosides from Ribose and Anthranilonitrile, Application of Phase–Transfer Catalysis in Nucleoside Synthesis," *J. Org. Chem.* 44(2):173–178 (1979).

Floege et al., actors involved in the regulation of mesangial cell proliferation in vitro and in vivo, *Kidney International* 43S:47–54 (1993).

Fry et al., "New insights into protein–tyrosine kinase receptor signaling complexes," *Protein Science* 2:1785–1797 (1993).

Gazit et al., "Tyrphostins. 1. Synthesis and Biological Activity of Protein Tyrosine Kinase Inhibitors," *J. Med. Chem.* 32:2344–2352 (1989).

Gazit et al., "Tyrphostins. 2. Heterocyclic and α–Substituted Benzylidenemalononitrile Tyrphostins as Potent Inhibitors of EGF Receptor and ErbB2/neu Tyrosine Kinases," *J. Med. Chem.* 34:1896–1907 (1991).

Gazit et al., "Tyrophostins. 3. Structure–Activity Relationship Studies of α–Substituted Benzylidenemalononitrile 5–S–Aryltyrphostins" *J. Med. Chem.* 36:3556–3564 (1993).

Giant et al., "Immunomodulation of proteoglycan–induced progressive polyarthritis by leflunomide," *Immunopharmacology* 23:105–116 (1992).

Gottardis et al., "Estradiol–Stimulated Growth of MCF–7 Tumors Implanted in Athymic Mice: A model to Study the tumoristatic Action of Tamoxifen," *J. Steroid Biochem.* 30(1–6):331–314 (1988).

Gulbins et al., "Tyrosine Kinase–Stimulated Guanine Nucleotide Exchange Activity of Vav in T Cell Activation," *Science* 260:822–825 (1993).

Hale et al., "Prognostic value of epidermal growth factor receptor expression in cervical carcinoma," *J. Clin. Pathol.* 46:149–153 (1993).

Harris et al., "Breast Cancer (First of Three Parts), " *New England J. of Medicine* 327(5):319–328 (1992).

Heldin, "Structural and functional studies on platelet–derived growth factor," *EMBO Journal* 11:4251–4259 (1992).

Hoekstra et al., "Differential effects of steurosporine and tyrphostins on receptor tyrosine kinase autophosphorylation and peptide substrate phosphorylation," *Experimental Therapeutics* from 84th Annual Meeting of American Association for Cancer Research, vol. 34, #2455 (1993).

Honegger et al., "Point Mutation at the ATP Binding Site of EGF Receptor Abolishes Protein–Tyrosine Kinase Activity and Alters Cellular Routing," *Cell* 5:199–209 (1987).

Houck et al., "The Vascular Endothelial Growth Factor Family: Identification of a Fourth Molecular Species and Characterization of Alternative Splicing of RNA," *Molecular Endocrinology* 5:1806–1814 (1991).

Issidorides and Haddadin, "Benzofurazan Oxide. II. Reactions with Enolate Anions," *J. Org. Chem.* 31:4067–4068 (1966).

Ju et al., "Leflunomide inhibits cytokine–induced DNA synthesis of rabbit synovial cells in culture," *Acute Pharmacological Sinica* 15:223–226 (1994).

Ju et al., "Leflunomide inhibits PAF induced DNA synthesis in rabbit synovial cells and PAF production from rat peritomeal macrophages," *Acta Pharmacological Sinica* 92:90–94 (1994).

Karameris et al., "Expression of Epidermal Growth Factor (EGF) and Epidermal Growth Factor Receptor (EGFR) in Gastric and Colorectal Carcinomas, An Immunohistological Study of 63 Cases," *Path Res. Pract.* 189:133–137 (1993).

Koenders et al., "Epidermal growth factor receptor and prognosis in human breast cancer: a prospective study," *Breast Cancer Research and Treatment* 25:21–27 (1993).

Korzeniewski and Callawaert, An Enzyme–Release Assay for Natural Cytotoxicity[1], *J. Immunol. Methods* 64:33 (1983).

Kuechle et al., "Prevention of Kidney and Skin Graft Rejection in Rats by Leflunomide, a New Immunomodulating Agent," *Transplant Proc.* 23:1083–1806 (1991).

Lee and Salemnick, "Purine N–Oxides, LXII. 2,4–Dioxyopyrido[2,3,–d]pyrimidine N–Oxides," *J. Org. Chem.* 40(24):3608–3610 (1975).

Levitzki, "Tyrphostins—Potential Antiproliferative Agents and Novel Molecular Tools," *Biochem. Pharm.* 40(5):913–918 (1990).

Ley and Seng, "Synthesen unter Verwendung von Benzofuroxan," *Synthesis* 1975:415–422 (1975).

Lyall et al., "Tyrphostins Inhibit Epidermal Growth Factor (EGF)–Receptor Tyrosine Kinase Activity in Living Cells and EGF–stimulated Cell Proliferation," *J. Bio. Chem.,* 264:14503–14509 (1989).

Marshall, E., "Search for a Killer: Focus Shifts from Fat to Hormones," *Science* 259:618–621 (1993).

Mattar et al., "Inhibition of the epidermal growth factor receptor tyrosine kinase activity by leflunomide," *FEBS Letters* vol. 334:161–164 (1993) [19].

McChesney et al., "An Evaluation of Leflunomide in the Canine Renal Transplantation Model," *Transplantation* 57:1717–1722 (1994).

Millauer et al., "High Affinity VEGF Binding and Developmental Expression Suggest Flk–1 as a Major Regulator of Vasculogenesis and Angiogenesis," *Cell* 72:835–846 (1993).

Mosmann, "Rapid Colorimetric Assay for Cellular Growth and Survival Application to Proliferation and Cytotoxicity Assays," *J. Immunol. Methods* 65:55–63 (1983).

Muller et al., "BCR First Exon Sequences Specifically Activate the BCR/ABL Tyrosine Kinase Oncogene of Philadelphia Chromosome–Positive Human Leukemias," *Mol. Cell. Biol.* 11:1785–1782 (1991).

Nichterlein et al., "Leflunomide (HWA 486) Prolongs Course of Murine Listeriosis," *Immunol. Infect. Dis.* 4:18–22 (1949).

Ogawa et al., "Therapeutic Effects of Leflunomide, a New Antirheumatic Drug, on Glomerulonephritis Induced by the Antibasement Membrane Antibody in Rats," *Clin. Immunol. Immunopath.* 61:103–118 (1991).

Ogawa et al., "Effects of leflunomide on glomerulonephritis induced by antibasement membrane antibody in rats," *Agents Actions* 31:321–328 (1990).

Ohmichi et al., The Tyrosine Kinase Inhibitor Tyrphostin Blocks The Cellular Actions of Nerve Growth Factor, *Biochemistry* 32:4650–4658 (1993).

Osborne et al., "Effect of Estrogens and Antiestrogens on Growth of Human Breast Cancer Cells in Athymic Nude Mice," *Cancer Research* 45:584–590 (1985).

Osherov et al., "Selective Inhibition of the EGF and Neu receptors by Tyrophostins," *J. Cell Biochem.* S17A:237 (1993).

Osherov et al., "Selective Inhibition of the Epidermal Growth Factor and HER2/Neu Receptors by Tyrphostins," *J. Bio. Chem.* 268:11134–11142 (1993).

Ozzello and Sordat, "Behavior of Tumors Produced by Transplantation of Human Mammary cell Lines in Athymic Nude Mice," *Eur. J. Cancer* 16:553–559 (1980).

Patterson et al., "3–Carboxy–5–methyl–N–[4–trifluoromethyl)phenyl]–4–isoxazolecarboxamide, a New Prodrug for the Antiarthritic Agent 2–Cyano–3–hydroxy–N[4–trifluoromethyl)phenyl]–2–butenamide," *J. Med. Chem.* 35:507–510 (1992).

Peterson and Barnes, "Genistein and Biochanin A Inhibit the Growth of Human Prostate Cancer Cells but not Epidermal Growth Factor Receptor Tyrosine Autophosphorylation," *The Prostate* 22:335–345 (1993).

Pigott et al., "Expression of epidermal growth factor receptor in human glioblastoma multiforme," *Brit J. of Neurosurgery* &;261–265 (1993).

Plate et al., "Vascular endothelial growth factor is a potential tumour angiogenesis factor in human gliomas in vivo," *Nature* 359:845–848 (1992).

Plate et al., "Up–Regulation of Vascular Endotheial Growth Factor and Its Cognate Receptors in a Rat Glimoa Model of Tumor Angiogenesis," *Cancer Research* 53:5822–5827 (1993).

Plate et al., "Platelet–Derived Receptor–$\beta$ is Induced during Tumor Development and Upregulated during Tumor Progression in Endothelial Cells in Human Gliomas," *Laboratory Investigation* 4:529–534 (1992).

Pollack et al., "Response of malignant glioma cell lines to epidermal growth factor and platelet–derived growth factor in a serum–free medium," *J. Neurosurg.* 73:106–112 (1990).

Ren et al., "Identification of a Ten–Amino Acid Proline–Rich SH3 Binding Site," *Science* 259:1157–1161 (1993).

Rendu et al., "Inhibition of Platelet Activation by Tyrosine Kinase Inhibitors," *Biochem. Pharm.* 44(5):881–888 (1992).

Rosenthal et al., "Conditioned Medium from Mouse Sarcoma 180 Cells Contains Vascular Endothelial Growth Factor," *Growth Factors* 4:53–59 (1990).

Ross, "The pathogenesis of atherosclerosis: a perspective for the 1990s," *Nature* 362:801–809 (1993).

Rusch et al., "Differential Expression of the Epidermal Growth Factor Receptor and Its Lgands in Primary Non–Small Cell Lung Cancers and Adjacent Benign Lung," *Cancer Research* 53:2379–2385 (1993).

Rygaard and Povlsen, "Heterotransplantation of a Human Malignant Tumour to 'Nude' Mice," *Acta path. microbiol. scand.* 77:758–760 (1969).

Schorlemmer et al., "Prolongation of Allogeneic Transplanted Skin Grafts and Induction of Tolerance by Leflunomide, a New Immunosuppressive Isoxazol Derivative," *Transplant. Proc.* 25:763–767 (1993).

Schornagel et al., "Synthesis and Evaluation of 2,4–Diaminoquinazoline Antifolates with Activity Against Methotrexate–Resistant Human Tumor Cells," *Biochem. Pharm.* 33(20):3251–3255 (1984).

Scott et al., "p185$^{HER2}$ Signal Transduction in Breast Cancer Cells," *J. Bio. Chem.* 266(22):14300–14305 (1991).

Seibert et al., "Clonal Variation of MCF–7 Breast Cancer Cells in Vitro and in Athymic Nude Mice," *Cancer Research* 43:2223–2239 (1983).

Shafie and Grantham, "Role of Hormones in Growth and Regression of Human Breast Cancer Cells (MCF–7) Transplanted into Athymic Nude Mice," *J. Natl Cancer Institute* 76(1):51–56 (1981).

Shweiki et al., "Vascular endothelial growth factor induced by hypoxia may mediate hypoxia–initiated angiogenesis," *Nature* 359:843–845 (1992).

Skehan et al., "New Colorimetric Cytotoxicity Assay for Anticancer–Drug Screening," *J. Natl. Cancer Inst.* 82:1107–1112 (1990).

Talmadge and Twardzik, "Role of Cytokines in Inflammation and Autoimmunity," *Agents and Actions* 35S:135–141 (1991).

\* cited by examiner

FIG. 1a-1
GROUP 1
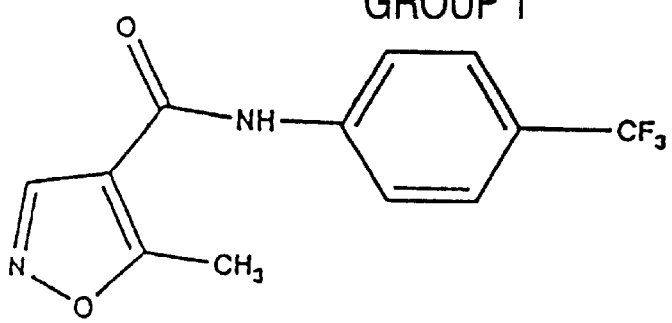
A10
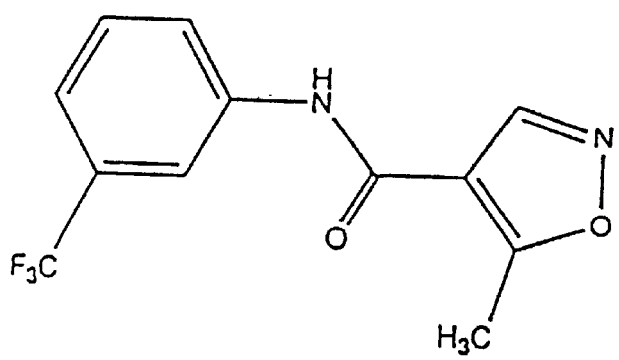
A11
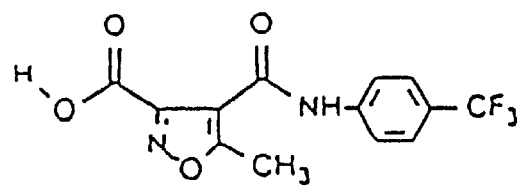
A12

GROUP 2

A13

FIG. 1b-1
GROUP 2
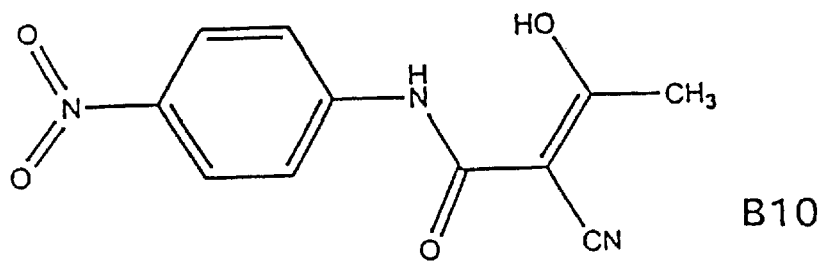
B10
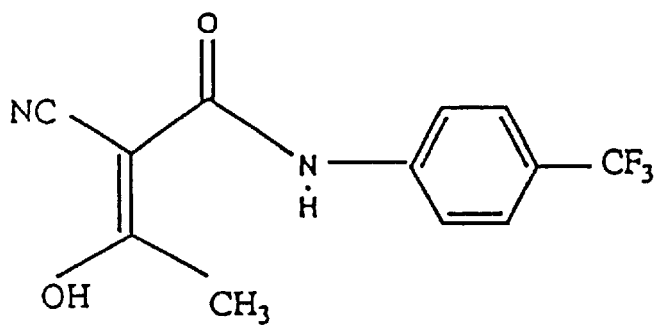
B11
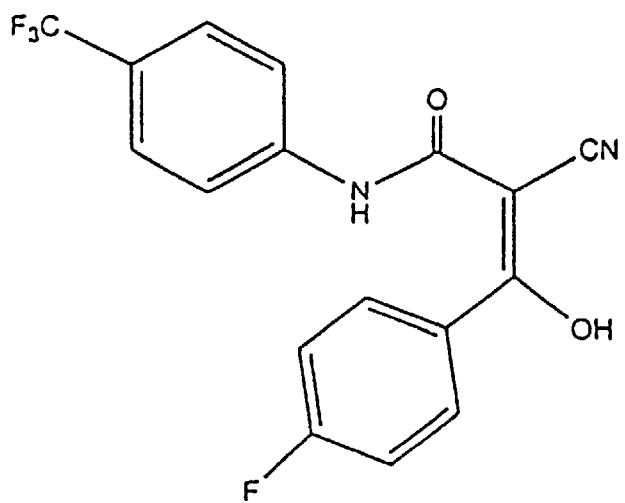
B12

FIG. 1b-2
GROUP 2
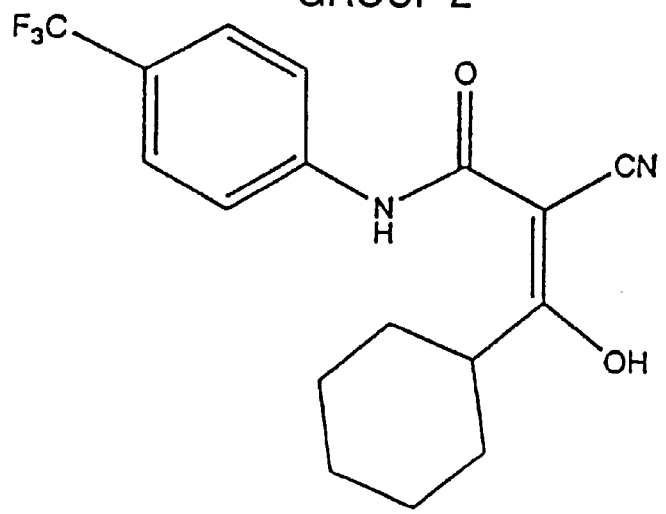
B13
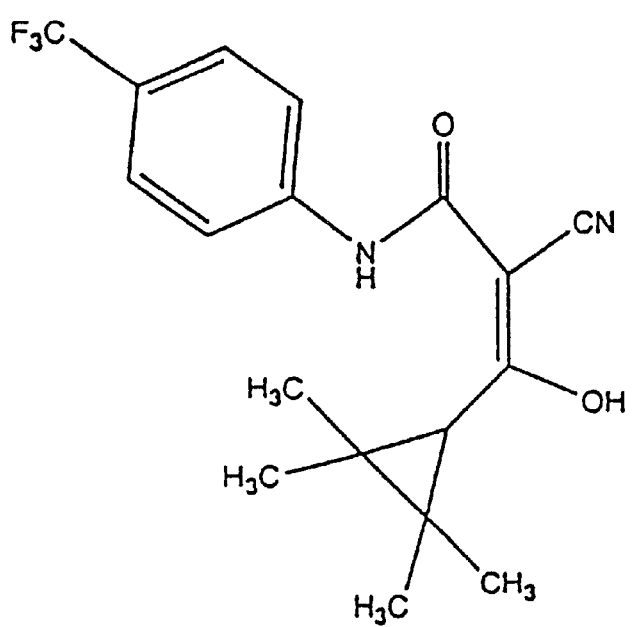
B14

FIG. 1b-3
GROUP 2
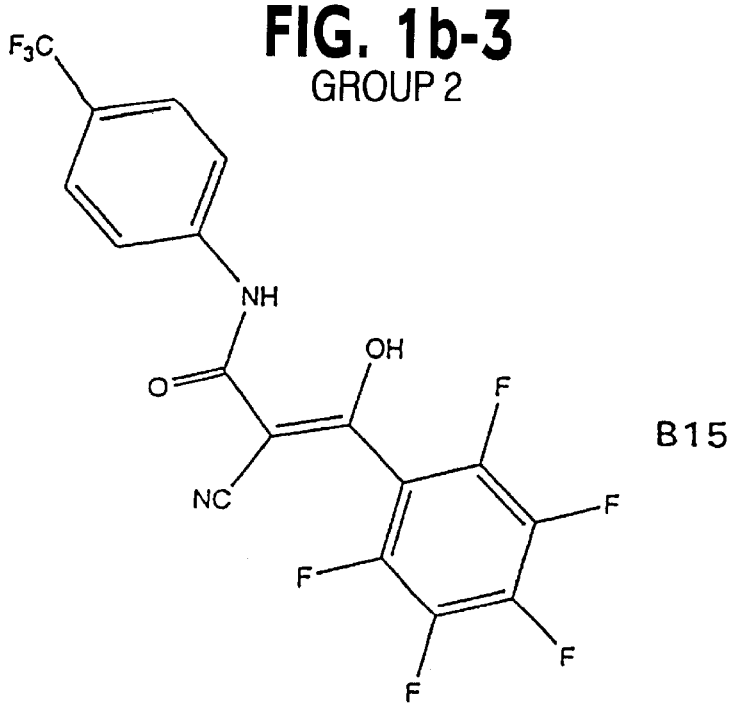
B15
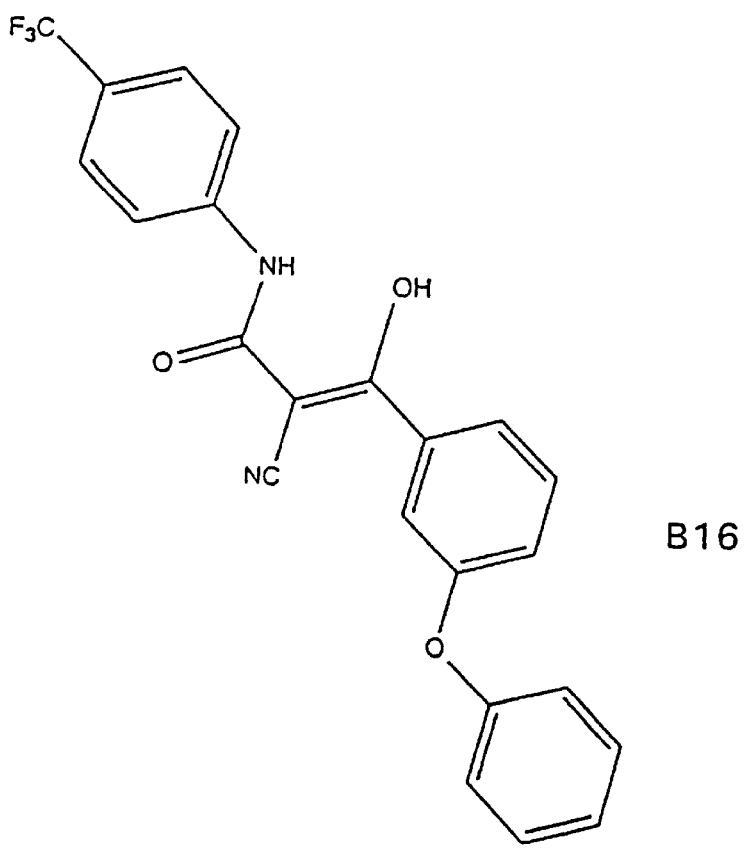
B16

FIG. 1b-4
GROUP 2
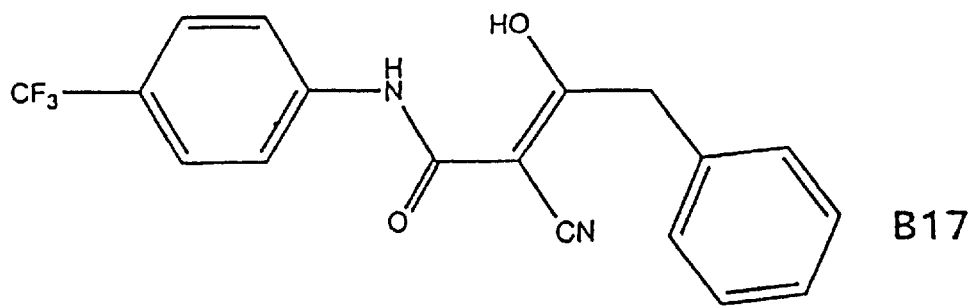
B17
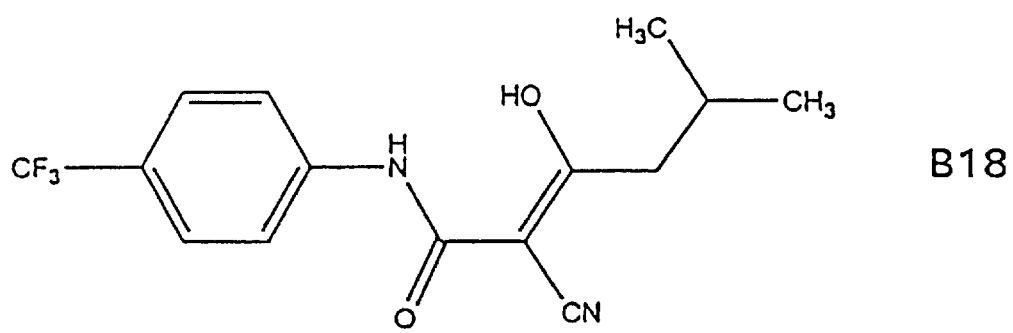
B18
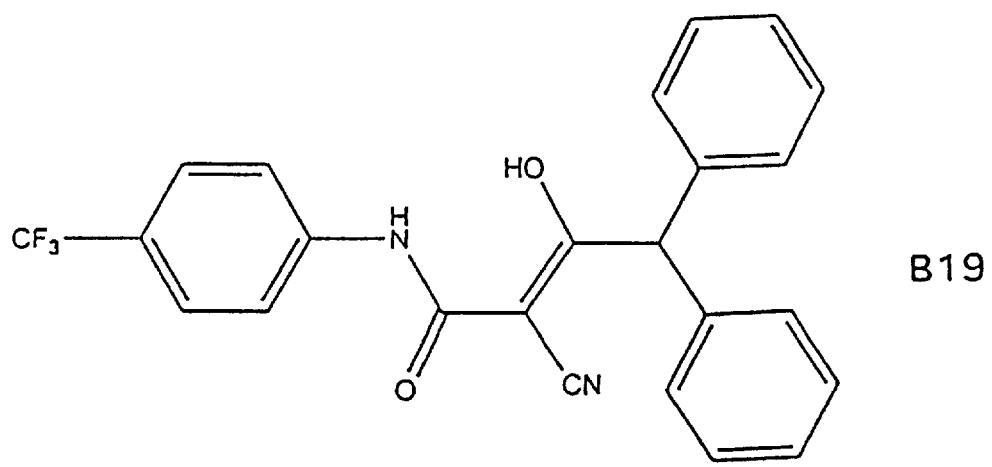
B19

GROUP 3

C10

C11

GROUP 3

C13

FIG. 1d-1
GROUP 4
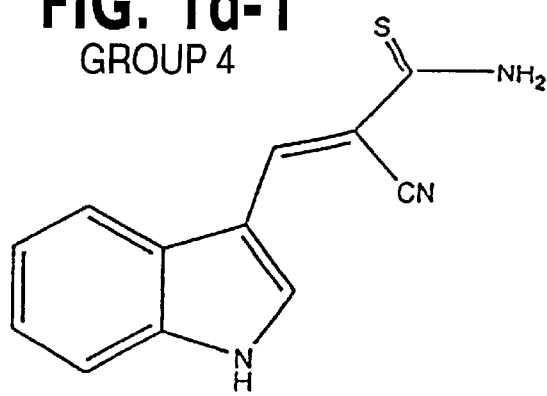
D11
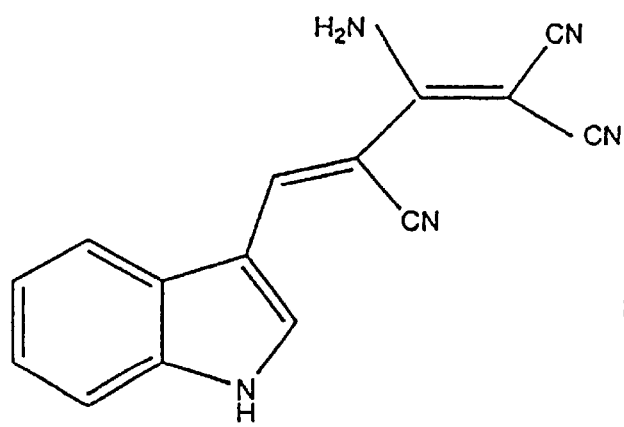
D12
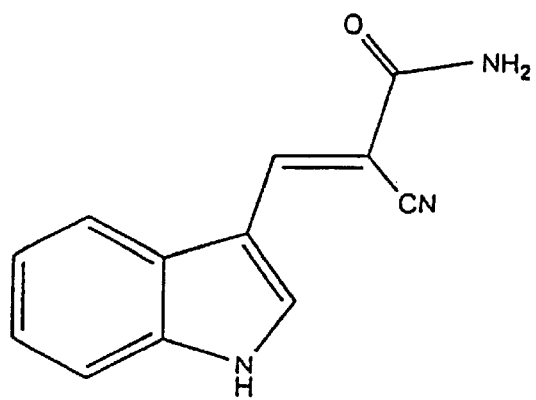
D13

FIG. 1d-2
GROUP 4
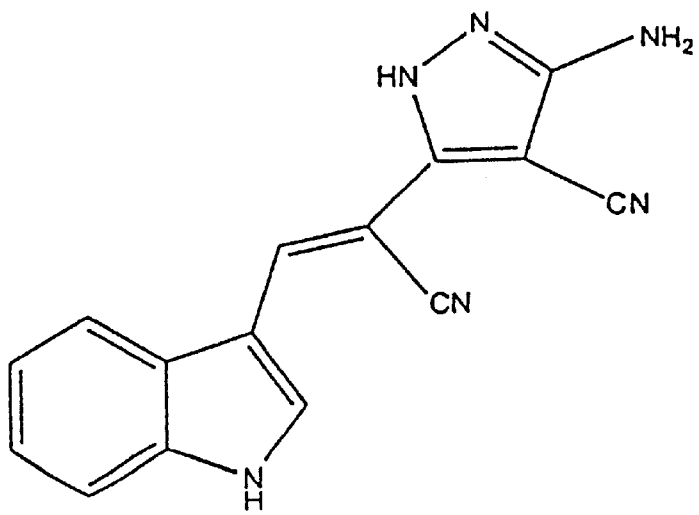
D14
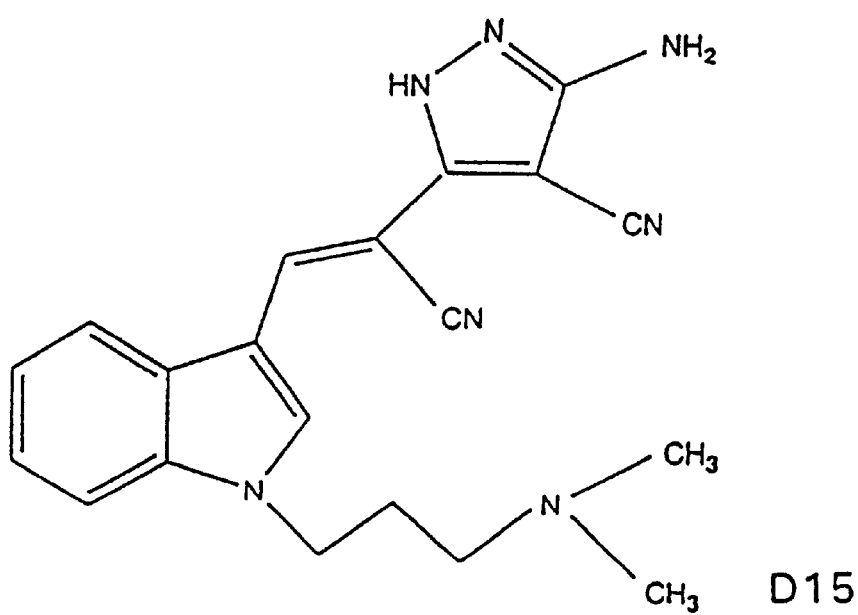
D15

FIG. 1d-3
GROUP 4
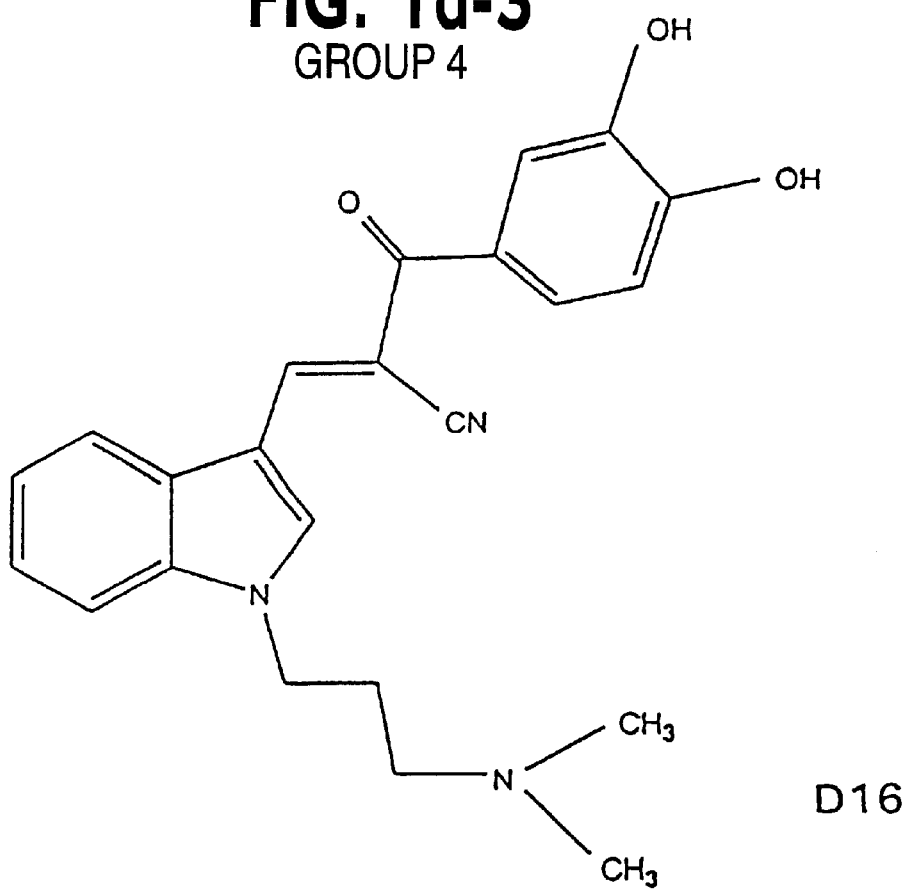
D16
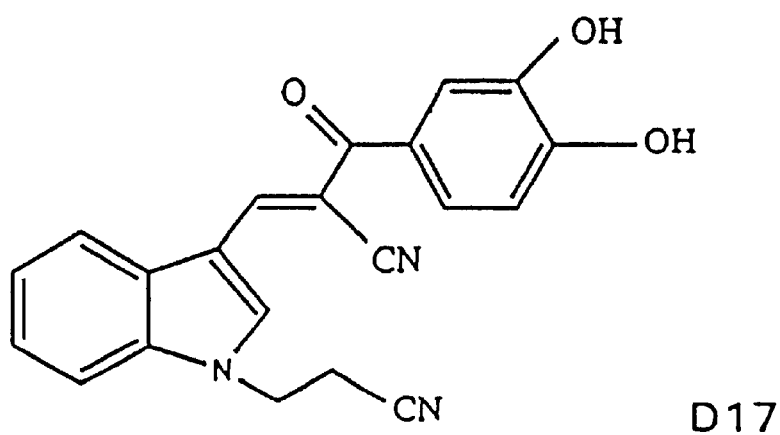
D17

FIG. 1d-4
GROUP 4
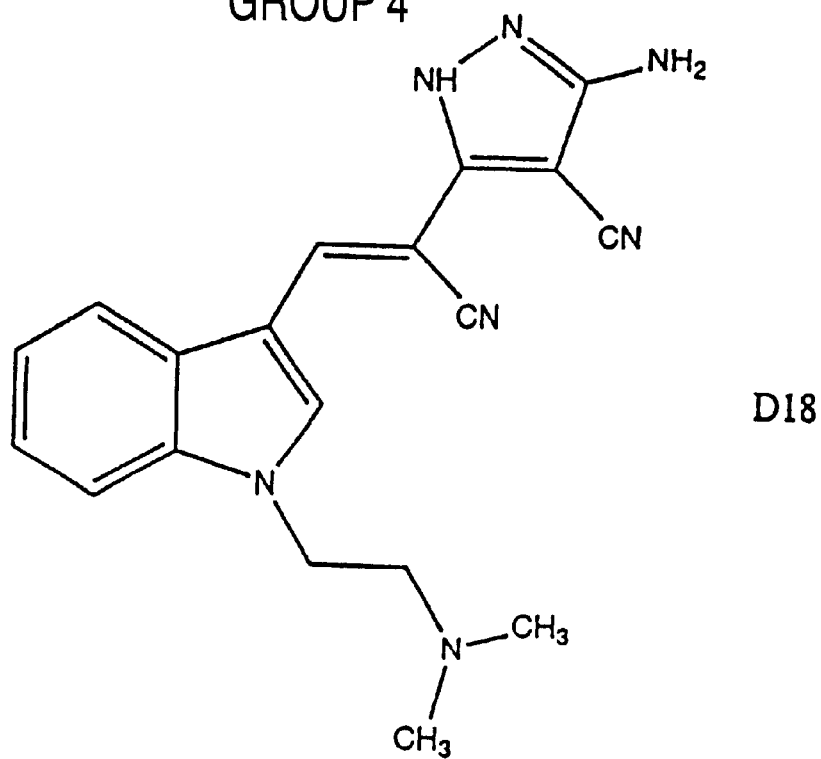
D18
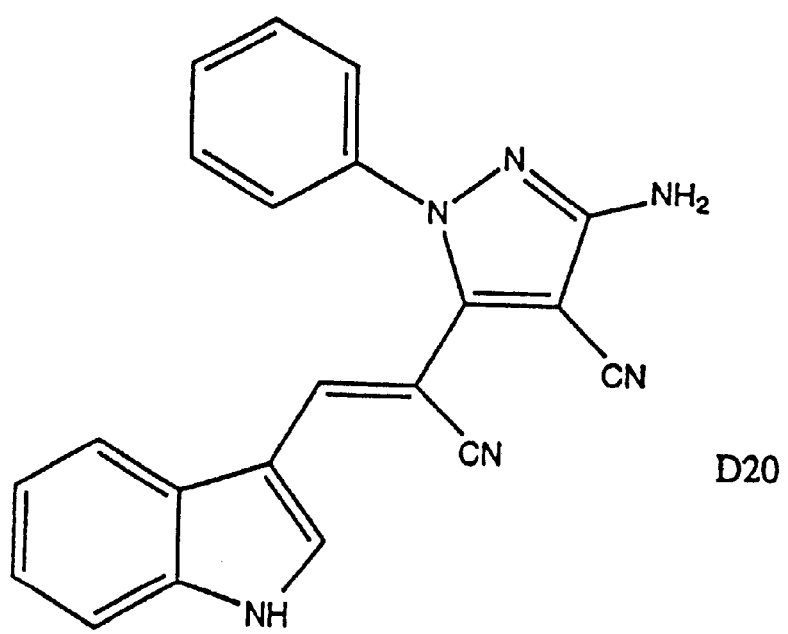
D20

GROUP 5

E10

E11

GROUP 5

E12

E13

E14

FIG. 1e-3
GROUP 5
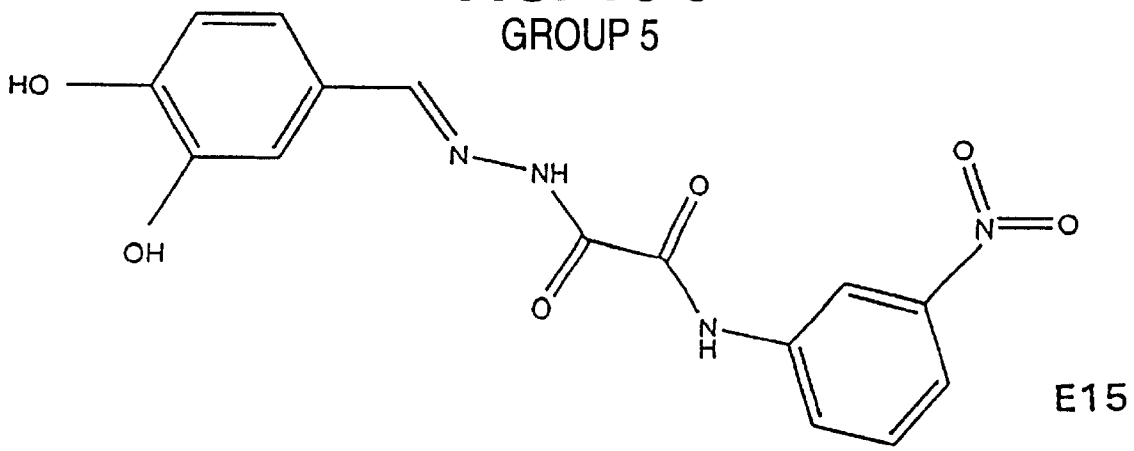
E15
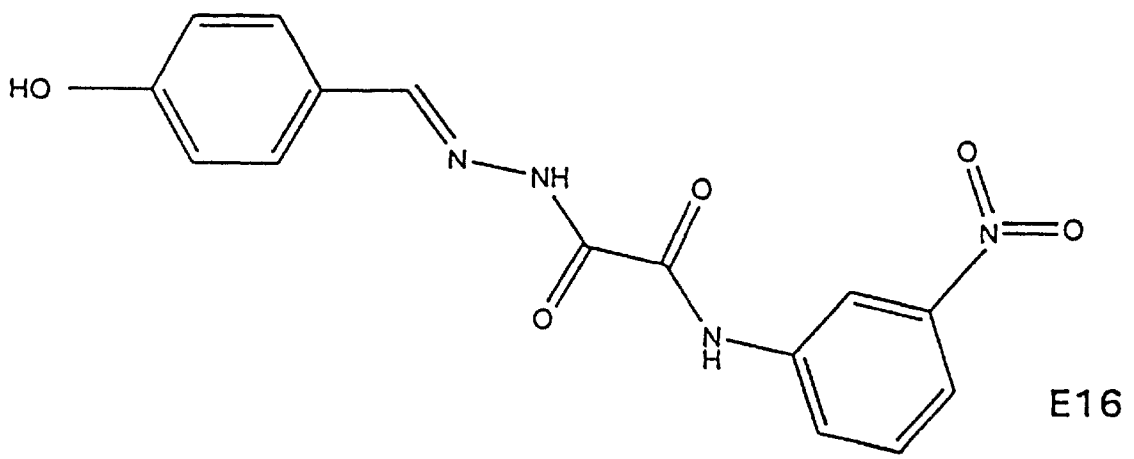
E16

GROUP 6

F10

F11

F12

FIG. 1g-1
GROUP 7
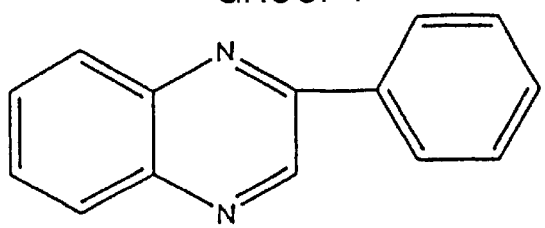 G10
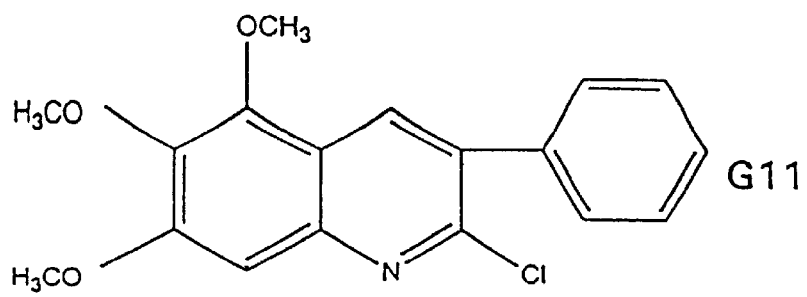 G11
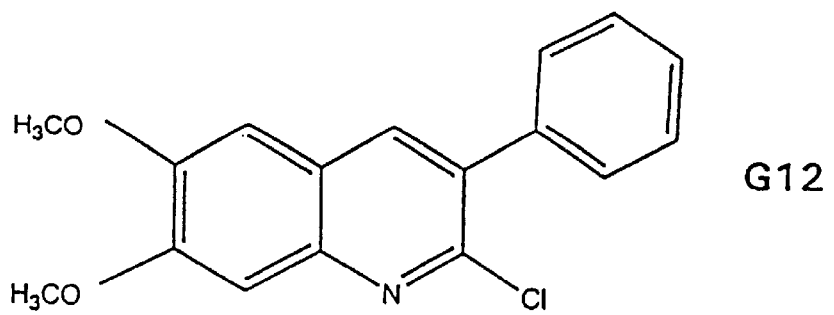 G12
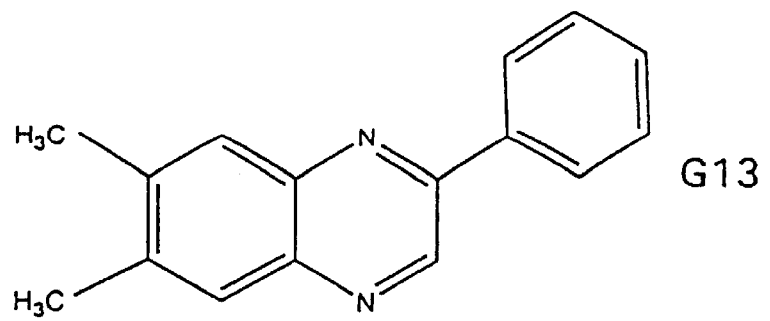 G13

FIG. 1g-2
GROUP 7
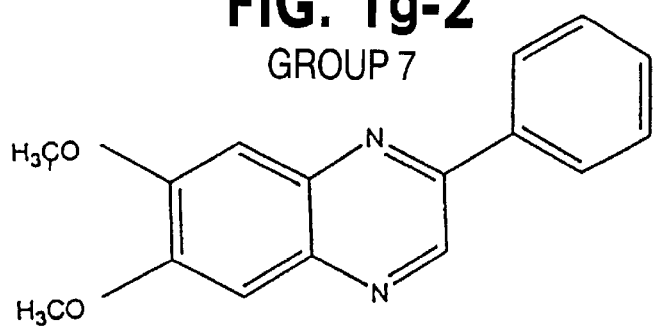
G14
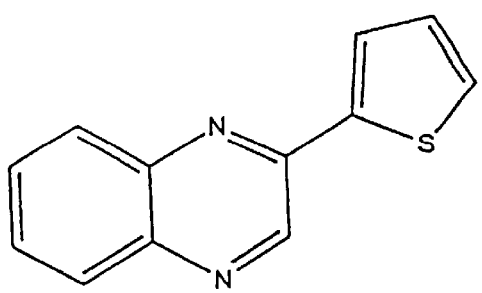
G15
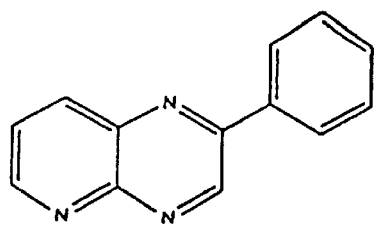
G16
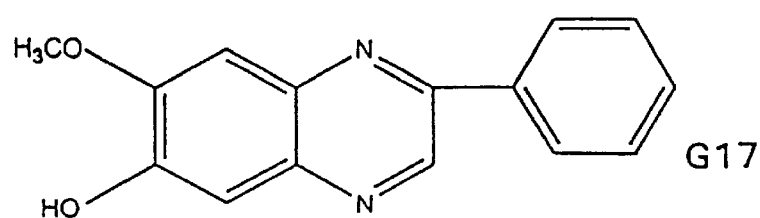
G17

FIG. 1g-3
GROUP 7
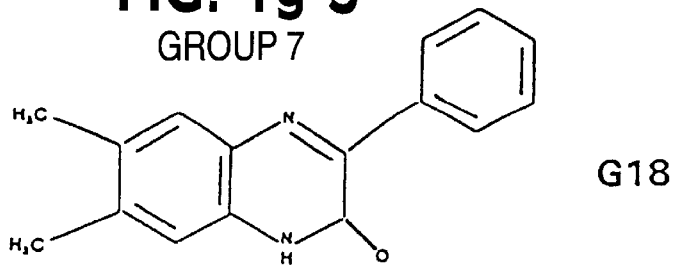
G18
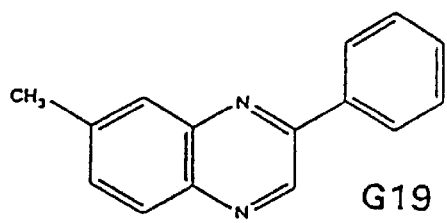
G19
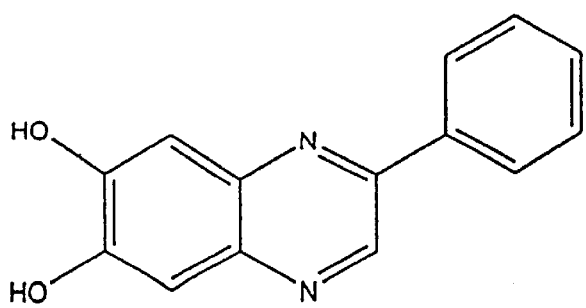
G20 (HBr salt)
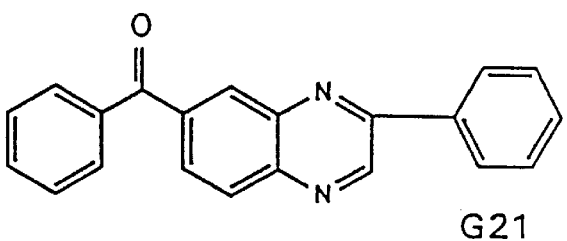
G21
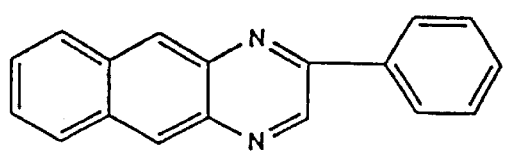
G22

FIG. 1g-4
GROUP 7
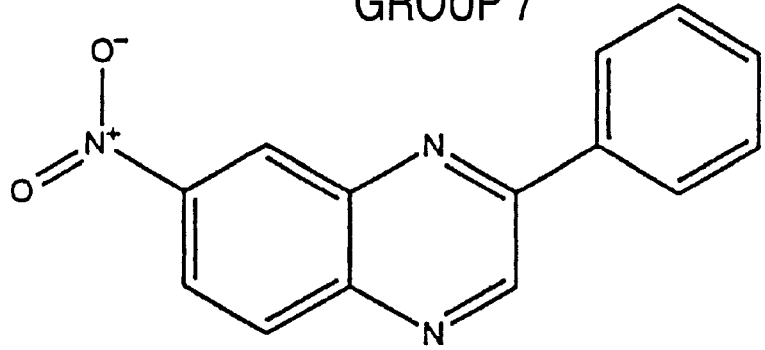
G23
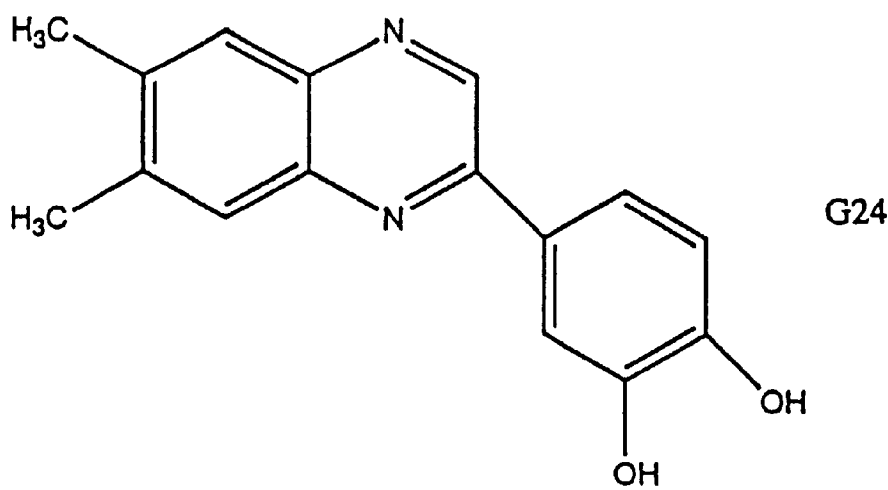
G24
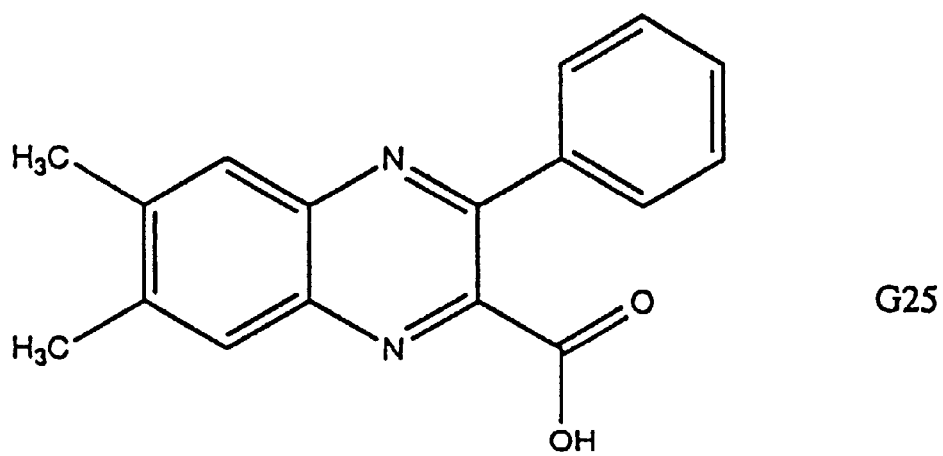
G25

FIG. 1g-5
GROUP 7
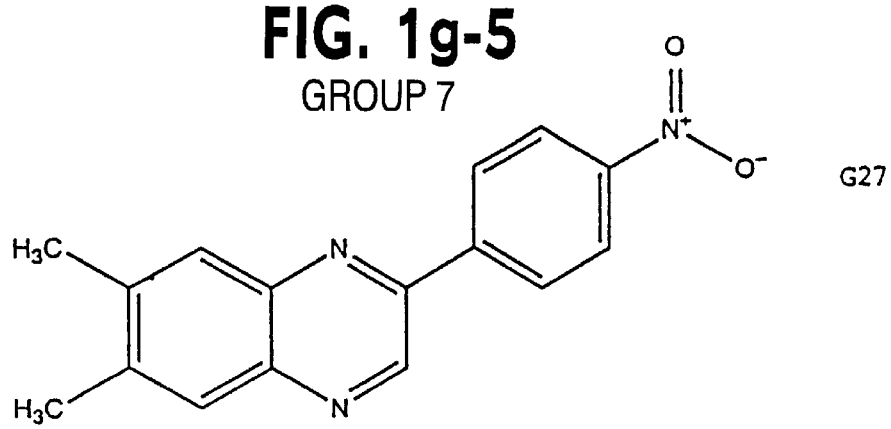
G27
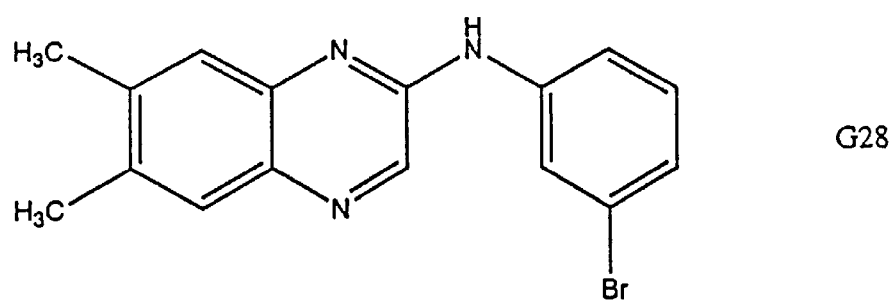
G28
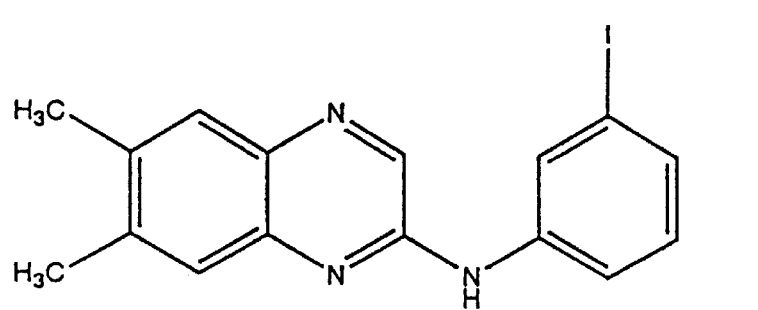
G29
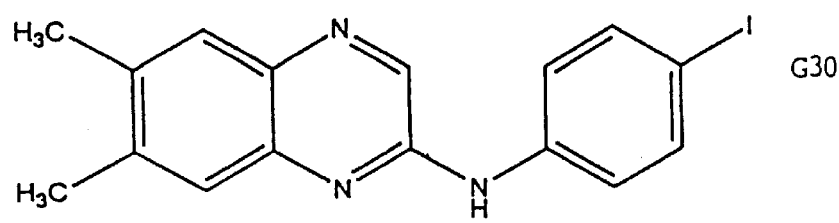
G30

FIG. 1h-1
GROUP 8
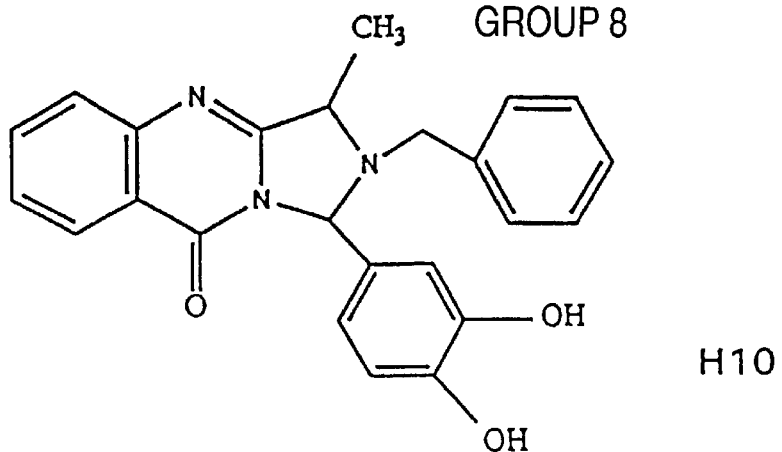
H10
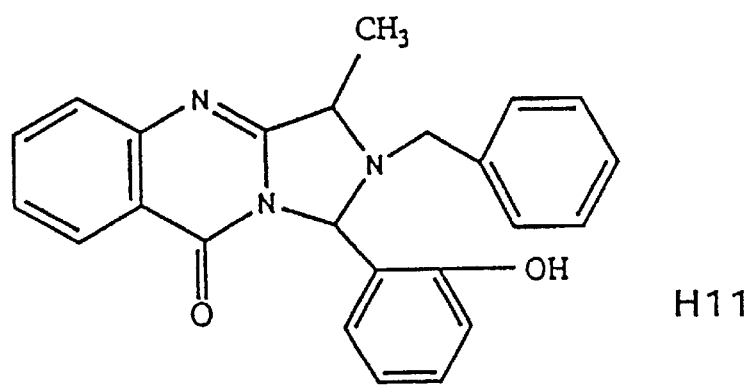
H11
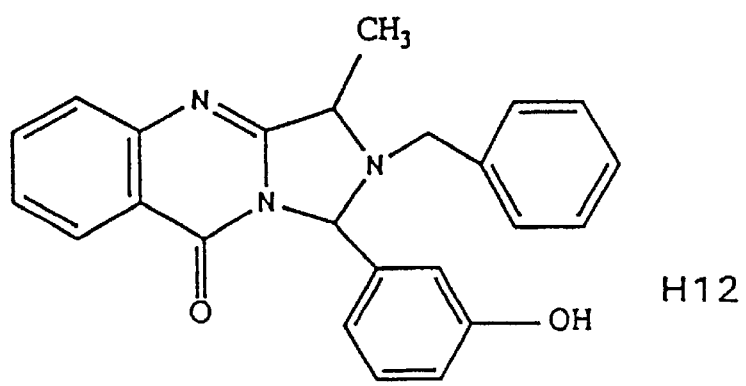
H12

FIG. 1h-2
GROUP 8
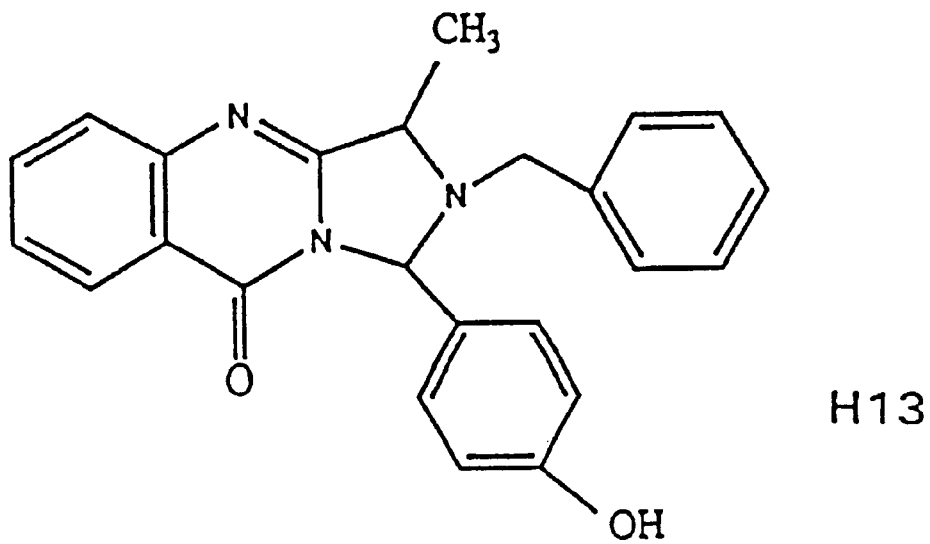
H13
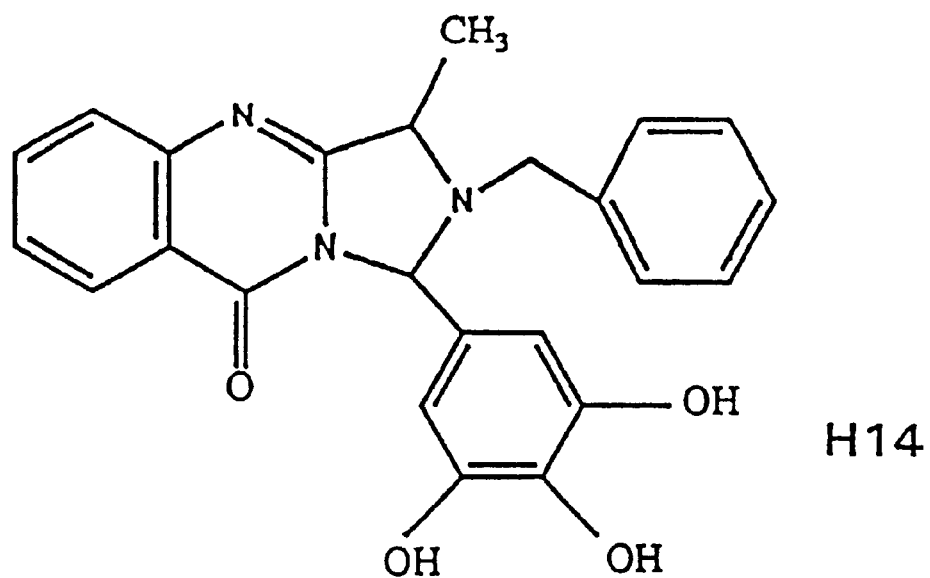
H14

GROUP 9

GROUP 10

J10

J11

FIG. 1k-1
GROUP 11
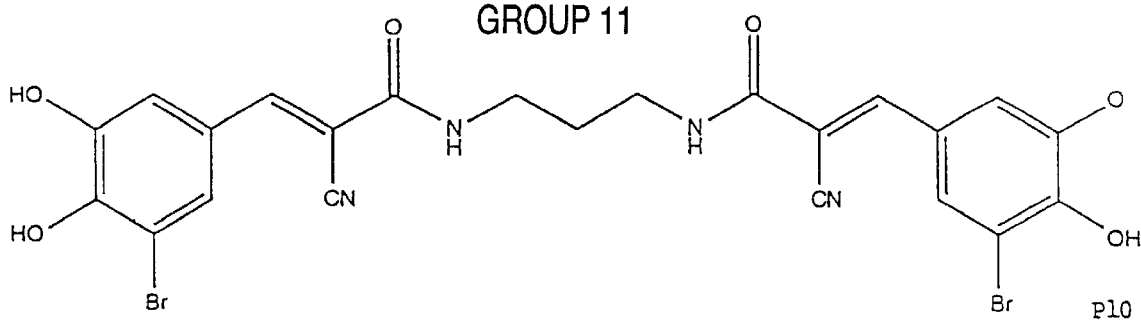
P10
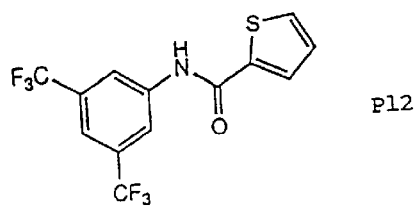
P12
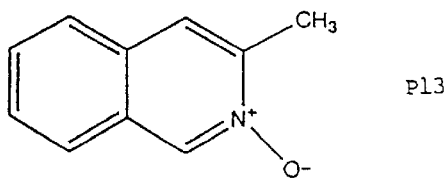
P13
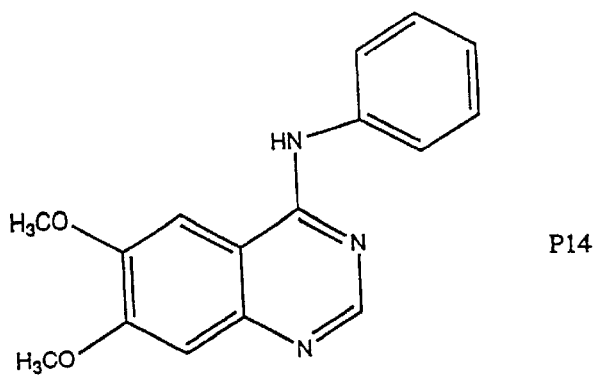
P14
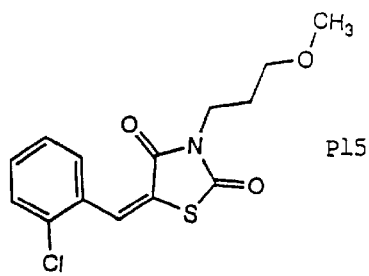
P15
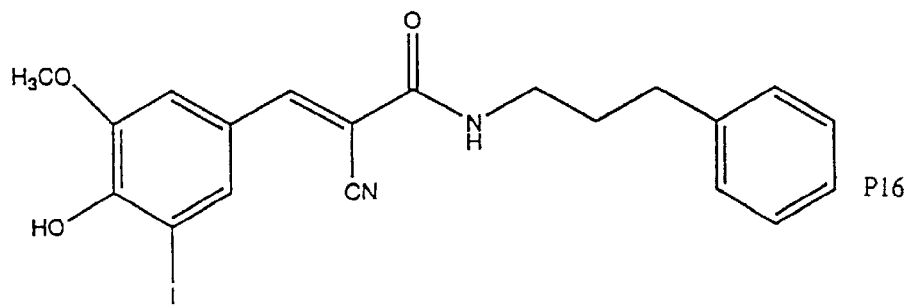
P16

GROUP 11

P17

P18

P19

P20

P21

P22

FIG. 1k-3
GROUP 11
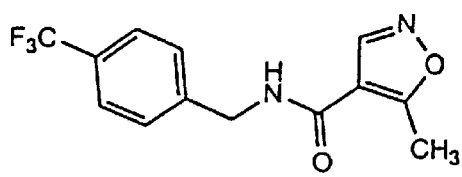
P23
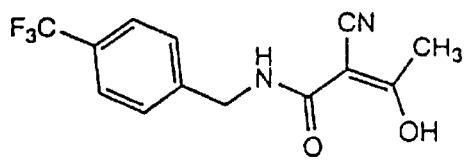
P24
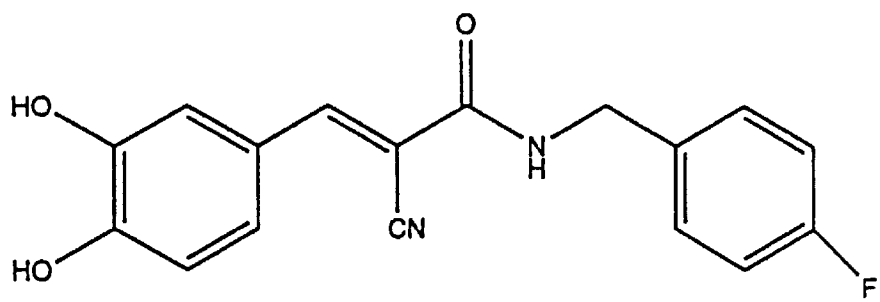
P25

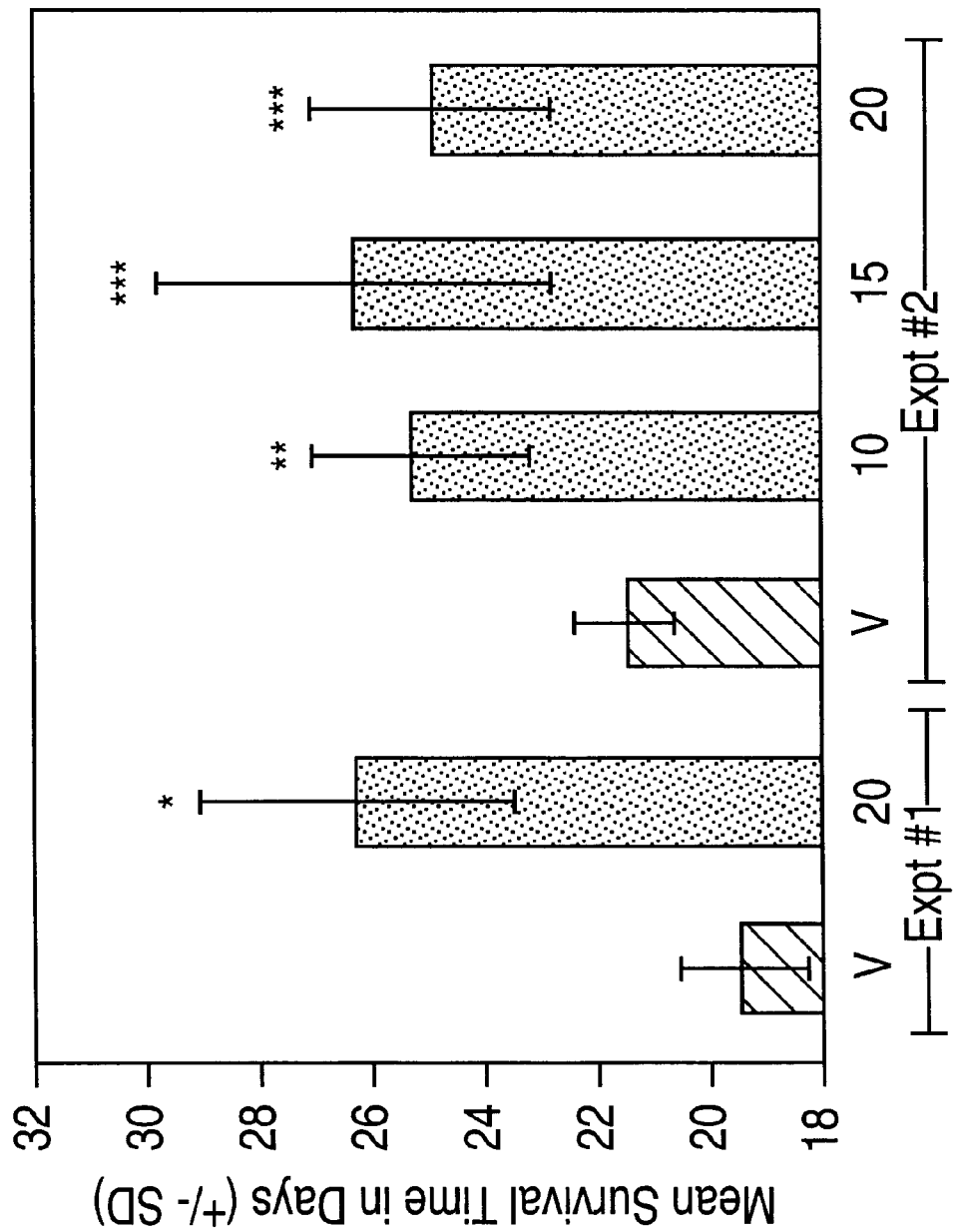

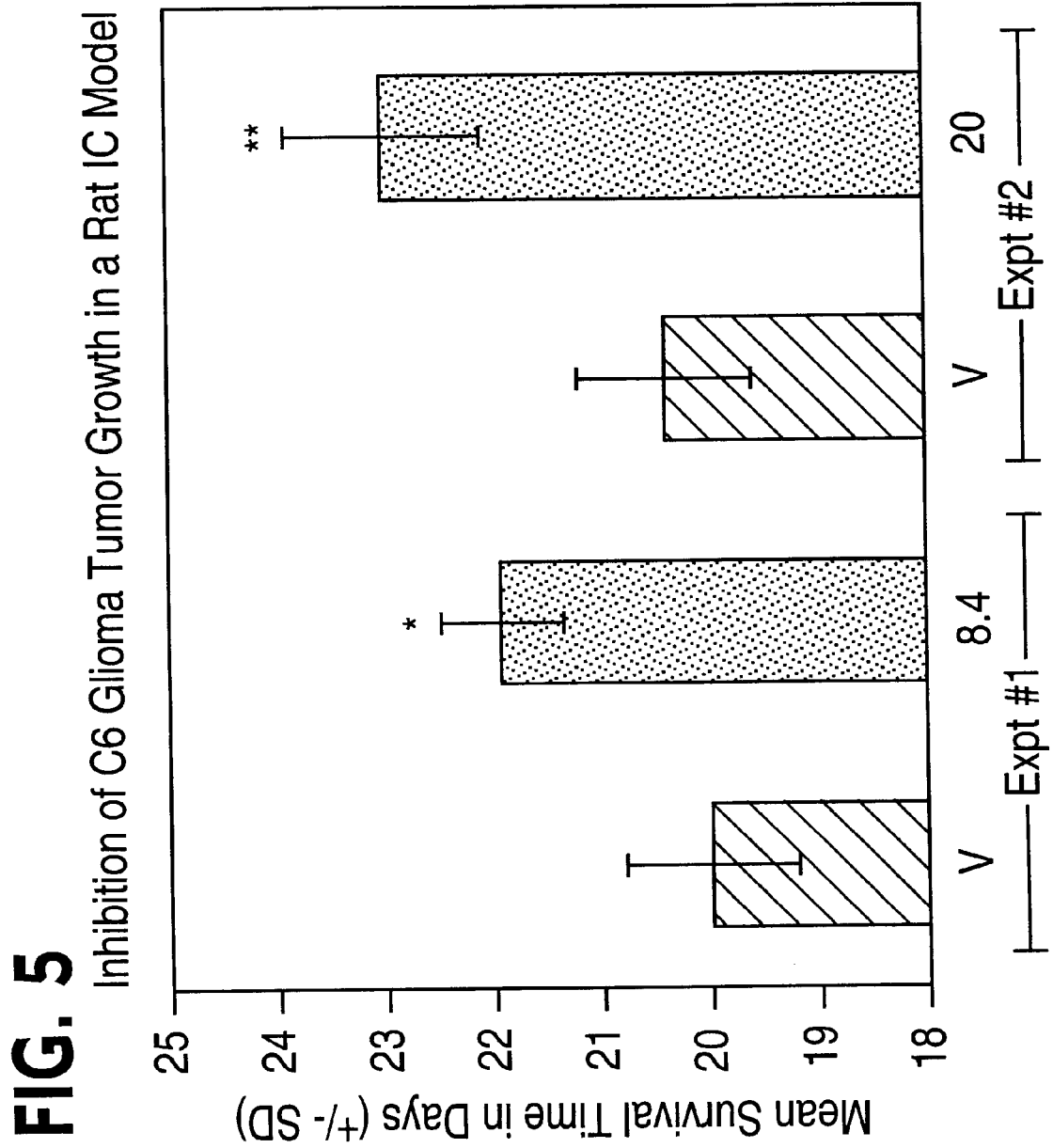
FIG. 5 Inhibition of C6 Glioma Tumor Growth in a Rat IC Model

TREATMENT OF PLATELET DERIVED GROWTH FACTOR RELATED DISORDERS SUCH AS CANCERS

RELATED APPLICATION

This application is a continuation of and claims priority to U.S. patent application Ser. No. 08/456,957, filed on Jun. 1, 1995 now abandoned, by Hirth, et al., and entitled "TREATMENT OF PLATELET DERIVED GROWTH FACTOR RELATED DISORDERS", which is incorporated herein by reference, in its entirety, including any drawings.

FIELD OF INVENTION

The present invention relates to methods and compositions for treating cell proliferative disorders characterized by inappropriate platelet derived growth factor receptor (PDGF-R) activity.

BACKGROUND OF THE INVENTION

Platelet derived growth factor receptor (PDGF-R) is a transmembrane receptor tyrosine kinase. Ligand binding to the receptor results in dimerization of two receptors generally leading to intermolecular phosphorylation of each receptor, commonly referred to as autophosphorylation or transphosphorylation, and activation of the receptor complex. PDGF, which is a ligand for PDGF-R, is a dimeric protein having two polypeptide chains joined by disulfide bonds. Each polypeptide is either an A chain polypeptide or a B chain polypeptide. Thus, PDGF can have either two A chains, two B chains, or an A and a B chain.

The PDGF-R consists of two isozymes α and β. Both α and β-containing receptors have been associated with mitogen activity, while only the β-containing receptor has been associated with chemotaxis and actin reorganization (Heldin, C-H, *EMBO Journal* 11:4251–4259, 1992).

According to Plate et al., *Laboratory Investigation* 4:529–534, 1992:

> PDGF is a potent growth factor for mesenchymal and neuroectodermal cells. Endothelial cells have been considered nonresponsive to PDGF, but a recent study has shown that PDGF may have a role in angiogenesis during placenta development. In addition, it has been demonstrated, that PDGFR-b is expressed in endothelial cells in inflammatory tissue and glial tumors. This suggests, that PDGF may play a role in vascular functions in pathological conditions. [Citations omitted.]

Heldin, supra, describes the relationship of PDGF and its receptor, and discusses the role of PDGF in cancer, noting that some cancers do not produce PDGF and have central necroses. Heldin states:

> The adverse effects of PDGF in certain diseases, as discussed above, make PDGF antagonists highly desirable. We and others have recently taken several approaches to develop such antagonists. Antibodies against PDGF have proven to be useful for inhibiting both autocrine stimulation in SSV-transformed cells and the atherosclerotic process that occurs after de-endothelialization of the carotid arteries of rats. Moreover, a soluble form of the PDGF receptor has been shown to bind and inactivate PDGF, and could thus be potentially useful for inhibiting PDGF action in vivo.
>
> Another approach would be to design or find agents that compete in an antagonistic manner with PDGF for receptor binding. In order to identify peptides that interfere with PDGF binding, we systematically screened peptides derived from the B-chain sequence. One peptide was found that inhibited PDGF binding and autophosphorylation of α- as well as β-receptors. However, the peptide also showed some cell toxicity and further development will be necessary before peptide antagonists become useful for in vivo studies. Low molecular weight compounds that interfere with receptor binding have been described, e.g., suramin. However, suramin is not specific enough to be clinically useful as a PDGF antagonist. We recently found that another low molecular weight compound, neomycin, at high concentrations inhibited the binding of PDGF-BB to the α-receptor, but did not inhibit binding to the β-receptor. This compound thus represents an antagonist that distinguishes between the two receptor types; however, its low potency makes it unsuitable for use in vivo. Hopefully, the experiences with suramin and neomycin will aid the future design of more potent and specific PDGF receptor antagonists. The design of such antagonists would be much facilitated by the elucidation of the three-dimensional structure of the PDGF-receptor complex.
>
> PDGF antagonistic activity could also be achieved by inhibition of PDGF receptor dimerization. We hypothesized that monomeric PDGF might fail to induce receptor dimerization and might thus have antagonistic activity. Since reduction of PDGF results in loss of receptor binding, we attempted to identify the interchain disulfide bonds in order to mutate these residues and thereby prevent dimerization of the ligand. This turned out to be quite difficult due to the high density of cysteine residues in PDOF. The approach that finally succeeded involved partial reduction of the PDGF molecule using a concentration of dithiothreitol that reduced only the interchain disulfide bonds, and left the intrachain bonds unaffected. By this procedure the second and fourth cysteine residues from the N-terminus were found to form the two interchain bonds in PDGF. Analysis of a PDGF B-chain mutant in which these two cysteine residues had been mutated to serine residues revealed that it retained receptor binding activity. Is it a receptor antagonist? The answer is no, in fact, the monomeric PDGF induced both receptor dimerization and autophosphorylation. This result may indicate that PDGF-induced receptor dimerization is not only a matter of forming a bridge between two receptor molecules: the dimerization may also involve a ligand-induced conformational change of the extracellular domains of the receptors which promotes receptor-receptor interactions. One possible way of achieving an antagonistic effect, which we are currently exploring, is to combine a wild-type PDGF chain with a mutated chain that does not bind to PDGF receptors but can actively prevent dimerization of receptors. [Citations omitted.]

Spada A. P., et al., entitled "Bis Mono- and Bicyclic Aryl and Heteroaryl Compounds Which Inhibit EGF and/or PDGF Receptor Tyrosine Kinase," PCT/US92/03736, mentions the use of certain bis mono and bicylic aryl compounds. According to Spada:

> In accordance with the present invention, there is provided a method of inhibiting abnormal cell proliferation in a patient suffering from a disorder characterized by such proliferation comprising the administration to a patient of an EGF and/or PDGF receptor inhibiting effective amount of a bis mono- and/or bicyclic aryl and/or heteroaryl compound exhibiting protein tyrosine kinase inhibition activity wherein each aryl and/or heteroaryl group is a ring system containing 0–4 hetero atoms, said compound being optionally substituted or polysubstituted.

SUMMARY OF THE INVENTION

The present invention concerns compounds which can inhibit platelet derived growth factor receptor (PDGF-R) activity, preferably such compounds also inhibit the activity of other members of the PDGF-R super family and are selective for members of the PDGF-R super family. The PDGF-R super family includes PDGF-R and PDGF-R related kinases Flt, and KDR. The featured compounds are active on cell cultures to reduce the activity of the PDGF-R and preferably one or more PDGF-R related kinases. An example of a featured compound, A10 (see FIG. 1a), and its ability to inhibit growth, of tumor cells in vivo is described below. Using the present application as guide other compounds able to inhibit PDGF-R and preferably Flt and/or KDR can be obtained. Such compounds are preferably used to treat patents suffering from cell proliferative disorders characterized by inappropriate PDGF-R activity.

Unwanted cell proliferation can result from inappropriate PDGF-R activity occurring in different types of cells including cancer cells, cells surrounding a cancer cell (stromal cells), endothelial and smooth muscle cells. For example, an increase in PDGF-R activity of endothelial cells surrounding cancer cells may lead to an increased vascularization of the tumor, thereby facilitating growth of the cancer cells. Thus, inappropriate PDGF-R activity can contribute to a cell proliferative disorder in different ways such as through increasing the production of growth factors, causing aberrant growth of a cell, and increasing formation and spreading of blood vessels in solid tumors thereby supporting tumor growth.

Other members of the PDGF-R super family are also involved in supporting tumor growth. Members of the PDGF-R super family have a kinase domain containing at least 45% sequence similarity with the kinase domain of α or β PDGF-R. Vascular endothelial growth factor (VEGF) activates at least tyrosine kinase receptors; Flk-1 or its human homologue KDR, and Flt-1. Both of these receptors are expressed on endothelial cells and appear to be important in angiogenesis. Plate et al., *Nature* 359:845–848, 1992; Shweiki, et al., *Nature* 359:843–845, 1992; Millauer et al., *cell* 72:835–846, 1993; Plate et al., *Cancer Res.*, 53:5822–5827, 1993; Waltenberger et al., *Journal of Biological Chemistry* 43:26988–26995, 1994. Vascularization is essential for solid tumor growth and is thought to be regulated by tumor cell factors which have chemotactic and/or mitogenic effects on endothelial cells. PDGF-R, KDR and Flt-1, are all involved in blood vessel formation and spreading feeding solid tumors. By inhibiting both PDGF-R and one or more related tyrosine kinase activities both aberrant cell growth and the feeding of such growth can be inhibited.

Many examples of compounds (see FIGS. 1a–k) belonging to the featured groups (see FIGS. 2a–j) are described. Those skilled in the art can obtain other compounds, to inhibit PDGF-R and preferably Flt and/or KDR, having equivalent or greater activity at these receptor tyrosine kinases using the present disclosure as a guide. For example, the assays described herein can be used to readily screen other compounds belonging to the featured groups (see, FIGS. 2a–j) for equivalent activity. Using standard assays, the site of action of any one of the compounds described below may be determined and other compounds active at the same site determined.

The methods and compositions are designed to inhibit unwanted cell proliferation by altering the activity of the PDGF-R, and preferably also altering activity of Flt and/or KDR. Without being bound to any theory, inhibition of unwanted cell proliferation may be brought about by altering the activity of the PDGF-R (e.g., by inhibiting tyrosine phosphorylation of PDGF-R, by inhibiting substrate or adaptor protein binding to the receptor, or by inhibiting other downstream signaling events), thereby inhibiting the activity of the PDGF-R. However, unless otherwise stated, the use of the claimed methods and compositions are not limited to this particular theory.

Thus, a first aspect of the present invention features a method for treating a patient inflicted with a cell proliferative disorder characterized by inappropriate PDGF-R activity. The method involves the step of administering to the patient a therapeutically effective amount of a composition comprising a compound illustrated in FIG. 2a–j, or the active product formed when any such compound is placed under physiological conditions (i.e., the active structural entity of a pro-drug described above). Administration of a particular compound is achieved by providing a particular compound to the patient or providing a prodrug of the compound to a patient which forms the particular compound in vivo.

"Cell proliferative disorders" refer to disorders wherein unwanted cell proliferation of one or more subset of cells in a multicellular organism occurs resulting in harm (e.g., discomfort or decreased life expectancy) to the multicellular organism. Cell proliferative disorders can occur in different types of animals and in humans. Cell proliferative disorders include cancers, blood vessel proliferative disorders, and fibrotic disorders.

"Inappropriate PDGF-R activity" refers to either 1) PDGF-R expression in cells which normally do not express PDGF-R; 2) PDGF expression by cells which normally do not express PDGF; 3) increased PDGF-R expression leading to unwanted cell proliferation; 4) increased PDGF expression leading to unwanted cell proliferation; or 5) mutations leading to constitutive activation of PDGF-R. The existence of inappropriate or abnormal PDGF and PDGF-R levels or activities is determined by procedures well known in the art.

The compositions can be used to treat a cell proliferative disorder by administering a therapeutically effective amount of the composition to a patient (i.e. a human or an animal having a cell proliferative disorder). The compositions may also be used in in vitro studies of the mechanism of action of the PDGF-R or PDGF itself.

A "therapeutically effective amount", in reference to the treatment of a cancer refers to an amount sufficient to bring about one or more the following results: reduce the size of the cancer, inhibit the metastasis of the cancer, inhibit the growth of the cancer, stop the growth of the cancer, relieve discomfort due to the cancer, or prolong the life of a patient inflicted with the cancer.

A "therapeutically effective amount", in reference to the treatment of a cell proliferative disorder other than a cancer refers to an amount sufficient to bring about one or more of the following results: inhibit the growth of cells causing the disorder, relieve discomfort due to the disorder, or prolong the life of a patient suffering from the disorder.

"Significant" inhibition of a receptor tyrosine kinase activity refers to an $IC_{50}$ of less than or equal to 75 $\mu$M using one or more of the assays described in the Examples infra. Preferably, the compound can inhibit PDGF-R activity with an $IC_{50}$ of less than or equal to 50 μM, more preferably less than or equal to 1 μM. Lower $IC_{50}$ values are preferred because the $IC_{50}$ provides an indication as to the in vivo effectiveness of the compound. Other factors known in art, such as compound half-life, bio distribution, and toxicity should also be considered for therapeutic uses. Such factors may enable a compound with a lower $IC_{50}$ to have greater in vivo efficacy than a compound having a higher $IC_{50}$.

Selective inhibition of the PDGF-R super family is achieved by significantly inhibiting PDGF-R activity, while having an insignificant effect (i.e. an $IC_{50}$ for tyrosine phosphorylation greater than 100 μM on EGF-R.) Preferably, at least one other member of the PDGF-R super family, is significantly inhibited.

Preferably, the compound is either A10, A11, A12, A13, B10, B11, B12, B13, B14, B15, B16, B17, B18, B19, C10, C11, C13, D11, D12, D13, D14, D15, D16, D17, D18, D20, E10, E11, E12, E13, E14, E15, E16, F10, F11, F12, G10, G11, G12, G13, G14, G15, G16, G17, G18, G19, G20, G21, G22, G23, G24, G25, G27, G28, G29, G30, H12, I10, J11, P10, P12, P13, P14, P15, P16, P17, P18, P19, P20, P21, P22, P23, P24, P25 or the active drug of such compounds, or pharmaceutically acceptable salts thereof. The compound is preferably used in a pharmaceutical composition formed by mixing one of the above compounds and a physiological acceptable carrier.

A physiological acceptable carrier is a formulation to which the compound can be added to dissolve or otherwise facilitate administration of the compound. Examples of physiological acceptable carriers include water, saline, physiologically buffered saline, cyclodextrins and PBTE:D5W. Hydrophobic compounds such as A10 are preferably administered using a carrier such as PBTE:D5W. An important factor in choosing an appropriate physiological acceptable carrier is choosing a carrier in which the compound remains active or the combination of the carrier and the compound produces an active compound. The compound may also be administered in a continuous fashion using a slow release formulation or a pump to maintain a constant or varying drug level in a patient.

Another aspect of the present invention features a method of treating a patient suffering from a cell proliferative disorder characterized by inappropriate PDGF-R activity using A10, A12, or B11. The method involves administering to a patient a therapeutically effective amount of A10, A12, or B11.

Another aspect of the present invention describes a method of treating a patient suffering from a cancer characterized by inappropriate PDGF-F activity using combination therapy. Combination therapy is carried out using one or more agents described herein along with standard anti-cancer agents. The method is carried out by administering to a cancer patient a therapeutically effective amount of a composition comprising an agent able to significantly inhibit PDGF-R activity and a cytotoxic agent. Preferably, the cytotoxic agent is VF-16 or cisplatin. More preferably, the cytotoxic agent is cisplatin and the cancer is lung cancer.

Another aspect of the present invention features a method for treating a patient having a cell proliferation disorder characterized by inappropriate PDGF-R activity using mutated PDGF-R, or nucleic acid encoding a mutated PDGF-R. "Mutated" PDGF-R refers to PDGF-R wherein one or more amino acid is missing or altered. As illustrated below a nucleic acid encoding a mutated (i.e., a truncated) PDGF-R lacking a kinase domain can inhibit tumor growth in vivo. Mutated PDGF-R can be administered as a protein, or recombinant nucleic acid encoding the protein and expressing the protein inside a cell.

In other aspects, the invention features novel compositions including one of the featured compounds herein described and PBTE:D5W carrier where the featured compound is soluble in PBTE:D5W; and the novel compounds B10, B12, C10, C11, E10, E11, E12, E13, E14, E15, E16, F10, F11, F12, G21, G22, H11, H12, H13, and H14.

Other features and advantages of the invention will be apparent from the following description of the preferred embodiments thereof, and from the claims.

BRIEF DESCRIPTION OF THE FIGURES

FIG. 4. In two separate experiments, C6 cells ($1\times10^5$ cells in 4 μL) were implanted into the cerebrum of BALB/c, nu/nu mice. A10 was administered IP in 100 μL PBTE:D5W at the indicated doses every day starting one day post-implantation. V=vehicle control. n=8 to 12 (Expt #1), or 5 (Expt #2) animals per group. * $P<0.00001$;  $P<0.002$; * $P<0.02$ compared to vehicle control.

FIG. 5. In two separate experiments, C6 cells ($5\times10^4$ cells in 20 μL [Expt #1] or 5 μL [Expt #2]) were implanted into the cerebrum of athymic rats. A10 was administered IP in 500 μL PBTE at the indicated doses every day starting one day post-implantation. V=vehicle control. n=7 to 8 animals per group. * $P=0.0002$; ** $P=0.0003$ compared to vehicle control.

DETAILED DESCRIPTION OF THE INVENTION

Figures 1, 1A, 2:
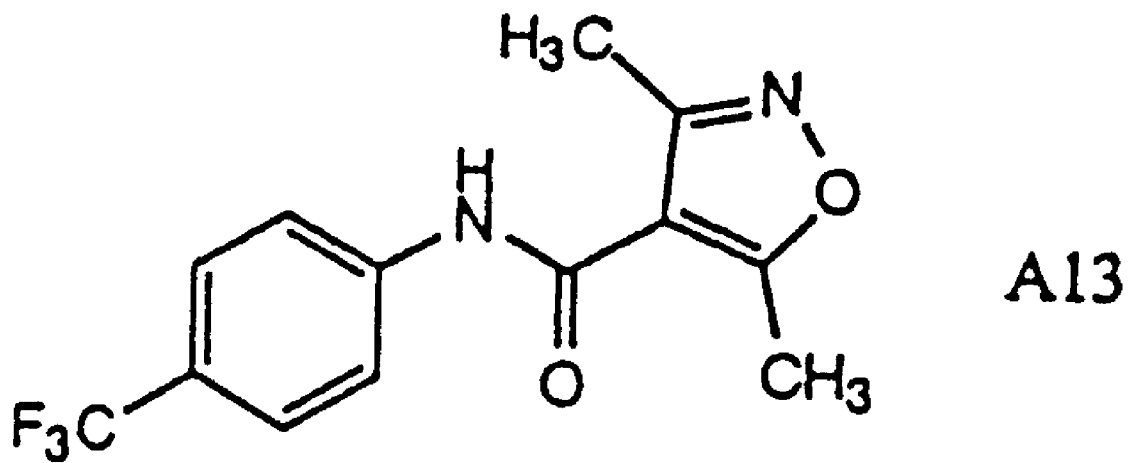
FIGS. 1a–k illustrate the chemical structures of the preferred compounds.

The present invention features methods and compositions for treating cell proliferative disorders characterized by inappropriate PDGF-R activity. The present application demonstrates the ability of compounds able to significantly inhibit activity of Flt-1 and/or PDGF-R, and provides examples of such compounds useful for treating a proliferative disease, such as cancer. The compounds described herein can be used in treatment of other proliferative diseases associated with inappropriate expression of PDGF-R, for example, blood vessel proliferative disorders and fibrotic disorders characterized by inappropriate PDGF-R activity. Using the present disclosure as a guide, those in the art can readily determine which of the compounds described herein are useful to treat a particular proliferative disease.

A single target site, the presence of inappropriate PDGF-R activity, for a large number of disorders out of the many proposed targets in the art along with compounds able to inhibit PDGF-R activity and preferably Flt and/or KDR activity are described by the present application. Preferably, PDGF-R activity along with KDR and/or Flt activities are inhibited by a single compound such as A10. Combinations of compounds or types of treatments can also be used to target different PDGF-R related tyrosine kinases. Examples of such combinations include using a PDGF-R activity inhibitory compounds along with a KDR inhibitory compound, and using PDGF-R nucleic acid to inhibit production of PDGF=R along with a KDR inhibitory compound.

Compounds (also referred to herein as "drugs") useful in this invention belong to at least eight different groups. The preferred compounds of these groups, and in other as yet undefined groups, that have generally exhibited significant inhibition of PDGF receptor activity are shown in FIGS. 1a–k. While generic formulae are presented, those in the art will recognize that those compounds useful in the invention can be determined by screening procedures described herein and known in the art.

The ability of A10, truncated versions of a PDGF-R and other compounds to inhibit tumor growth in animals illustrates the effectiveness and efficacy of these compounds. Such animal studies support the effectiveness of the compounds by demonstrating that the compounds can be effective in animals despite various problems which are inherently associated with using compounds in animals to treat a particular ailment. The inherent problems include the animal being comprised of a heterogeneous cell population, various pharmacological considerations such as bioavailability of the compound, the half life of the compound, and clearance of the compound. These inherent problems often prevent a compound from exerting a physiological effect.

Examples are provided below illustrating the ability of various compounds to inhibit PDGF-R phosphorylation. Examples are also provided illustrating the ability of the compound termed A10 (see FIG. 1a) to inhibit cancers in vivo. Using the present disclosure as a guide one skilled in the art can use the featured methods and compositions to obtain additional inhibitory compounds and to target other cell proliferative disorders characterized by an inappropriate PDGF-R activity.

I. PDGF-R Super Family

A. PDGF-R Activity

Ligand binding to the PDGF-R induces the formation of receptor dimers and allosteric changes that activate the intracellular kinase domains, and results in the transphosphorylation and/or autophosphorylation of the receptor on tyrosine residues. Receptor phosphorylation stimulates a physical association of the activated receptor with target molecules. Some of the target molecules are in turn phosphorylated, which transmits the signal to the cytoplasm. Other target molecules are not phosphorylated, but assist in signal transmission by acting as docking or adapter molecules for secondary signal transducer proteins. The secondary signal transducer molecules generated by activated receptors results in a signal cascade that regulates cell functions such as cell division. (See, Fry M. J. et al., *Protein Science* 2:1785–1797, 1993)

Thus, an increase in PDGF-R activity is characterized by an increase in one or more of the activities which can occur upon PDGF-R ligand binding: (1) phosphorylation or autophosphorylation of PDGF-R, (2) phosphorylation of a PDGF-R substrate (e.g., PL 3-kinase, RasGAP, PLCγ, see Fry supra), (3) activation of an adapter molecule, and (4) increased cell division. These activities can be measured using techniques described below and known in the art. For example autophosphorylation of PDGF-R can be measured as described in the examples below using an antiphosphotyrosine antibody, and increased cell division can be measured as described below by measuring 3H-thymidine incorporation into DNA. Preferably, the increase in PDGF-R activity is associated with an increased amount of phosphorylated PDGF-R and DNA synthesis.

B. PDGF-R Related Kinases

PDGF-R related kinases Flt-1 and KDR can be activated by VEGF. VEGF is a monodimeric glycoprotein with structural homology to PDGF. Four different splice variants of VEGF have been isolated. Rosenthal, et al., *Growth Factors*, 4:53–59, 1990; Conn, et al., *Proc. Natl. Acad. Sci. (USA)*, 87:1323–1327, 1990; Houck, et al., *Mol. endocrinol.*, 5:1806–1814, 1991; two are secreted forms and two remain cell-associated. VEGF has been shown to be upregulated by hypoxia and acts specifically on endothelial cells. Plate et al., *Nature*, 359:845–848, 1992; Shweike, et al., *Nature* 359:843–845, 1992.

KDR activity is characterized by an increase in one or more of the activities which can occur upon VEGF ligand binding: (1) phosphorylation or autophosphorylation of KDR, (2) phosphorylation of a KDR substrate, (3) activation of an adapter molecule, and (4) increased cell division.

Flt-1 activity is characterized by an increase in one or more of the activities which can occur upon VEGF ligand binding: (1) phosphorylation or autophosphorylation of Flt-1, (2) phosphorylation of a Flt-1 substrate, (3) activation of an adapter molecule, and (4) increased cell division.

II. Featured Compounds

Compounds of groups 1 to 11 are shown in FIGS. 2a–k.

A. Group 1 compounds

Group 1 compounds have the following basic structure:

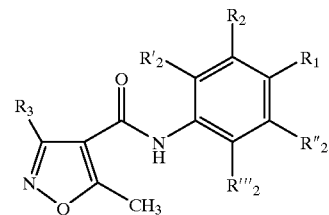

where $R_1$, $R_2$, $R'_2$, $R''_2$, and $R'''_2$ are independently selected from the group consisting of hydrogen, halogen, trihalomethyl, and $NO_2$; preferably $R_1$ and $R_2$ are independently $CF_3$, $NO_2$ or hydrogen, and $R'_2$, $R''_2$, and $R'''_2$ are hydrogen; and $R_3$ is selected from the group consisting of hydrogen, carboxy, methyl, methoxy, alkoxy, or carbalkoxy; preferably hydrogen, carboxy, methyl, or methoxy.

Examples of group 1 compounds are listed in Table I and shown in FIG. 1a.

TABLE I

| Compound | $R_1$ | $R_2$ | $R_3$ |
|---|---|---|---|
| A10 | $CF_3$ | H | H |
| A11 | H | $CF_3$ | H |
| A12 | $CF_3$ | H | Carboxy |
| A13 | $CF_3$ | H | $CH_3$ |

These compounds are believed to act as prodrugs in that the ring is cleaved in vivo to yield active metabolites.

B. Group 2 compounds

Group 2 compounds have the following basic structure:

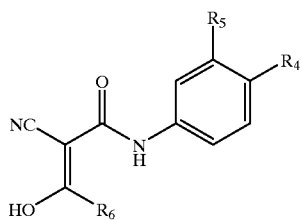

where $R_4$ and $R_5$ are independently halogen, hydrogen, trihalomethyl, or $NO_2$; preferably $R_4$ is $CF_3$ and $R_5$ is H; $R_6$ is either aryl, alkyl, alkenyl, or alkynyl;

$R_6$ is preferably alkyl or one of the substituents of the compounds listed in Table II. Examples of group 2 compounds are listed in Table II and shown in FIG. 1b.

TABLE II

| Compound | $R_4$ | $R_5$ | $R_6$ |
|---|---|---|---|
| B10 | $NO_2$ | H | $CH_3$ |
| B11 | $CF_3$ | H | $CH_3$ |
| B12 | $CF_3$ | H | 4-fluorophenyl |
| B13 | $CF_3$ | H | cyclohexyl |
| B14 | $CF_3$ | H | 2,2,3,3-tetramethylcyclopropyl |
| B15 | $CF_3$ | H | pentafluorophenyl |
| B16 | $CF_3$ | H | 3-phenoxy-phenyl |
| B17 | $CF_3$ | H | benzyl |
| B18 | $CF_3$ | H | 2-methylpropyl |
| B19 | $CF_3$ | H | diphenylmethyl |

C. Group 3 Compounds

Group 3 compounds have the following structure:

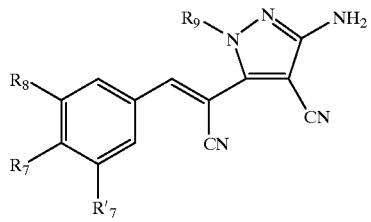

where $R_7$, $R'_7$, and $R_8$ are independently halogen, OH, hydrogen, alkoxy, SH, $NH_2$, or $C(CH_3)_3$, preferably $R'_7$, $R_7$, and $R_8$ is independently selected from H, OH, and $C(CH_3)_3$; more preferably, $R_7$ and $R_8$ are OH; $R_9$ is aryl or hydrogen, preferably hydrogen or phenyl.

Figure 1C:
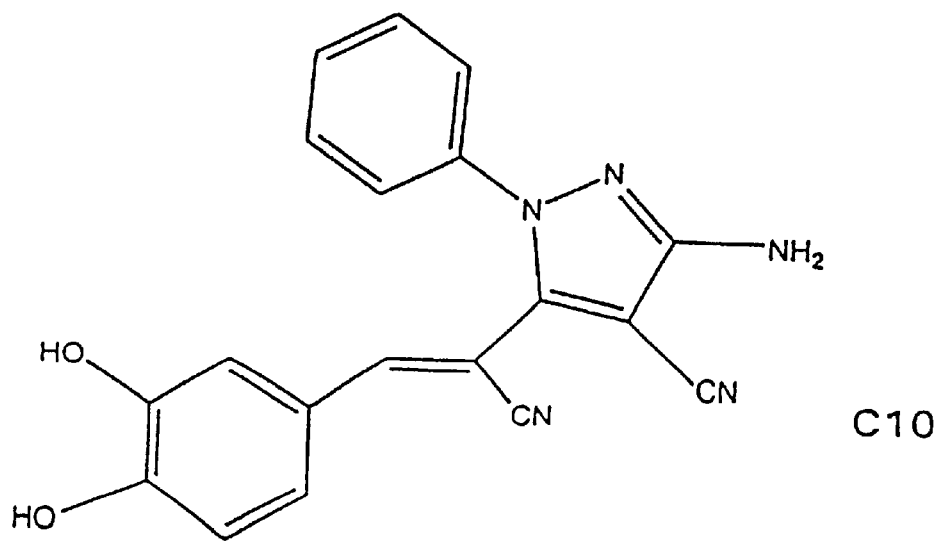
Figure 1:
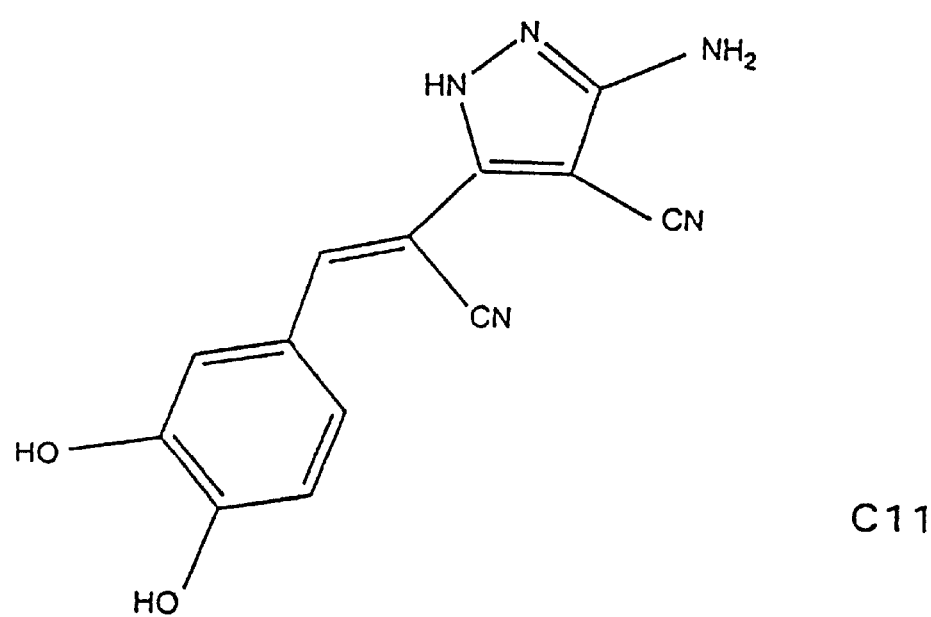
Figures 1, 1C, 2:
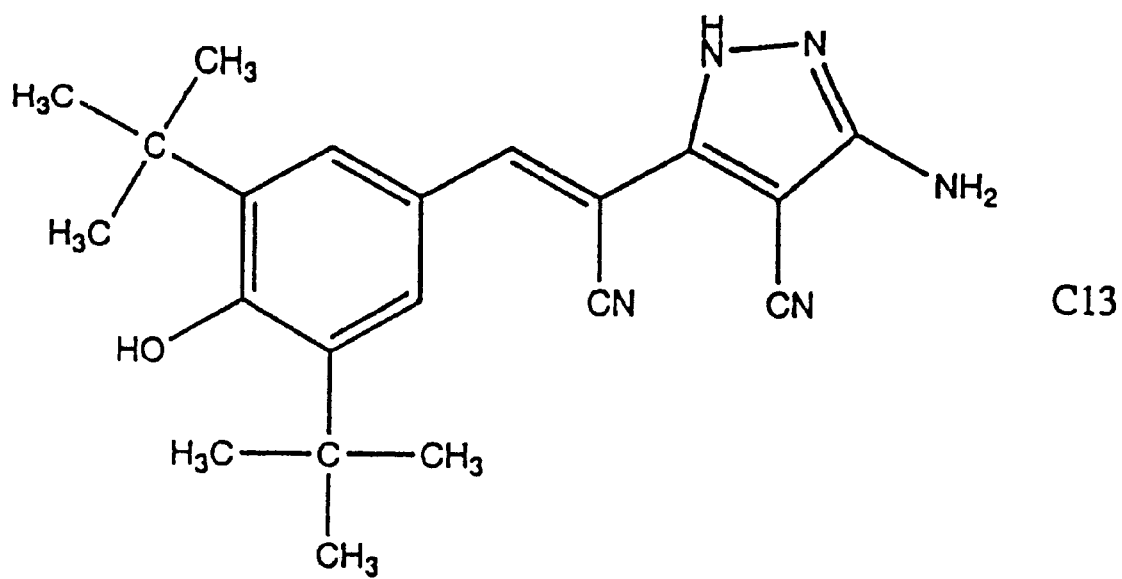

Examples of group 3 compounds are listed in Table III and shown in FIG. 1c.

TABLE III

| Compound | $R'_7$ | $R_7$ | $R_8$ | $R_9$ |
|---|---|---|---|---|
| C10 | H | OH | OH | phenyl |
| C11 | H | OH | OH | H |
| C13 | $C(CH_3)_3$ | OH | $C(CH_3)_3$ | H |

D. Group 4 Compounds

Group 4 compounds have the following chemical structure:

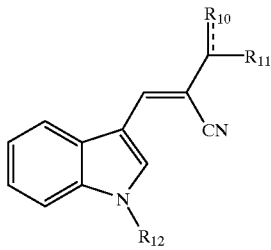

where $R_{10}$ is either =S, =O, SH, OH, or $NH_2$; and $R_{11}$ is SH, OH, $NH_2$, =$C(CN)_2$ or aryl, preferably $NH_2$, =$C(CN)_2$, or dihydroxyl-phenyl; or $R_{10}$ and $R_{11}$ taken together are aryl, preferably 3-amino-4-cyano-5-pyrazole or 1-phenyl-3-amino-4-cyano-5-pyrazole; and $R_{12}$ is hydrogen, aryl, alkyl, alkenyl, or alkynyl, preferably hydrogen, —$(CH_2)_2CN_2$ or —$(CH_2)_2N(CH_3)_2$.

Examples of group 4 compounds are listed in Table IV and shown in FIG. 1d.

TABLE IV

| Compound | $R_{10}$ | $R_{11}$ | $R_{12}$ |
|---|---|---|---|
| D11 | =S | $NH_2$ | H |
| D12 | $NH_2$ | =$C(CN)_2$ | H |
| D13 | =O | $NH_2$ | H |
| D14 | 3-amino-4-cyano-5-pyrazoyl | | H |
| D15 | 3-amino-4-cyano-5-pyrazoyl | | —$(CH_2)_3N(CH_3)_2$ |
| D16 | =O | 3,4-dihydroxyl-phenyl | —$(CH_2)_3N(CH_3)_2$ |
| D17 | =O | 3,4-dihydroxyl-phenyl | —$(CH_2)_2CN$ |
| D18 | 3-amino-4-cyano-5-pyrazoyl | | $(CH_2)_2N(CH_3)_2$ |
| D20 | 1-phenyl-3-amino-4-cyano-5-pyrazoyl | | H |

E. Group 5 Compounds

Group 5 compounds have the following chemical structure:

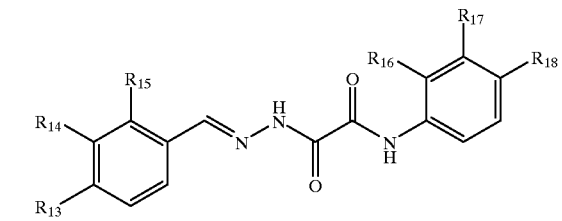

where $R_{13}$, $R_{14}$, $R_{15}$, $R_{16}$, $R_{17}$, and $R_{18}$ are independently hydrogen, halogen, alkoxy, OH, amino, alkylamino, or SH; preferably hydrogen or OH.

Figure 1E:
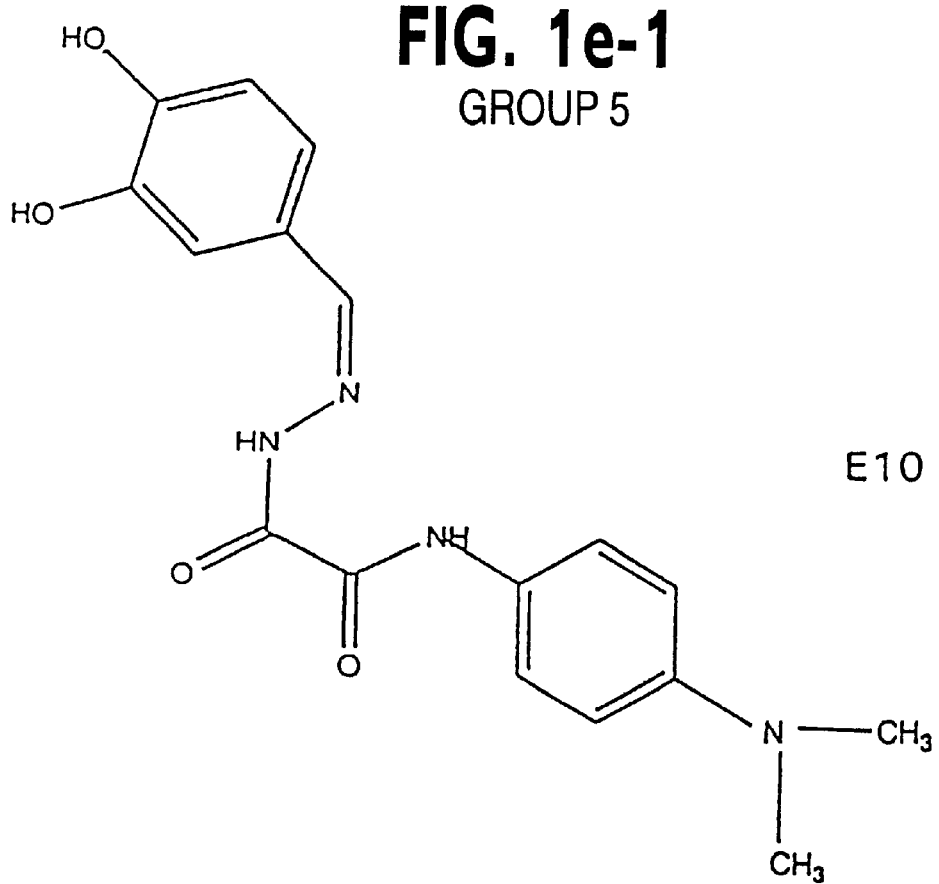
Figure 1:
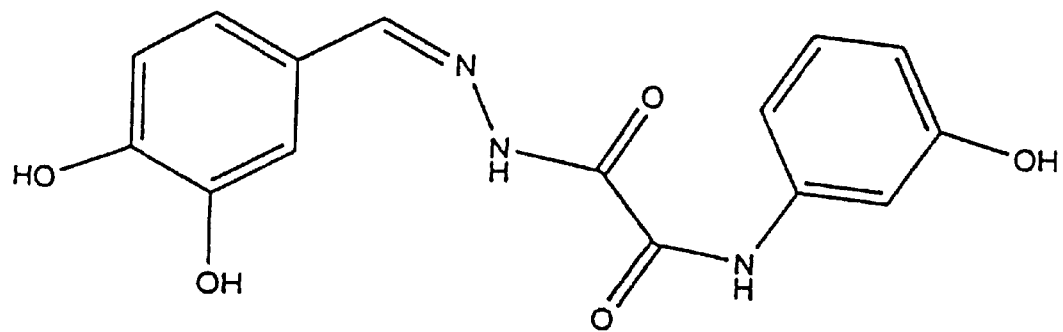
Figure 1E:
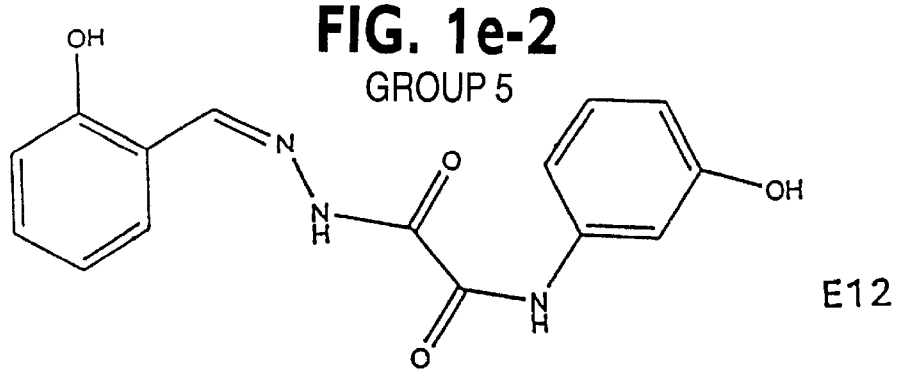
Figure 1:
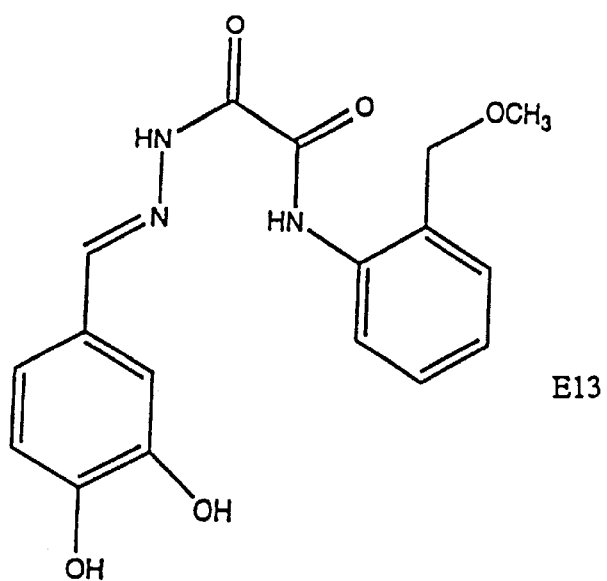
Figure 2:
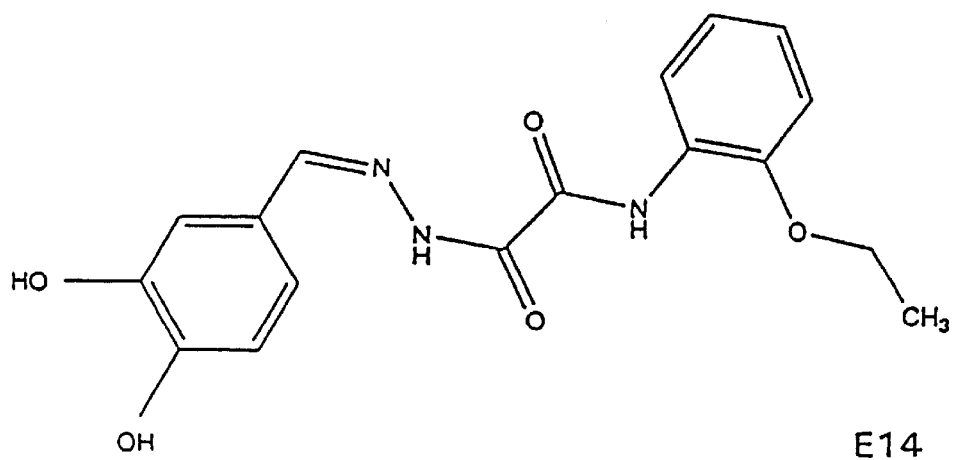
FIGS. 2a–j illustrate the generic chemical structure of groups 1–10 respectively.

Examples of group 5 compounds are listed in Table V and shown in FIG. 1e.

TABLE V

| Compound | $R_{13}$ | $R_{14}$ | $R_{15}$ | $R_{16}$ | $R_{17}$ | $R_{18}$ |
|---|---|---|---|---|---|---|
| E10 | OH | OH | H | H | H | $N(CH_3)_2$ |
| E11 | OH | OH | H | H | OH | H |
| E12 | H | H | OH | H | OH | H |
| E13 | OH | OH | H | $OCH_3$ | H | H |
| E14 | OH | OH | H | $OC_2H_5$ | H | H |
| E15 | OH | OH | H | H | $NO_2$ | H |
| E16 | OH | H | H | H | $NO_2$ | H |

F. Group 6 Compounds

Group 6 compounds have the following chemical structure:

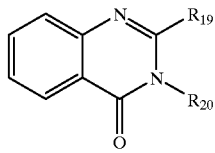

where $R_{19}$ is aryl, alkyl, alkenyl or alkynyl preferably 2-(3,4,-dihydroxyphenyl)ethenyl; $R_{20}$ is an alkyl preferably ethylenehydroxy; or $R_{19}$ and $R_{20}$ are together aryl preferably a morpholine ring having a =CH-(mono or dihydroxy-phenyl) substituent.

Figure 1F:
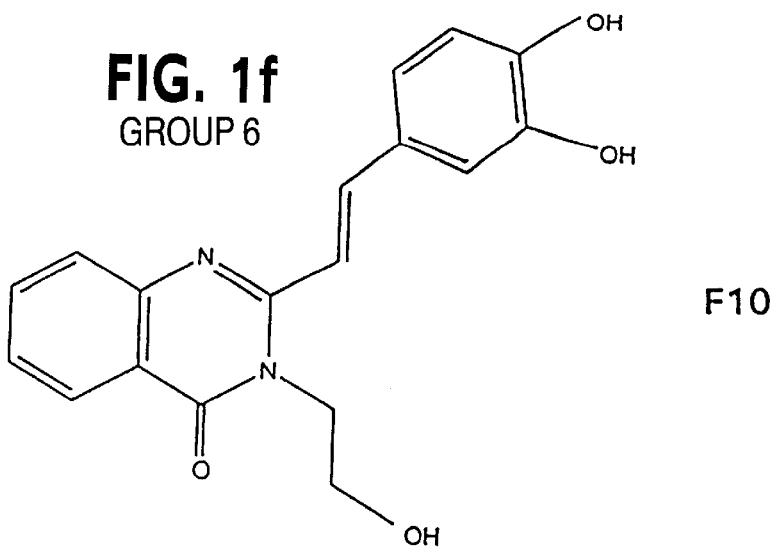
Figure 1F:
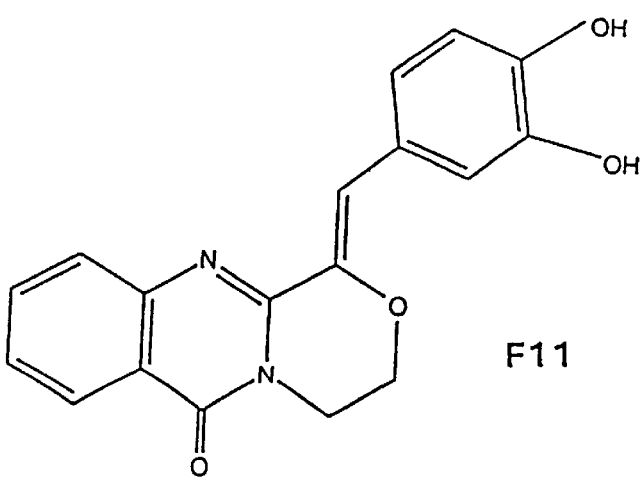
Figure 1F:
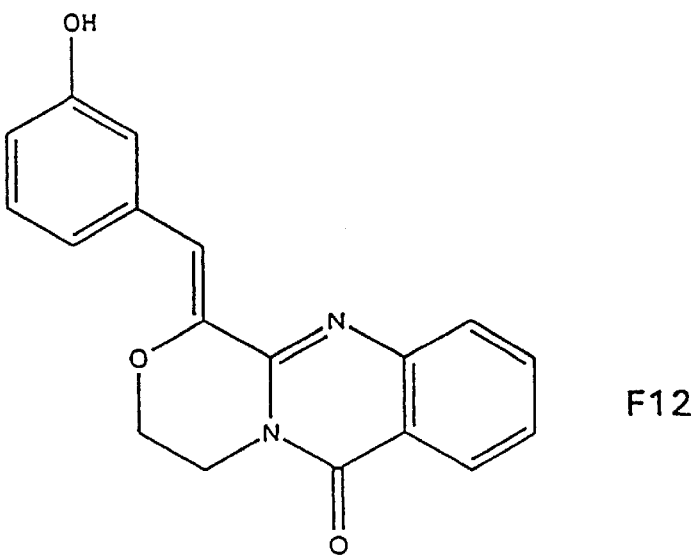

Examples of group 6 compounds are set forth in Table VI and shown in FIG. 1f.

TABLE VI

| Compound | $R_{19}$ | $R_{20}$ |
|---|---|---|
| F10 | $(CH_2)_2OH$ | CH=CH-3,3-dihydroxyphenyl |
| F11 | 2-C=CH-(3,4-dihydroxyphenyl)morpholino | |
| F12 | 1-C=CH-(3-hydroxyphenyl)morpholino | |

G. Group 7 Compounds

Group 7 compounds have the following chemical structure:

where b is an optional pi bond,

Y and Z are independently carbon or nitrogen;

$R_{21}$ and $R_{22}$, are independently hydrogen, halogen, OH, SH, $NH_2$, $NO_2$, alkyl, alkenyl, alkynyl, alkoxy, benzoyl, COOH, or carbalkoxy, preferably OH, $NO_2$, $CH_3$, methoxy, benzoyl, or COOH; or $R_{21}$ and $R_{22}$ together form an aromatic ring to give an aryl, preferably phenyl;

$R_{23}$ is hydrogen, halogen, =O, OH, SH, $NH_2$, alkoxy, COOH, aryl, preferably a substituted or unsubstituted anilino, a substituted or unsubstituted phenyl, hydrogen, COOH, =O, alkoxy, or methoxy, provided that if $R_{23}$ is =O b is present as a bond;

$R_{24}$ is H, or aryl, preferably a substituted or unsubstituted anilino, phenyl, or 2-thienyl; and $R_{25}$ is hydrogen, halogen, =S, or =O, wherein if $R_{25}$ is =O or =S, b is present as a bond; provided that if b is no bond, the adjacent nitrogen optionally has a substituent selected from the consisting of hydrogen, alkyl, alkyleneamino, alkyleneaminoalkly, and alkylenecyano.

Examples of group 7 compounds are set forth in Table VII and shown in FIG. 1g.

TABLE VII

| Compound | b | Y | Z | $R_{21}$ | $R_{22}$ | $R_{23}$ | $R_{24}$ | $R_{25}$ |
|---|---|---|---|---|---|---|---|---|
| G10 | bond | N | C | H | H | H | phenyl | H |
| G11 | bond | C | C | $OCH_3$ | $OCH_3$ | $OCH_3$ | phenyl | Cl |
| G12 | bond | C | C | $OCH_3$ | $OCH_3$ | H | phenyl | Cl |
| G13 | bond | N | C | $CH_3$ | $CH_3$ | H | phenyl | H |
| G14 | bond | N | C | $OCH_3$ | $OCH_3$ | H | phenyl | H |
| G15 | bond | N | C | H | H | H | 2-thienyl | H |
| G16 | bond | N | N | H | H | H | phenyl | H |
| G17 | bond | N | C | OH | $OCH_3$ | H | phenyl | H |
| G18 | no bond | N | C | $CH_3$ | $CH_3$ | =O | phenyl | H |
| G19 | bond | N | C | H | $CH_3$ | H | phenyl | H |
| G20 | bond | N | C | OH | OH | H | phenyl | H |
| G21 | bond | N | C | H | benzoyl | H | phenyl | H |
| G22 | bond | N | C | phenyl | | H | phenyl | H |
| G23 | bond | N | C | H | $NO_2$ | H | phenyl | H |
| G24 | bond | N | C | $CH_3$ | $CH_3$ | 3,4-dyhydroxy-phenyl | phenyl | H |
| G25 | bond | N | C | $CH_3$ | $CH_3$ | COOH | phenyl | H |
| G27 | bond | N | C | $CH_3$ | $CH_3$ | H | $NO_2$ | H |
| G28 | bond | N | C | $CH_3$ | $CH_3$ | H | 3-bromo-phenylamino | H |
| G29 | bond | N | C | $CH_3$ | $CH_3$ | 3-iodo-phenylamino | H | N |
| G30 | bond | N | C | $CH_3$ | $CH_3$ | 4-iodo-phenylamino | H | H |

H. Group 8 Compounds

Group 8 compounds have the following chemical structure:

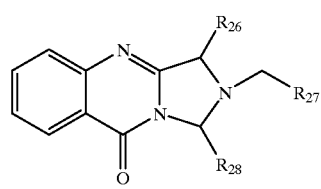

where
R$_{26}$ and R$_{28}$ is independently alkyl, aryl, alkenyl, or alkynyl; and
R$_{27}$ is aryl. Examples of group 8 compounds are set forth in Table VIII and shown in FIG. 1h.

TABLE VIII

| Compound | R$_{25}$ | R$_{27}$ | R$_{28}$ |
|---|---|---|---|
| H10 | CH$_3$ | benzyl | 3,4-dihydroxyphenyl |
| H11 | CH$_3$ | benzyl | 2-hydroxyphenyl |
| H12 | CH$_3$ | benzyl | 3-hydroxyphenyl |
| H13 | CH$_3$ | benzyl | 4-hydroxyphenyl |
| H14 | CH$_3$ | benzyl | 3,4,5-trihydroxyphenyl |

I. Group 9 Compounds

Group 9 compounds have the following chemical structure:

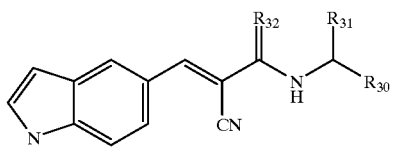

where
R$_{30}$ is either alkyl, alkenyl, or alkynyl, preferably CH$_3$;
R$_{31}$ is aryl, preferably phenyl; and
R$_{32}$ is either O or S.

Figure 1I:
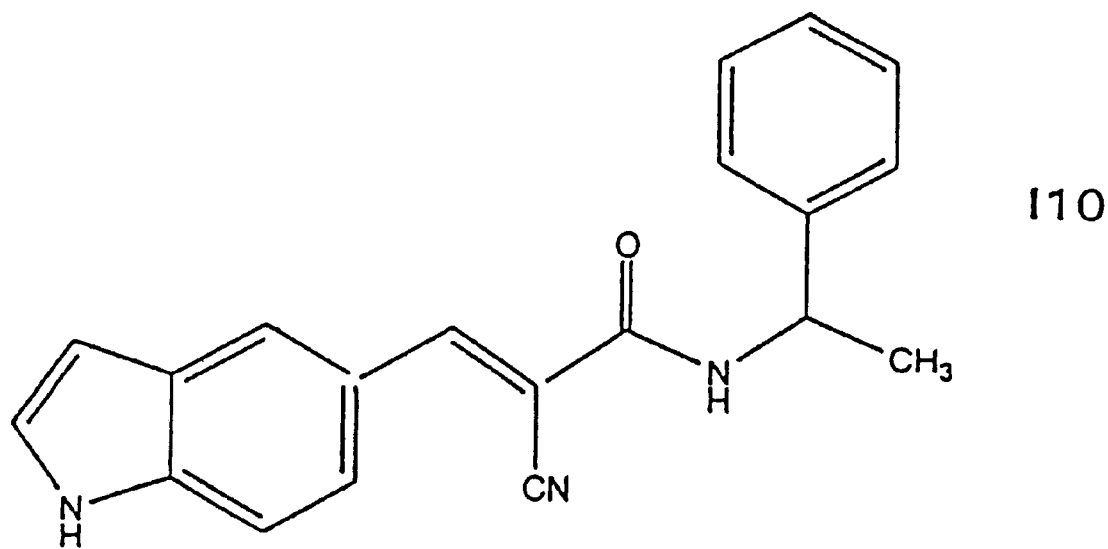

An example of a group 9 compound is I10, shown in FIG. 1i.

J. Group 10 Compounds

Group 9 compounds have the following chemical structure:

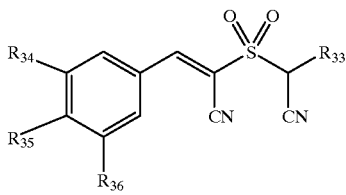

where
R$_{33}$ is alkyl or aryl;
R$_{34}$, R$_{35}$, and R$_{36}$ are independently halogen, OH, hydrogen, alkoxy, SH, NH$_2$, or C(CH$_3$)$_3$, preferably R$_{34}$, R$_{35}$, and R$_{36}$ is independently selected from H, OH, and C(CH$_3$)$_3$.

Figure 1J:
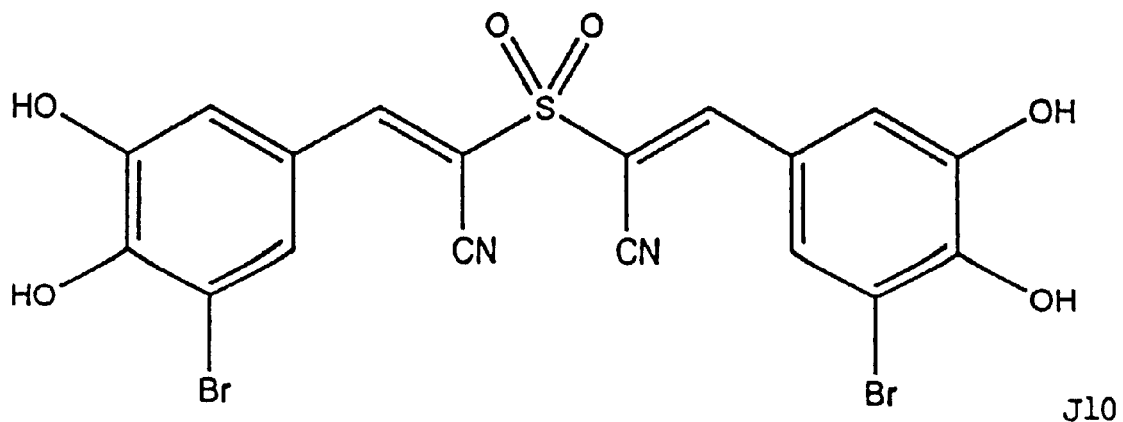
Figure 1J:
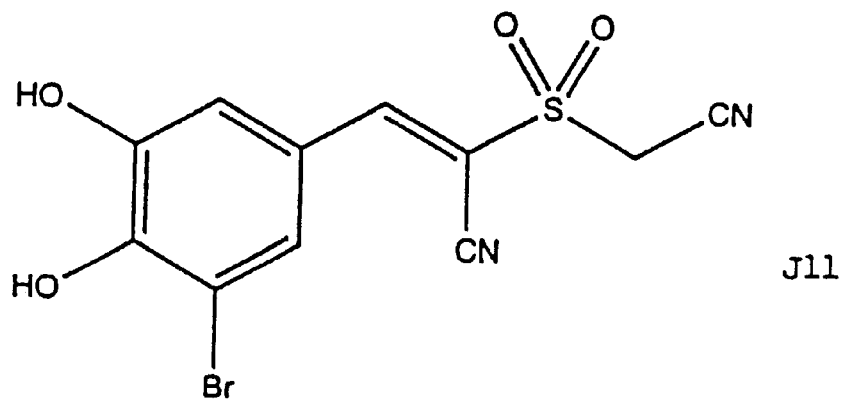

Examples of group 10 compounds are J10 and J11, shown in FIG. 1j.

k. Group 11 Compounds

Figure 1K:
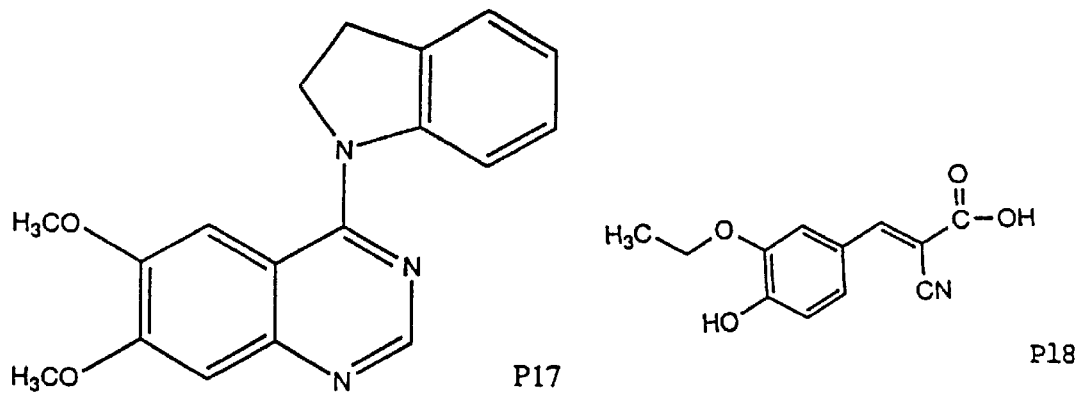
Figure 1:
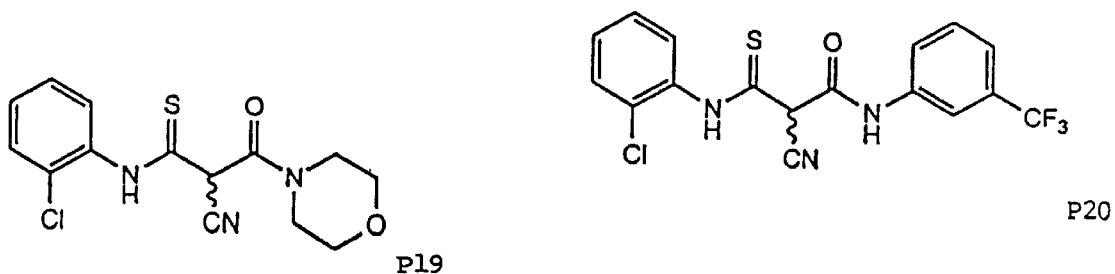
Figure 2:
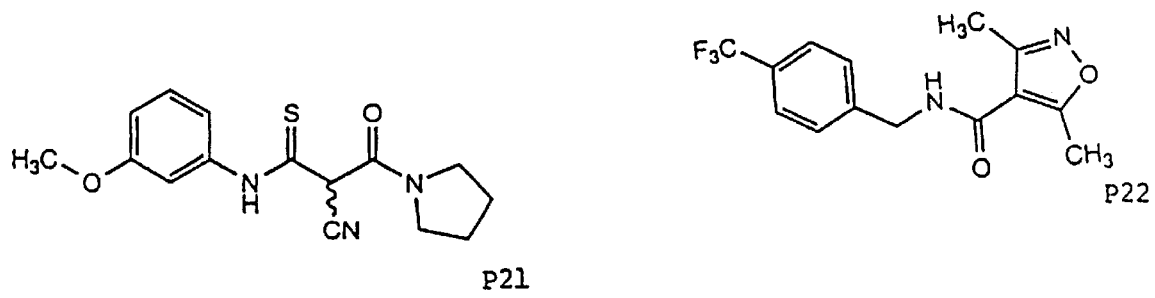
Figure 2A:
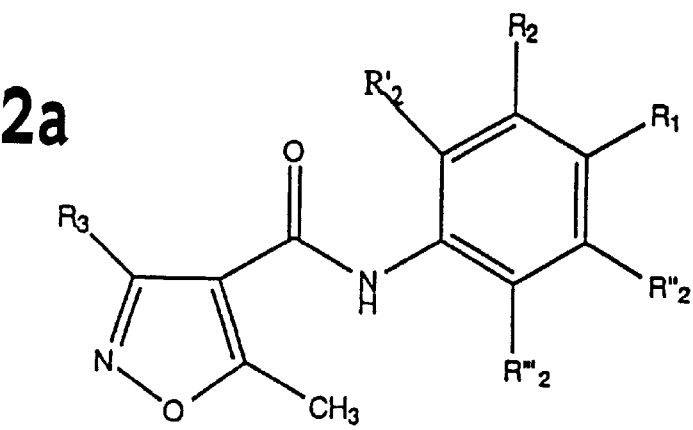
Figure 2B:
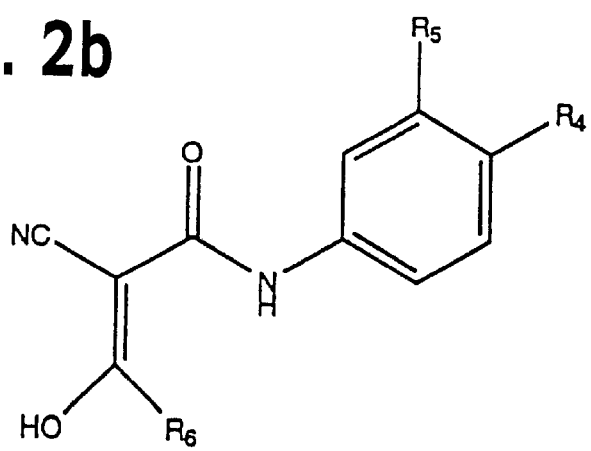
Figure 2C:
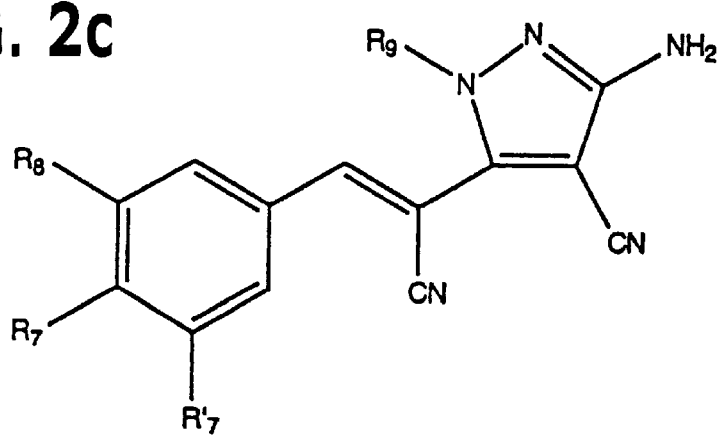
Figure 2D:
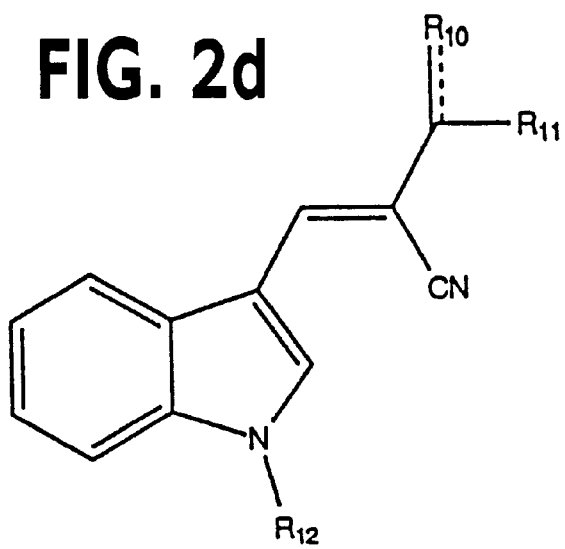
Figure 2E:
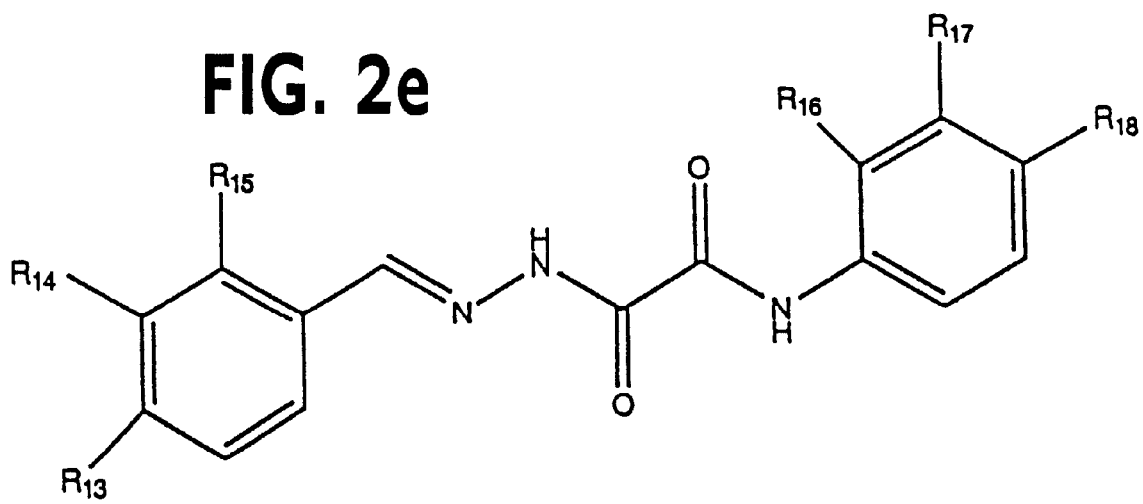
Figure 2F:
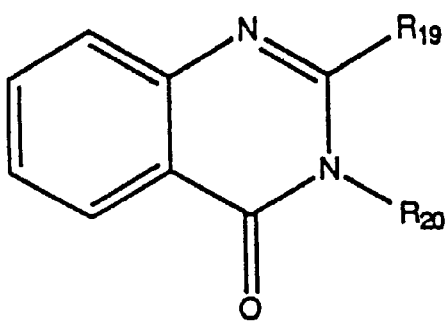
Figure 2G:
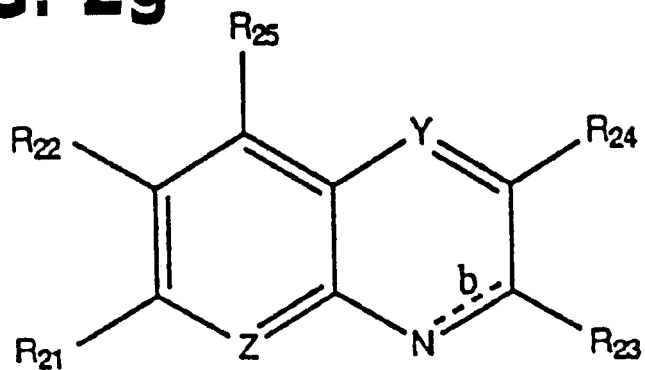
Figure 2H:
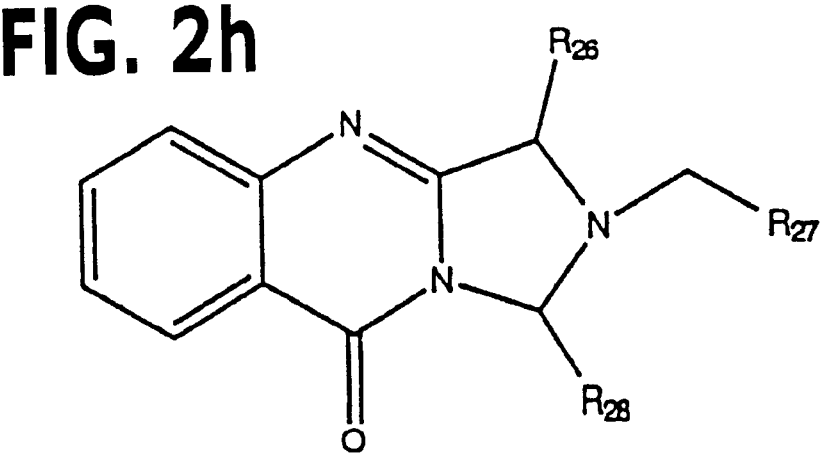
Figure 2I:
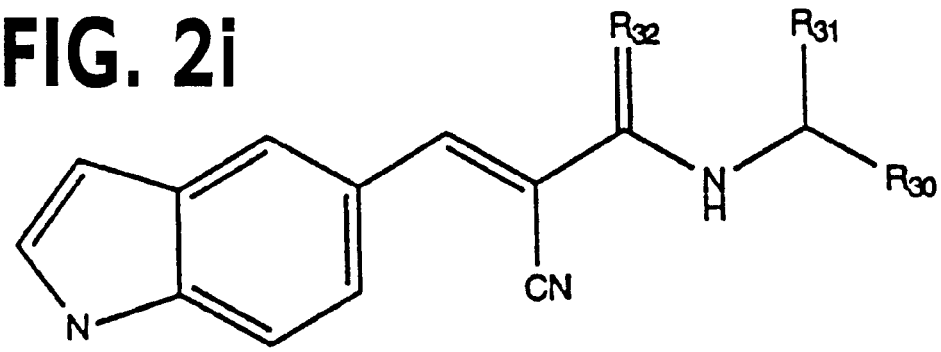
Figure 2J:
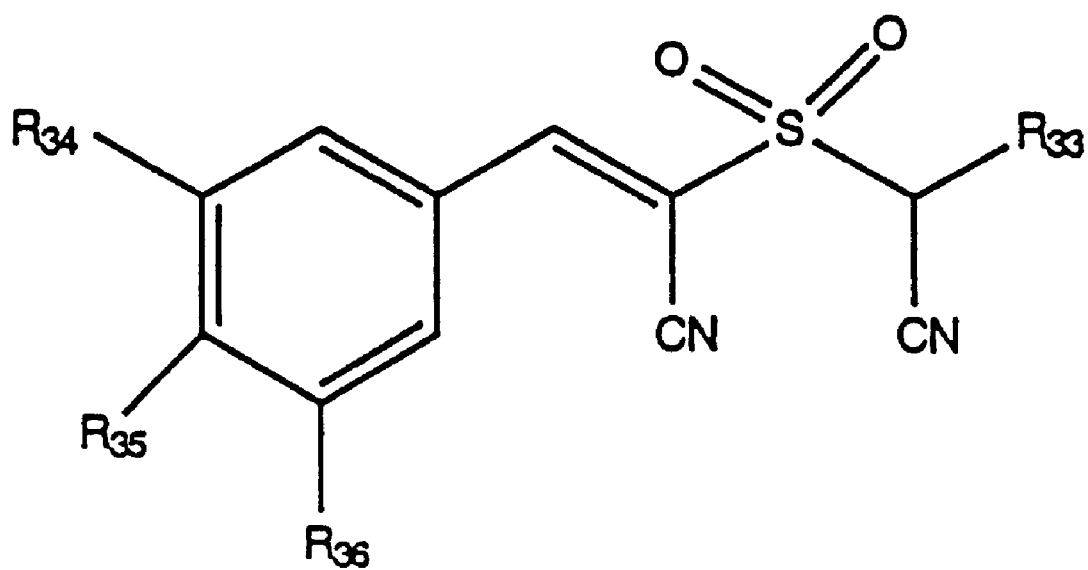

Examples of Group 11 compounds are shown in FIG. 1k. Group 11 compounds are identified by a "P."

l. Chemical Nomenclature

Definitions of some of the chemical groups mentioned in the application are described below.

An "alkyl" group refers to a saturated aliphatic hydrocarbon, including straight-chain, branched-chain, and cyclic alkyl groups. Preferably, the alkyl group has 1 to 12 carbons, more preferably from 3 to 9 carbons. The alkyl group may be substituted or unsubstituted. When substituted the substituted groups are preferably, hydroxyl, cyano, alkoxy, =O, =S, NO$_2$ or N(CH$_3$)$_2$, amino, SH, or aryl.

An "alkenyl" group refers to an unsaturated hydrocarbon group containing at least one carbon-carbon double bond, including straight-chain, branched-chain, and cyclic groups. Preferably, the alkenyl group has 2 to 12 carbons, more preferably from 3 to 9 carbons. The alkenyl group may be substituted or unsubstituted. When substituted the substituted groups are preferably, hydroxyl, cyano, alkoxy, =O, =S, NO$_2$ or N(CH$_3$)$_2$; amino, SH, or aryl.

An "alkynyl" group refers to an unsaturated hydrocarbon group containing at least one carbon-carbon triple bond, including straight-chain, branched-chain, and cyclic groups. Preferably, the alkynyl group has 2 to 12 carbons, more preferably from 3 to 9 carbons. The alkynyl group may be substituted or unsubstituted. When substituted the substituted groups are preferably, hydroxyl, cyano, alkoxy, =O, =S, NO$_2$ or N(CH$_3$)$_2$, amino, SH, or aryl.

An "alkoxy" group refers to an "—O-alkyl" group, where "alkyl" is defined as described above.

An "aryl" group refers to an aromatic group which has at least one ring having conjugated pi electron system and includes carbocyclic aryl, heterocyclic aryl and biaryl groups, all of which may be optionally substituted. The preferred substituents of aryl groups are hydroxyl, cyano, alkoxy, alkyl, alkenyl, alkynyl, amino, and aryl groups.

Carbocyclic aryl groups are groups wherein the ring atoms on the aromatic ring are carbon atoms. The carbon atoms are optionally substituted. Carbocyclic aryl groups include monocyclic carbocyclic aryl groups and optionally substituted naphthyl groups.

Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted.

A "carbalkoxy" group refers to a COOX group, wherein "X" is an lower alkyl group.

The term "lower" referred to herein in connection with organic radicals or compounds respectively defines such with up to and including 7, preferably up to and including 4, and advantageously one or two carbon atoms. Such groups may be straight chain or branched.

II. Cell Proliferative Disorders

The described compositions and methods are designed to inhibit cell proliferative diseases by inhibiting PDGF-R activity. As discussed above, proliferative disorders result in unwanted cell proliferation of one or more subset of cells in a multicellular organism resulting in harm to the organism. Inappropriate PDGF activity can stimulate cell proliferative disorders. Two ways in which inappropriate PDGF or PDGF-R activity can stimulate unwanted cell proliferation of a particular type of cell are by directly stimulating growth of the particular cell, or by increasing vascularization of a particular area, such as tumor tissue, thereby facilitating growth of the tissue.

The use of the present invention is facilitated by first identifying whether the cell proliferation disorder is PDGF-R driven. Once such disorders are identified, patients suffering from such a disorder can be identified by analysis of their symptoms by procedures well known to medical doctors. Such patients can then be treated as described herein.

Determination of whether the cell proliferation disorder is PDGF-R driven can be carried out by first determining the level of PDGF-R activity occurring in the cell or in a particular body location. For example, in the case of cancer cells the level of one or more PDGF-R activities is compared for non-PDGF-R driven cancers (e.g. A431 cells as described below) and PDGF-R driven cancers (e.g., T98G glioblastoma cells as described below). If the cancer cells have a higher level of PDGF-R activity than non-PDGF-R driven cancers, preferably equal to or greater than PDGF-R driven cancers, then they are candidates for treatment using the described PDGF-R inhibitors.

In the case of cell proliferative disorders arising due to unwanted proliferation of non-cancer cells, the level of PDGF-R activity is compared to that level occurring in the general population (e.g., the average level occurring in the general population of people or animals excluding those people or animals suffering from a cell proliferative disorder). If the unwanted cell proliferation disorder is characterized by a higher PDGF-R level then occurring in the general population then the disorder is a candidate for treatment using the described PDGF-R inhibitors.

Cell proliferative disorders include cancers, blood vessel proliferation disorders, and fibrotic disorders. These disorders are not necessarily independent. For example, fibrotic disorders may be related to, or overlap with, blood vessel disorders. For example, atherosclerosis, (which is characterized herein as a blood vessel disorder) results in the abnormal formation of fibrous tissue.

A cancer cell refers to various types of malignant neoplasms, most of which can invade surrounding tissues, and may metastasize to different sites, as defined by Stedman's Medical Dictionary 25th edition (Hensyl ed. 1990). Examples of cancers which may be treated by the present invention include those intra-axial brain cancers, ovarian cancers, colon cancers, prostate cancers, lung cancers, Kaposil's sarcoma and skin cancers, which have inappropriate PDGF-R activity. These types of cancers can be further characterized. For example, intra-axial brain cancers include glioblastoma multiforme, anaplastic astrocytoma, astrocytoma, ependymoma, oligodendroglioma, medulloblastoma, meningioma, sarcoma, hemangioblastoma, and pineal parenchymal.

The formation and spreading of blood vessels, or vasculogenesis and angiogenesis respectively, play important roles in a variety of physiological processes such as embryonic development, wound healing and organ regeneration. They also play a role in cancer development. Blood vessel proliferation disorders refer to angiogenic and vasculogenic disorders generally resulting in abnormal proliferation of blood vessels. Examples of such disorders include restenosis, retinopathies, and atherosclerosis.

The advanced lesions of atherosclerosis result from an excessive inflammatory-proliferative response to an insult to the endothelium and smooth muscle of the artery wall. (Ross R., *Nature* 362:801–809 (1993).) Part of the response appears to be mediated by PDGF-BB secretion, and activation of PDGF-R in endothelial and smooth muscle cells. Both cell migration and cell proliferation play a role in the formation of atherosclerotic lesions.

Fibrotic disorders refer to the abnormal formation of extracellular matrix. Examples of fibrotic disorders include hepatic cirrhosis and mesangial cell proliferative disorders.

Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Inappropriate PDGF-R activity can stimulate lipocyte proliferation.

Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. PDGF has been implicated in the maintenance of mesangial cell proliferation. (Floege, J. et al., *Kidney International* 43S:47–54 (1993).)

As noted above, other such proliferative diseases can be identified by standard techniques, and by determination of the efficacy of action of the compounds described herein.

A. Ovarian Cancer

One aspect of the invention relates to the treatment of ovarian cancer. Epithelial ovarian cancer accounts for nearly 90% of all ovarian tumors and continues to be a highly lethal malignancy. Approximately 19,000 new cases of ovarian cancer are diagnosed in the United States annually, and 12,000 of these women will die from the cancer (Rodriguez et al., in DeVita, Hellman, Rosenberg (eds) *Biologic Therapy of Cancer*, J B Lippincott, 1991).

Treatment for advanced ovarian cancer generally includes cytoreductive surgery followed by combination chemotherapy with alkylating agents such as cisplatin and cyclophosphamide. However, long term survival of advanced ovarian cancer patients is extremely poor, in the range of 10%–20%, principally because of the high incidence of metastatic tumors throughout the peritoneal cavity, and, in some cases, the lymph-nodes. Moreover, chemotherapy with cisplatin carries a potential for renal toxicity and progressive neuropathy.

The invention reveals a pathological relationship between PDGF receptor expression and epithelial ovarian cancer, and provides compositions and methods for inhibiting inappropriate PDGF-R activity in epithelial ovarian cancer cells to inhibit proliferation of the disease. Methods of treating ovarian cancers comprise administering a composition which inhibits inappropriate PDGF-R activity in ovarian carcinoma cells, in supporting stromal cells (i.e., the framework upon which a tumor or metastatic lesion grows, including but not limited to connective tissue and vascular endothelial cells), and/or in associated vascular endothelial cells.

Ovarian cancers susceptible to treatment with the compounds described herein include epithelial ovarian carcinoma, ovarian tumor metastases, and other cells of the ovary which express PDGF receptors. As described below, compositions which inhibit PDGF-R activity also inhibit proliferation of ovarian cancer cells in vitro and inhibit the growth of ovarian tumors in vivo. More specifically, the use of one composition of the invention, A10, results in nearly complete inhibition of ovarian tumor growth in mice xenotransplanted with human ovarian cancer cells, without significant cytotoxicity or mortality, thus providing a dramatic therapeutic effect.

Accordingly, as an example of the method of the invention, A10 is administered to a patient diagnosed with ovarian cancer via any route of administration and in any suitable pharmaceutical carrier which results in bringing A10 in contact with PDGF receptor-positive ovarian cancer cells and/or cells of the surrounding stroma. In view of the localized spread of ovarian cancer throughout the peritoneal cavity, a preferred method of administration, particularly in advanced cases, is by intravenous or intraperitoneal injection of a non-toxic pharmaceutical formulation of A10.

The preparation and use of therapeutically effective compositions for treating ovarian cancers are described in detail in the sections which follow and by way of examples, infra. In addition to the compositions specifically disclosed herein, the invention provides for the identification of other compositions which, because of their inhibitoryeffect on PDGF-R activity may be useful for inhibiting the proliferation of ovarian neoplasms. Candidate compositions may be identified by their ability to inhibit PDGF receptor autophosphorylation using any suitable assay, such as in vitro autophosphorylation inhibition ELISA and tyrosine kinase inhibition assays. Candidate compositions may be evaluated for therapeutic efficacy by testing their capacity to inhibit ovarian cancer cell growth and, ideally, by testing inhibition of xenografted tumors in vivo. The procedures described in the examples, infra, or similar procedures, may be employed for conducting such tests.

B. Glioma

Another aspect of the invention relates to the treatment of primary intra-axial brain tumors of the glioma family, including, but not limited to, astrocytomas and glioblastomas. Glioblastoma multiforme is the most common and most malignant tumor of astrocytic origin in human adults and accounts for more than half of all primary brain tumors (See, for example, *Cecil Textbook of Medicine,* Wyngaarden, Smith, Bennett (eds) WB Saunders, 1992, p. 2220).

Gliomas have the common property of direct invasive involvement of brain tissue, are fundamentally malignant, and are inevitably fatal. Glioblastoma patients have a median survival time of less than one year even when treated aggressively with a combination of surgery, chemotherapy, and radiotherapy. Unfortunately, successful surgical intervention is extremely rare in view of the difficulty or impossibility of defining the microscopic borders of a glioma within normal brain tissue. Similarly, chemotherapy with alkylating agents has met with very little success, and no more than 10% of glioma patients respond significantly. Radiation therapy has demonstrated some value in controlling the growth of gliomas, but often results in substantial neurologic impairment. Therapy with interferon-$\beta$, in combination with radiotherapy and chemotherapy, has met with some success (DeVita, Hellman, Rosenberg (eds) *Biologic Therapy of Cancer,* J B Lippincott, 1991).

The invention reveals a pathological relationship between PDGF receptor expression and glioma, and provides compositions and methods for inhibiting PDGF activity in glioma cells to inhibit proliferation of the disease. Methods of treating gliomas comprise administering a composition which inhibits PDGF-R activity expressed in glioma cells and/or in proximate vascular endothelial cells. In particular, most of the compositions specifically disclosed herein are highly active at inhibiting PDGF receptor autophosphorylation in human glioma cells in vitro. Several of these compositions inhibit the growth of cultured glioma cells, and one of these, A10, also inhibits the growth of various glioma explant cultures. Moreover, A10 strongly suppresses the growth of xenografted gliomas in mice; in some animals, tumor growth was inhibited by greater than 95% relative to untreated controls.

Accordingly, as an example of the method of the invention, A10 is administered to a glioma patient via any route of administration and in any suitable pharmaceutical carrier which will result in bringing A10 in contact with PDGF receptor-positive glioma cells, as well as proximate vascular endothelial cells, which typically proliferate in high grade gliomas. Intravenous and intra-arterial routes may be preferred routes of administration. In addition, recently-developed micro-catheter technology may be particularly effective at delivering the compositions of the invention directly to the site of the glioma, thereby achieving immediate localized contact with the cancer and proximate endothelial cells and possibly minimizing potential toxicity associated with more distal intra-arterial delivery.

The preparation and use of therapeutically effective compositions for the treatment of gliomas are described in detail in the sections which follow and by way of examples, infra. In addition to the compositions specifically disclosed herein, the invention provides for the identification of other compositions which, because of their inhibitory effect on PDGF receptor activity, may be useful for inhibiting the proliferation of various intra-axial tumors. Candidate compositions may be identified by their ability to inhibit PDGF receptor activity using any suitable assay, such as in vitro autophosphorylation inhibition ELISA and tyrosine kinase inhibition assays. Candidate compositions may be evaluated for therapeutic efficacy by testing inhibition of glioma cell growth and, ideally, by testing inhibition of xenografted tumors in vivo.

III. A10

The present invention describes various compositions which can be used to inhibit PDGF-R activity and thereby inhibit cell proliferation disorders. The use of A10 to inhibit tumor growth in animals demonstrates the ability of these compositions to function in vivo despite various pharmacological considerations which are expected to prevent the composition from exerting its effect. Such in vivo inhibition is illustrated in the examples described below.

A10 is also known as leflunomide, HWA 486, and 5-methylisoxazole-4 carboxylic acid-(4-trifluromethyl)-anilide. Various publications have discussed different possibly uses of A10. According to the abstracts of Kömmerer F-J, et al., U.S. Pat. No. 4,284,786 (1981) and Kömmerer F-J, et al., U.S. Pat. No. 4,351,841 (1982), A10 "has antirheumatic, antiphlogistic, antipyretic and analgesic action, and can be used for the treatment of multiple sclerosis." According to Talmadge J. E., and Twardzik D. R. *Agents and Actions* 35S:135–141 (1991), "the hypothesis was suggested that the mechanisms of Leflunomide activity may be the inhibition of a cytokine specific kinase." Robertson S. M. and Lang L. S., European Patent Application 0 413 329 A2 (published 1991) which is concerned with 5-methylisoxazole-4-carboxylic acids that encompass leflunomide, asserts:

The present invention is directed to methods for treating ocular diseases with immune etiology through the use of 5-methyl-isoxazole-4-carboxylic acid anilides and hydroxyethlidene-cyano acetic acid anilide derivatives. In addition the compounds are useful for treating ocular manifestation associated with systemic diseases with immune etiology. The compounds exhibit immunosuppressive, antiinflammatory, and mild antiallergic activity and are useful for the treatment of eye diseases such as uveitis (including rheumatoid nodules), retinitis, allergy (vernal keratocon junctivitis and allergic or giant papillar conjunctivitis) and dry eye (Sjogren's syndrome). Additionally the compounds are useful for prolonging graft survival of corneal or other ocular tissue and are useful as surgical adjuncts in patients which are atopic or immune impaired.

The abstract of Barlett R. R. et al., entitled "Isoxazole-4-Carboxamides and Hydroxyalklidene-Cyanoacetamides, Drugs Containing These Compounds and Use of Such Drugs" PCT/EP90/01800, asserts:

Isoxazole-4-carboxamide derivatives and hydroxyalkylidene-cyanoacetamide derivatives are suitable for the treatment of cancer diseases. These compounds can be prepared by prior art methods. Some of them are new and are suitable, in addition, for the treatment of rheumatic diseases.

Bartlett R. R. et al., *Agents and Actions* 32:10–21 (1991), asserts that "[l]eflunomide has been shown to be very effective in preventing and curing several autoimmune animal diseases." Barlett also asserts that:

> . . . , we could show that tyrosine phosphorylation of the RR-SRC peptide substrate and the autophosphorylation of the epidermal growth factor (EGF) receptor were, dose dependently, inhibited by leflunomide.

Figure 3A:
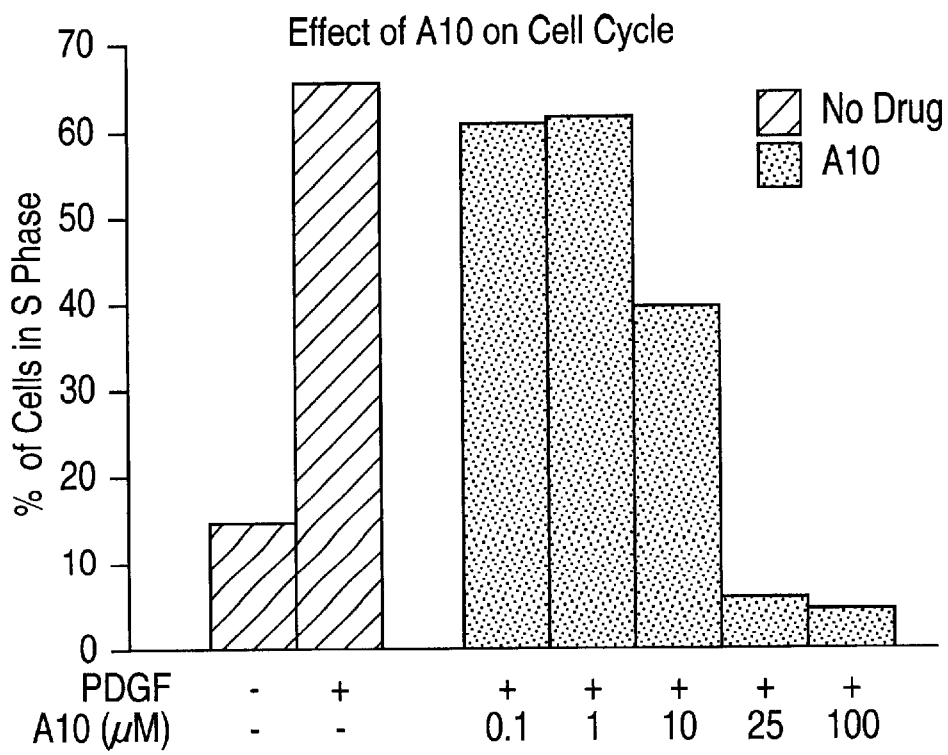
FIG. 3. NIH3T3 cells overexpressing the human PDGF-b (A) or the human EGF (B) receptor were treated with A10 as indicated. The percentage of cells in the S phase of the cell cycle was determined by flow cytometry.
Figure 3B:
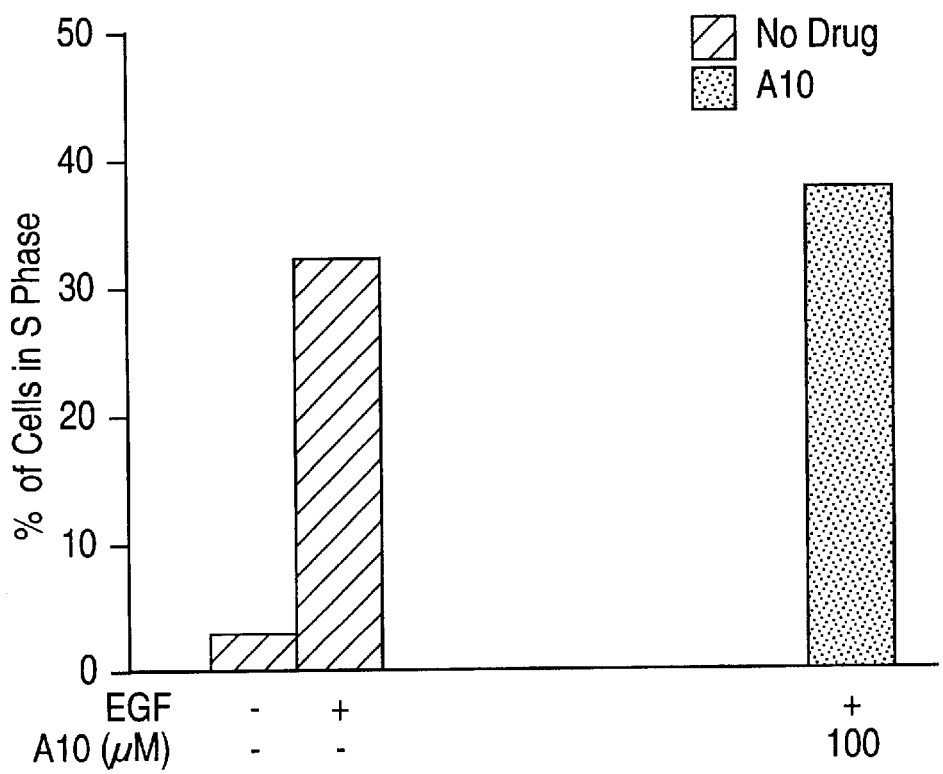

Matter et al., *FEBS* 334:161–164 (Nov. 1993) (not admitted to be prior art) describes the use of the active metabolite of leflunomide to inhibit EGF-dependent cell growth, including A431 cells. Matter also asserts:

> Platelet-derived growth factor-dependent tyrosine phosphorylation was also inhibited by A77 1726 in intact cells at concentrations similar to EGF-dependent phosphorylation described in FIG. 3 (data not shown).

Studies on one composition of the invention, A10, described more fully and by way of example infra, establish its potency against brain, lung, prostate, ovarian, skin, and colon cancer cells characterized by inappropriate PDGF-R activity rather than EGF activity. As illustrated in the examples described below A10 inhibits PDGF-R activity while having little if any effect on EGF-receptor or HER2 phosphorylation. In addition, while A10 inhibited growth of tumors characterized by inappropriate PDGF-R activity, A10 did not significantly inhibit the growth of xenotransplanted cells expressing EGF receptor (A431 epidermoid cells). This data is surprising in view of the results described by Bartlett et al., supra, *Agents and Actions* in which leflunomide was shown to inhibit EGF induced EGF receptor autophosphorylation and cell proliferation, and Matter et al., supra, in which the active metabolite of leflunomide inhibited growth of A431 cells.

The present disclosure demonstrates the ability of A10 to inhibit inappropriate PDGF-R activity and unwanted cell proliferation in vivo, such as occurs in cancers characterized by inappropriate PDGF-R activity. As illustrated by the examples described below, A10 can be used to selectively inhibit inappropriate PDGF-R activity.

A compound is judged to effect phosphorylation if its ability to inhibit phosphorylation of a receptor (e.g., the $IC_{50}$ as described below) is less than its cytotoxic effect (e.g., the $LD_{50}$ as described below). Inhibition of phosphorylation of different receptors such as PDGF-R, EGF-R or HER2 receptor is dependent on conditions such as drug concentration. By "selectively inhibit" it is meant that a compound can be used at a particular concentration to inhibit phosphorylation of the PDGF-R and have little if any effect on the phosphorylation of the EGF-R and/or HER2 receptor at the same concentration.

Preferably, the compound, like A10 can inhibit PDGF-R while having little if any effect on EGF-R and/or HER2 phosphorylation. By "little if any effect" on EGF-R, or HER2, activity is meant the receptor activity is effected no more than 35%, more preferably, no more than 20%, most preferably no more than 10%, at a particular receptor.

Tyrosine kinases are important in many biological processes including cell growth, differentiation, aggregation, chemotaxis, cytokine release, and muscle contraction. Many of these events are mediated through different tyrosine kinase receptors. In addition, different tyrosine kinase receptors may be important for a particular biological function in different cell types. By developing selective inhibitors of PDGF-R the possible toxic effect of the compound is decreased.

The compounds described herein vary in their ability to selectively inhibit PDGF-R. For example D14, G12, G13 and G14 inhibit PDGF-R phosphorylation but do not effect EGF or HER2 phosphorylation; while C10 effects EGF-4, PDGF-R, and HER2 phosphorylation.

IV. Mutated PDGF-R

Cell proliferative disorders characterized by inappropriate PDGF-R activity can also be inhibited using a mutated PDGF-R. Ueno H., et al., *Science* 252:844–252 (1991), describe nucleic acid encoding truncated PDGF-R to inhibit PDGF-R phosphorylation in vitro. According to Ueno:

> When truncated receptors were expressed in excess compared to wild-type receptors, stimulation by PDGF of receptor autophosphorylation, association of phosphatidylinositol-3 kinase with the receptor, and calcium mobilization were blocked.

Ueno did not demonstrate that inhibition of PDGF-R activity by a mutated protein could inhibit unwanted cell proliferation.

Such in vivo inhibition of unwanted cell proliferation is illustrated in the examples described below using nucleic acid encoding the PDGF-R having a stop codon just upstream from the first tyrosine kinase domain. The nucleic acid is used to introduce the truncated protein into a cell. For example, the nucleic acid encoding a truncated PDGF-R is placed into a retroviral vector using standard recombinant DNA techniques. The vector then infects a cell where its nucleic acid is ultimately translated into protein producing a truncated PDGF-R. Other means of introducing the mutated protein into a cell include preparing the mutated protein in vitro and introducing the protein into the cell with a vector, such as a liposome.

Mutant PDGF-R should be constructed to interfere with intermolecular phosphorylation that occurs between dimerized receptor. This can be accomplished by various means such as 1) truncation of the PDGF-R, preferably to eliminate one tyrosine kinase domain, and most preferably to eliminate both tyrosine kinase domains; and 2) mutations which inhibit the catalytic ability of the PDGF-R catalytic domain, such as mutation of lysine 602 to arginine which prevents the binding of ATP. Of these methods, mutation of tyrosine residues is preferred and truncation of the receptor is most preferred.

The use of nucleic acid encoding truncated PDGF-R to inhibit tumor growth in animals demonstrates the ability of such truncated receptors to function in vivo despite various pharmacological considerations which would be expected to prevent the composition from exerting its effect. Thus, the present disclosure demonstrates that the use of nucleic acid encoding truncated PDGF receptor is not limited to inhibition of PDGF-R in cell culture. Rather nucleic acid encoding PDGF-R can be used to inhibit inappropriate PDGF-R activity in animal cells thereby inhibiting the growth of tumors in animal cells, and having application in other PDGF-R related disorders.

V. Administration of Featured Compounds

The compounds of this invention can be administered to a patient alone, or in a pharmaceutical composition comprising the active compound and a carrier or excipient. The compounds can be prepared as pharmaceutically acceptable salts (i.e., non-toxic salts which do not prevent the compound from exerting its effect).

Pharmaceutically acceptable salts can be acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. (See e.g., supra. PCT/US92/03736); Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In a another example, the salt is prepared by reacting the free base and acid in an organic solvent.

Carriers or excipient can be used to facilitate administration of the compound, for example, to increase the solubility of the compound. Examples of carriers and excipient include calcium carbonate, calcium phosphate, various sugars or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmuccosally.

Several of the featured compounds, such as A10 and B11, are hydrophobic and thus not very soluble in water. Effective doses of A10 can be obtained by using A10 in combination with PBTE:D5W. PBTE consists of a solution of 3% w/v benzyl alcohol, 8% w/v polysorbate 80, and 65% w/v polyethylene glycol (MW=300 daltons) in absolute ethanol. PBTE:D5W consists of PBTE diluted 1:1 in a solution of 5% dextrose in water. The solubility of A10 in PBTE is about 60 mg/ml, and the solubility of A10 in PBTE:D5W is about 5 mg/ml. The solubility of the other compounds described herein can be obtained using standard techniques. In addition, the active drug itself (e.g., B11) may be administered in an oral formulation.

Another way of overcoming the hydrophobicity problem includes the use of frequent small daily doses rather than a few large daily doses. For example, the composition can be administered at short time intervals, preferably the composition can be administered using a pump to control the time interval or achieve continuously administration. Suitable pumps are commercially available (e.g., the ALZET® pump sold by Alza corporation, and the BARD ambulatory PCA pump sold by Bard MedSystems).

Alternatively, prodrugs having increased solubility can be used. Prodrugs can break down into the active drug under physiological conditions. For example, Patterson et al., *J. Med. Chem.* 35:507–510 (1992), describes A12 (3-carboxy-5-methyl-N-[4(triflouromethyl)phenyl]-4-isoxazolecarboxamide) which, like A10, can act as a prodrug for B11.

The proper dosage depends on various factors such as the type of disease being treated, the particular composition being used, and the size and physiological condition of the patient. For the treatment of cancers the expected daily dose of A10 is between 1 to 2000 mg/day, preferably 1 to 250 mg/day, and most preferably 10 to 150 mg/day. Drugs can be delivered less frequently provided plasma levels of the active moiety are sufficient to maintain therapeutic effectiveness.

A factor which can influence the drug dose is body weight. Drugs should be administered at doses ranging from 0.02 to 25 mg/kg/day, preferably 0.02 to 15 mg/kg/day, most preferably 0.2 to 15 mg/kg/day. Alternatively, drugs can be administered at 0.5 to 1200 mg/m$^2$/day, preferably 0.5 to 150 mg/m$^2$/day, most preferably 5 to 100 mg/m$^2$/day. The average plasma level should be 50 to 5000 mg/ml, preferably 50 to 1000 mg/ml, and most preferably 100 to 500 mg/ml. Plasma levels may be reduced if pharmacologically effective concentrations of the drug are achieved at the site of interest.

VI. Administration of Mutated PDGF-R

The PDGF-R mutants can be administered as nucleic acid expressing the protein, using standard techniques some of which are discussed below. Delivery vehicles include liposomes and other pharmaceutical compositions. Nucleic acid encoding a mutated PDGF-R can also be introduced into a cell using standard techniques such as a retroviral and ion paired molecules. In those cases where the technique is carried out ex vivo the cell is then put into a patient. Administration of protein is facilitated using a carrier or excipient as described above.

The specific delivery route of any selected agent depends on the use of the agent (such considerations are also applicable for the administration of the featured compounds). Generally, a specific delivery program for each agent focuses on agent uptake with regard to intracellular localization, followed by demonstration of efficacy. Alternatively, delivery to these same cells in an organ or tissue of an animal can be pursued. Uptake studies include uptake assays to evaluate, e.g., cellular nucleic acid or protein uptake, regardless of the delivery vehicle or strategy. Such assays also determine the intracellular localization of the agent following uptake, ultimately establishing the requirements for maintenance of steady-state concentrations within the cellular compartment containing the target sequence (nucleus and/or cytoplasm). Efficacy and cytotoxicity can then be tested. Toxicity not only includes cell viability but also cell function. Generally, the dosages of the mutated protein and nucleic acid is as described above for the featured compounds.

Drug delivery vehicles are effective for both systemic and topical administration. They can be designed to serve as a slow is release reservoir, or to deliver their contents directly to the target cell. An advantage of using direct delivery drug vehicles is that multiple molecules are delivered per uptake. Such vehicles increase the circulation half-life of drugs which would otherwise be rapidly cleared from the blood stream. Some examples of such specialized drug delivery vehicles falling into this category are liposomes, hydrogels, cyclodextrins, biodegradable nanocapsules, and bioadhesive microspheres. Pumps can also be used for this purpose.

From this category of delivery systems, liposomes are preferred. Liposomes increase intracellular stability, increase uptake efficiency and improve biological activity. Liposomes are hollow spherical vesicles composed of lipids arranged in a similar fashion as those lipids making up the cell membrane. They have an internal aqueous space for entrapping water soluble compounds and range in size from 0.05 to several microns in diameter. Antibodies can be attached to liposomes to target particular cells.

Topical administration of PDGF-R mutants and the featured compounds is advantageous since it allows localized concentration at the site of administration with minimal systemic absorption. This simplifies the delivery strategy of the agent to the disease site and reduces the extent of toxicological characterization. Furthermore, the amount of material applied is far less than that required for other administration routes. Effective delivery requires nucleic acid to enter the cell membrane or the cytoplasm of cells characterized by inappropriate PDGF-R activity and express the protein.

Agents may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the drug to an accessible diseased tissue. Subcutaneous administration drains into a localized lymph node which proceeds through the lymphatic network into the circulation. The rate of entry into the circulation has been shown to be a function of molecular weight or size.

VII. EXAMPLES

Examples are provided below to illustrate different aspects and embodiments of the present invention. These examples are not intended in any way to limit the disclosed invention. Rather, they illustrate methodology by which drugs having the disclosed formula can be readily identified by routine procedure to ensure that they have the desired activity. That is, compounds within the formula claimed herein can be screened to determine those with the most appropriate activity prior to administration to an animal or human. Other compounds can also be screened to determine suitability for use in methods of this invention.

A description of some of the procedures used in the following examples is described in the appendices below. The use of A10 in the different procedures is mentioned, however, compounds other than A10 were tested by these procedures by replacing A10 with the tested compound.

Appendix 1

1. Cell Lines

Cell lines were purchased from the ATCC unless otherwise specified. U1240 and U1242 cells were obtained from Dr. Joseph Schlessinger (New York University) and SF763 and SF767 cells were obtained from Dr. Michael Berens (Barrow Neurological Institute).

SF767T, SF763T, U118T, and SKOV3T are sublines of SF767, SF763, U118 and SKOV3 cells, respectively. They were derived by implanting the parental cells SC into BALB/c, nu/nu mice. Tumors which displayed desirable growth characteristics were resected and finely minced in a sterile petri dish. Two to five mL of appropriate medium was added to the slurry and the tumor pieces were further mechanically teased apart. The resulting suspension was placed into tissue culture flasks and fed with the appropriate culture medium supplemented with 100 unit/mL penicillin G sodium and 100 µg/mL streptomycin sulfate (Gibco, Grand Island, N.Y.). Medium was changed every two to three days. After three to five passages, the antibiotic supplements were removed and the cells maintained in antibiotic-free medium.

NIH3T3 mouse fibroblasts overexpressing the EGF receptor, Flk-1, IGF-1 receptor or PDGF-β receptor were engineered using retroviral vectors. MCF7/HER2 cells were derived by overexpressing the HER2 gene using retroviral constructs in an MCF7 background.

2. Cell Culture

All cell culture media, glutamine, and fetal bovine serum were purchased from Gibco Life Technologies (Grand Island, N.Y.) unless otherwise specified. All cells were grown in a humid atmosphere of 90–95% air and 5–10% $CO_2$ at 37° C. All cell lines were routinely subcultured twice a week and were negative for mycoplasma as determined by the Mycotect method (Gibco).

C6 cells were maintained in Ham's F10 supplemented with 5% fetal bovine serum (FBS) and 2 mM glutamine (GLN). T98G cells were cultured in MEM with 10% FBS, 2 mM GLN, 1 mM sodium pyruvate (NaPyr) and non-essential amino acids (NEAA). SKOV3T cells were cultured in DMEM, 10% FBS and 2 mM GLN.

NIH3T3 mouse fibroblasts engineered to overexpress Flk-l or the EGF receptor were maintained in DMEM containing 10% calf serum (CS) and 2 mM GLN. NIH3T3 cells. engineered to overexpress the IGF-l or insulin receptor were maintained in DMEM containing 10% FBS and 2 mM GLN. HL60 cells were maintained in RPMI 1640 with 10% FBS and 2 mM GLN. T47D and BT474 cells were maintained in RPMI 1640 with 10% FBS, GMS-G and 2 mM GLN.

DU 145 cells were grown in DMEM F12 with 10% FBS and 2 mM GLN. A172, A431, U118MG and RAG cells were grown in DMEM with 10% FBS and 2 mM GLN. L1210 cells were grown in DMEM with 10% horse serum and 2 mM GLN. C1300 cells were grown in DMEM with 10% heat inactivated FBS, 2 mM GLN and 50 mM β-mercaptoethanol. T98G, U138MG, U87MG, U373MG, U1240, U1242, Calu-3, Calu-6, SF767, SF767T, SF763, SF763T, SK-N-MC and SK-N-SH cells were grown in MEM with 10% FBS, NEAA, 1 mM NaPyr and 2 mM GLN. MDA MB 361 and MDA MB 468 cells were grown in L15 with 10% FBS and 2 mM GLN. PC-3 cells were grown in HAM'S F12 with 7% FBS and 2 mM GLN. A549 cells were grown in HAM'S F12 with 10% FBS and 2 mM GLN. ZR75-30 cells were grown in RPMI 1640 with 10% FBS, 2 mM GLN and 1 mM NaPyr. MCF7, MCF7/HER2, A375, BT549, 9L, C81-61, ZR 75-1 and K562 cells were grown in RPMI 1640 with 10% FBS and 2 mN GLN. Ovcar3 cells were grown in RPMI 1640 with 20% FBS, 2 mM GLN and 10 mg/mL insulin. D1B and T27A cells were grown in RPMI 1640 with 10% heat-inactivated FBS, 2 mM GLN and 50 mM β-mercaptoethanol; 7TD1 cells were grown in the same medium supplemented with 50 units/mL of recombinant murine IL-6. Colo 320DM, WEHI-164.13, and HBL100 cells were grown in RPMI 1640 with 10% heat-inactivated FBS and 2 mM GLN. SKBR3 cells were grown in McCoy's 5A with 15% FBS and 2 mM GLN. PA-1 cells were grown in MEM with 10% heat-inactivated FBS, 2 mM GLN and NEAA. Neuro 2A cells were grown in MEM with 10% heat inactivated FBS, 2 mM GLN, NEAA, NaPyr and 50 mM β-mercaptoethanol.

Appendix 2

1. Receptor Phosphorylation

The inhibition of receptor tyrosine kinase activity by A10 was studied by western blot and ELISA procedures. For western blotting, cells were plated in 2 mL growth medium into 6-well dishes (500,000 cells per well) and allowed to attach overnight. The medium was replaced with 2 mL MCDB 105 (UCSF Cell Culture Facility) supplemented with 1% FBS. The plates were then incubated overnight at 37° C., ambient $CO_2$. To test the effects of compounds on ligand-mediated receptor autophosphorylation, cells were exposed to A10 or DMSO for 1 hr at 37° C. before the stimulation of receptor tyrosine kinase activity with ligand. After a 7 min incubation at room temperature with ligand, the plates were put on ice and washed three times with 1 mL ice-cold PBS plus 1 mM orthovanadate. Lysis was achieved by pipetting cells in 0.5 mL of buffer containing 50 mM Tris, pH 7.4, 10% glycerol, 1% NP-40, 2 mM EDTA, 1 mM sodium vanadate ($Na_3VO_4$), 10 mM pyrophosphate, 1 mM PMSF, 10 mg/mL aprotinin, 10 mg/mL leupeptin. A 300 µL aliquot of each lysate was immediately added to 100 µL 4×Laemmli sample buffer (0.2 mM Tris pH 6.9, 20% glycerol, 7% SDS, 5 mM EDTA, 5% β-mercaptoethanol) containing phosphatase inhibitors, 2 mM $Na_3VO_4$ and 10 mM pyrophosphate. Samples were boiled for 5 min, frozen in dry ice-ethanol, and stored at −80° C. Proteins were resolved by SDS-PAGE (Bio-Rad Miniprotean II) and transferred to nitrocellulose membrane (Schleicher & Schuell) at 120 volts for 1 hr at room temperature in buffer containing 25 mM Tris pH 8.3, 20% methanol, 0.2 M glycine, 0.1% SDS. The integrity of the protein-to-membrane transfer was determined by staining with 1% Ponceau S in 5% acetic acid for 5 min. After destaining in several distilled water rinses, the membrane was soaked overnight in blocking buffer containing 5% milk in Tris-buffered saline, 0.05% Tween 20. Phosphotyresine was detected by incubating the membrane (1 hr at room temperature) with an anti-phosphotyosine antiserum diluted in blocking buffer at 1:3000. For C6 cells, PDGF-β receptor content in the lysates was confirmed in duplicate sample lanes by western blotting using an antibody specific for PDGF-β receptor (UBI). The antibodies were visualized using ECL reagent from Amersham and by exposure to Fuji RX film.

For ELISA assays, cells were grown to 80–90% confluency in growth medium and seeded in 96-well tissue culture plates in 0.5% serum at 25,000 to 30,000 cells per well. After overnight incubation in 0.5% serum-containing medium, cells were changed to serum-free medium and treated with test compound for 2 hr in a 5% $CO_2$, 37° C. incubator. Cells were then stimulated with ligand for 5–10 min followed by lysis with HNTG (20 mM Hepes, 150 mM NaCl, 10% glycerol, 5 mM EDTA, 5 mM $Na_3VO_4$ 0.2% Triton X-100, and 2 mM NaPyr). Cell lysates (0.5 mg/well in PBS) were transferred to ELISA plates previously coated with receptor-specific antibody and which had been blocked with 5% milk in TBST (50 mM Tris-HCl pH 7.2, 150 mM NaCl and 0.1% Triton X-100) at room temperature for 30 min. Lysates were incubated with shaking for 1 hr at room temperature. The plates were washed with TBST four times and then incubated with polyclonol anti-phosphotyrosine antibody at room temperature for 30 min. Excess anti-phosphotyrosine antibody was removed by rinsing the plate with TBST four times. Goat anti-rabbit IgG antibody was added to the ELISA plate for 30 min at room temperature followed by rinsing with TBST four more times. ABTS (100 mM citric acid, 250 mM $Na_2HPO_4$ and 0.5 mg/mL 2.2'-azino-bis(3-ethylbenzthiazoline-6-sulfonic acid) plus $H_2O_2$ (1.2 mL 30% $H_2O_2$ to 10 mL ABTS) was added to the ELISA plates to start color development. Absorbance at 410 nm with a reference wavelength of 630 nm was recorded about 15 to 30 min after ABTS addition. Cell lines used in ELISA assays included U1242 (PDGF-β receptor), HL-60 cells (GMCSF receptor/JAKI2), or NIH3T3 cells overexpressing the EGF receptor. Flk-1 TGF-1 receptor or the insulin receptor. $IC_{50}$ values were estimated by comparing drug inhibition of tyrosine phosphorylation in the absence or presence of appropriate ligand.

2. DNA Synthesis

The effects of A10 on PDGF-dependent DNA synthesis was determined by measuring the $^3$H-thymidine incorporation into DNA of cells. The conditions for the assay were essentially those described by Pollack, et al. *J. Neurosurg.,* 73:106–112, 1990, with some modifications. T98G cells in log phase growth were transferred to 96-well dishes at 20,000 cells in 200 μL of serum-containing growth medium. After an overnight attachment period, the monolayers were washed twice with 200 μL MCDB 105 medium and the cells were cultured in 200 μL serum-free MCDB 105 medium for 24 hr. Medium in wells was replaced with fresh medium alone (MCDB 105 plus 5 μg/mL insulin), medium containing PDGF-BB alone, or medium containing PDGF-BB in combination with various concentrations of A10. The plates were incubated at 37° C. at ambient $CO_2$ for approximately 18 hr. $^3$H-thymidine (Amersham, 5 Ci/mmol) was added to each well to yield a final concentration of 5 μCi/mL and the plates were returned to 37° C. incubator. After 4 hr the medium was removed, the plates were put onto ice, and washed twice with 200 μL ice-cold PBS per well. Radioactivity incorporated into DNA was separated from unincorporated $^3$H-thymidine by precipitation with 100 μL ice-cold TCA for 10 min on ice. After two washes with ice-cold TCA, the precipitate was solubilized (1% SDS in 100 mL 10 mM Tris base) and transferred to liquid scintillation counting vials. Six mL of cocktail (Ready Safe, Beckman) was added and radioactivity quantified in a Beckman liquid scintillation counter model LS6000SC.

3. Cell Cycle Analysis

NIH3T3 mouse fibroblasts overexpressing the human PDGF-β receptor were seeded in DMEM supplemented with 10% CS and 2 mM GLN. Cells were grown to about 80% confluence and then treated overnight in serum-free medium (DMEM, 2 mM GLN, 2 mM NEAA, 2 mM NaPyr, and 2 mM HEPES). The cells were incubated for 20 hr in the presence of PDGF-BB at 100 ng/mL and with various concentrations of A10(0.1, 1, 10, 25, or 100 mM). Cells were then collected, strained and analyzed by flow cytometry for DNA content.

4. Growth Assays

A10 was tested for inhibition of anchorage-dependent tumor cell growth using the colorimetric assay described by Skehan, et al., *J. Natl. Cancer Inst.,* 82:1107–1112, 1990. The assay measures protein content of acid-fixed cells using the counterion binding dye sulforhodamine B (SRB, Sigma). A10 was solubilized in DMSO (Sigma, cell culture grade) and diluted into appropriate growth medium at two-fold the desired final assay concentration. In assays using C6 cells, A10 (100 μL) was added to 96-well plates containing attached cellular monolayers (2000 cells/well in 100 μL). For other cell lines, the cells (2000 cells/well in 100 μL) were introduced into wells immediately after dispensing the drug solutions. After 4 days (37° C., 5% $CO_2$) the monolayers were washed 3 times with PBS and fixed with 200 μL ice-cold 10% TCA (Fisher Scientific), and kept at 4° C. for 60 min. The TCA was removed and the fixed monolayers were washed 5 times with tap water and allowed to dry completely at room temperature on absorbent paper. The cellular protein was stained for 10 min with 100 μL 0.4% SRB dissolved in 1% acetic acid. After 5 washes with tap water, the dye was solubilized in 10 mM Tris base (100 μL per well) and absorbance read at 570 nm on a Dynatech plate reader model MR5000. Growth inhibition data are expressed as a percentage of absorbance detected in control wells which were treated with 0.4% DMSO alone. DMSO controls were not different from cells grown in regular growth medium. $IC_{50}$ values were determined using a four parameter curve fit function.

For the anchorage-independent tumor cell growth assay, cells (3000 to 5000 per dish) suspended in 0.4% agarose in assay medium (DMEM containing 10% FCS) with and without A10 were plated into 35 mm dishes coated with a solidified agarose base layer (0.8% agarose). After a 2 to 3 week incubation at 37° C., colonies larger than 50 μm were quantified using an Omnicon 3800 Tumor Colony counter.

Appendix 3

1. Growth Assays for Tumor Cell Lines

For most tumor cell lines, inhibition of cell growth by A10 was assessed using an SRB assay as described in Appendix 2. For K562, DlB, L1210, 7TDl, T27A, and Colo320 DM cells, an MTT assay was used to assess cell growth. (Hansen et al., *J. Immunol. Methods,* 119:203–210, 1989.) Briefly, 50 mL of growth medium containing various concentrations of A10 and 50 mL of cell suspension (2,000 cells) were added to each well of a 96-well plate. The cells were incubated at 37° C. for 4 days in a humidified 7% $CO_2$ atmosphere. At the end point, 15 mL of MTT (5 mg/mL in PBS, Sigma) was added to each well. The plates were incubated at 37° C. for 4 hr followed by addition of 100 mL of solubilization solution (20% w/v of SDS in 50% N, N-dimethylformamide, pH 4.7) to each well. The plates were incubated overnight in a sealed container with a humidified atmosphere. The absorbance was determined at 570 nm wavelength with a reference wavelength of 630 nm using an ELISA plate reader.

2. Growth Assay for Primary Tumors

The effect of A10 on primary tumor growth was examined by Oncotech, Inc. (Irvine, Calif.). Viable tumors were placed into medium by the pathologist at the referring institution immediately after surgery, and shipped to Oncotech by overnight delivery. As soon as a tumor was received, a portion was fixed in formalin for sectioning and the remainder trimmed of necrotic, connective and adipose tissues. All tumor manipulations were performed aseptically. The remaining tumor was placed into a Petri dish containing 5 mL of medium (RPMI 1640 supplemented with 10% FBS, 100 IU/mL penicillin, 100 mg/mL streptomycin and L-glutamine) and disaggregated mechanically with scissors into pieces 2 mm or smaller. The resultant slurries were mixed with medium containing 0.003% DNase (2650 Kunitz units/mL) and 0.14% type I collagenase (enzymes from Sigma Chemical Co., St. Louis Mo.), placed into 50 mL flasks with stirring, and incubated for 90 min at 37° C. in a humidified 5% $CO_2$ atmosphere. A portion of the cell suspension was used for cytospin slide preparation and was examined after hematoxylin and eosin staining of the tissue sections by a medical pathologist to confirm the diagnosis, and to determine the tumor cell count and viability.

After enzymatic dispersion into a near single-cell suspension, tumor cells were filtered through nylon mesh, washed in medium, suspended in soft agarose (0.12%) and plated at approximately 20,000 cells per well onto an agarose underlayer (0.4%) in 24-well plates. Cells were incubated under standard culture conditions for five days in the presence or absence of A10. Cells were pulsed with $^3$H-thymidine (Amersham, 5 mCi per well) for the last 48 hr of the culture period. After the appropriate labeling period, tissue culture plates were heated at 60° C. to melt the agarose, the cells harvested with a micro-harvester onto glass fiber filters and the radioactivity determined. Percent inhibition (PCI) was determined using the formula: PCI=1−(CPM treatment group II CPM control group). Determinations of control group proliferation were performed in quadruplicate, while treatment group proliferation was determined in triplicate.

Appendix 4

1. Animals

Female athymic mice (BALB/c, nu/nu), BALB/c mice, Wistar rats and Fisher 344 rats were obtained from Simonsen Laboratories (Gilroy, Calif.). Female A/J mice were obtained from Jackson Laboratory (Bar Harbor, Me). DA rats were obtained from B&K Universal, Inc. (Fremont, Calif.). Athymic R/Nu rats, DBA/2N mice, and BALB/c mice were obtained from Harlan Sprague Dawley (Indianapolis, Ind.). Female C57BL/6 mice were obtained from Taconic (Germantown, N.Y.). All animals were maintained under clean-room conditions in micro-isolator cages with Alpha-dri bedding. They received sterile rodent chow and water ad libitum.

2. Subcutaneous Xenograft Model

Cell lines were grown in appropriate medium (see Appendix 1). Cells were harvested at or near confluency with 0.05% Trypsin-EDTA and pelleted at 450×g for 10 min. Pellets were resuspended in sterile PBS or media (without FBS) to a particular concentration and the cells were implanted into the hindflank of mice. Tumor growth was measured over 3 to 6 weeks using venier calipers. Tumor volumes were calculated as a product of length×width×height unless otherwise indicated. P values were calculated using the Students' t-test. A10 in 50–100 μL excipient (DMSO, PBTE, PBTE6C:D5W, or PBTE:D5W) was delivered by IP injection at different concentrations.

3. Intracerebral Xenograft Model

For the mouse IC model, rat C6 glioma cells were harvested and suspended in sterile PBS at a concentration of $2.5\times10^7$ cells/mL and placed on ice. Cells were implanted into BALB/c, nu/nu mice in the following manner: the frontoparietal scalps of mice were shaved with animal clippers if necessary before swabbing with 70% ethanol. Animals were anesthetized with isofluorane and the needle was inserted through the skull into the left hemisphere of the brain. Cells were dispensed from Hamilton Gas-tight Syringes using 30 gauge ½ inch needles fitted with sleeves that allowed only a 3 mm penetration. A repeater dispenser was used for accurate delivery of 4 μL of cell suspension. Animals were monitored daily for well-being and were sacrificed when they had a weight loss of about 40% and/or showed neurological symptoms.

For the rat IC model, rats (Wistar, Sprague Dawley, Fisher 344, or athymic R/Nu; approximately 200 g) were anesthetized by an IP injection of 100 mg/kg Ketaset (ketamine hydrochloride; Aveco, Fort Dodge, Iowa) and 5 mg/kg Rompun (xylazine, 2% solution; Bayer, Germany). After onset of anesthesia, the scalp was shaved and the animal was oriented in a stereotaxic apparatus (Stoelting, Wood Dale, Ill.). The skin at the incision site was cleaned 3 times with alternating swabs of 70% ethanol and 10% Povidone-Iodine. A median 1.0–1.5 cm incision was made in the scalp using a sterile surgical blade. The skin was detached slightly and pulled to the sides to expose the sutures on the skull surface. A dental drill (Stoelting, Wood Dale, Ill.) was used to make a small (1–2 mm diameter) burrhole in the skull approximately 1 mm anterior and 2 mm lateral to the bregma. The cell suspension was drawn into a 50 μL Hamilton syringe fitted with a 23 or 25 ga standard bevel needle. The syringe was oriented in the burrhole at the level of the arachnoidea and lowered until the tip of the needle was 3 mm deep into the brain structure, where the cell suspension was slowly injected. After cells were injected, the needle was left in the burrhole for 1–2 minutes to allow for complete delivery of the cells. The skull was cleaned and the skin was closed with 2 to 3 sutures. Animals were observed for recovery from surgery and anesthesia. Throughout the experiment, animals were observed at least twice each day for development of symptoms associated with progression of intracerebral tumor. Animals displaying advanced symptoms (leaning, loss of balance, dehydration, loss of appetite, loss of coordination, cessation of grooming activities, and/or significant weight loss) were humanely sacrificed and the organs and tissues of interest were resected.

4. Intraperitoneal Model

Cell lines were grown in the appropriate media as described in Appendix 1. Cells were harvested and washed in sterile PBS or medium without FBS, resuspended to a suitable concentration, and injected into the IP cavity of dice of the appropriate strain. Prior to implantation of 7TD1 cells, C57BL/6 mice were primed by IP injection of 0.5 mL Pristane. SKOV3T cells were implanted into athymic mice without Pristane priming. Mice were observed daily for the occurrence of ascites formation. Individual animals were sacrificed when they presented with a weight gain of 40%, or when the IP tumor burden began to cause undue stress and pain to the animal.

5. Immunohistochemistry

Acetone-fixed, 5 µm frozen tissue sections from untreated xenograft tumors derived from human, rat, or murine tumor cells were analyzed by immunohistochemistry using highly specific receptor antibodies. Briefly, non-specific binding sites were blocked with 10% normal goat serum prior to the application of the primary antibody. Appropriate antibody concentrations were used to achieve the desired sensitivity and specificity (rabbit anti-human PDGF-b receptor, 1:400 and rabbit anti-mouse Flk-1, 5.5 µg/mL). Tissue sections known to contain the protein of interest served as positive controls. Appropriate negative controls of normal rabbit IgG and mouse anti-chicken IgG of the same protein concentration and isotype as the primary antibodies were used. The detection method was a three-step indirect procedure and consisted of the primary antibody bound to a biotin-labeled secondary antibody (goat anti-rabbit IgG 1:500) followed by streptavidin conjugated horseradish peroxidase.

The chromagen/substrate used was 0.05% diaminobenzidine/0.03% $H_2O_2$. Tissue sections were counterstained with hematoxylin, dehydrated through ascending grades of ethanol, cleared in Xylene Substitute, and cover-slipped with Permount for microscopic evaluation. A+ to +++ grading system was used to identify the overall intensity of the expression with +=low, ++=moderate, and +++=high intensity. Specific staining reaction was seen as either (T) tumor cell or (V) vascular endothelial cell or both.

Appendix 5

1. In vitro Immunology Assays

At the indicated times, animals were sacrificed, and the spleens were aseptically removed and placed into sterile medium. Spleens were processed into single cell suspensions by grinding between sterile frosted glass microscope slides. After a single wash to remove tissue debris, the spleen cells were resuspended in a hypotonic ammonium chloride buffer to lyse erythrocytes. Lymphocytes were washed and resuspended to the appropriate concentrations in complete medium, consisting of RPMI plus 10% heat-inactivated FBS, 2 mM glutamine, 50 µM β-mercaptoethanol, and penicillin-streptomycin. The responses of the lymphocytes were examined in the following assays according to accepted procedures (Current Protocols in Immunology. Coligan, J. E., Kruisbeek, A. M., Margulies, D. H., Shevach, E. M., Strober, W. (eds.) John Wiley and Sons, Inc., 1992).

1.a. Mitogen Responses

The T-cell mitogen, ConA, and the T-cell independent B-cell mitogen, LPS, were added to 96-well round-bottom wells at the indicated concentrations. Lymphocytes from normal, vehicle-dosed, and drug-dosed animals were added at a final concentration of $2.5 \times 10^5$/well. Cultures were usually set up in triplicate or quadruplicate. The plates were incubated at 37° C. in a humidified atmosphere containing 5% $CO_2$ for the indicated times. Supernatants (approximately 100 µL) were carefully removed from the wells and stored at −80° C. for lymphokine and immunoglobulin analyses. To measure proliferation of the lymphocytes, 1 µCi of $^3$H-thymidine was added to each well, and the plates were incubated for 6 hr. The cultures were harvested onto glass fiber filters, and the incorporated radioactivity was quantitated by liquid scintillation counting (Betaplate, Wallac).

1.b. Mixed Lymphocyte Responses

Lymphocytes from normal, vehicle-dosed, and drug-dosed animals were plated at $2.5 \times 10^5$/well in round-bottom 96-well plates. Stimulator cells were then added at the same cell concentration. The stimulator cells consisted of syngeneic or allogeneic lymphocytes which had been treated with 50 µg/mL of mitomycin C for 30 min prior to the assay. The plates were incubated for 3 to 4 days, at which time supernatants were harvested and the cultures were pulsed as described for the mitogen assays.

1.c. Lymphokine Assays

Supernatants from mitogen and MLR cultures were assayed for IL-2 and IL-6 content by the ability to support the growth of factor-dependent cell lines. HT-2 cells ($10^4$/well, IL-2-dependent) and 7TD1 cells ($2 \times 10^3$/well, IL-6-dependent) were plated in 96-well flat-bottom plates, in 50 µL/well. Supernatants were added in 50 µL/well, and the plates were incubated overnight (HT-2) or four days (7TD1). Cellular proliferation was determined in the MTT colorimetric assay (Appendix 3.1).

1.d. Immunoglobulin ELISA

Flat bottom 96-well EIA plates were coated with goat anti-mouse Ig antibodies (Southern Biotechnology) overnight at 4° C. The plates were blocked by the addition of PBS+1% BSA. After washing with PBS, supernatants from murine mitogen and MLR cultures were added and incubated at room temperature for 1 hr. The plates were washed with PBS, then HRP-labeled goat anti-mouse Ig antibodies were added and incubated at room temperature for 1 hr. The plates were washed and developed by the addition of substrate (ABTS).

Appendix 6

1. HPLC Assay

At specific times after treatment of mice or rats with A10, blood was collected in heparinized tubes by terminal cardiac puncture. Plasma was prepared and frozen in liquid nitrogen. Tissues and organs were resected and immediately frozen in liquid nitrogen. After the addition of an internal standard, plasma samples were acidified with HCl and extracted with acetonitrile. The acetonitrile fraction was evaporated to dryness in a vacuum centrifuge with heating and redissolved in methanol. Tissue and organ samples were homogenized according to the weight ratio of 1:5 (w:v) in 50 mM Tris-HCl, pH 7.4, at 20,000 rev/min, using a tissue homogenizer (Brinkmann Polytron Model PT3000). After the addition of an internal standard, the homogenate was acidified with HCl and then extracted with acetonitrile. The acetonitrile fraction was then extracted with an equal volume of diethyl ether. The ether fraction was evaporated to dryness in a vacuum centrifuge with heating and redissolved in methanol.

Samples for HPLC analysis were injected onto a Hewlett Packard Hypersil 5-µm C18 cartridge column (100×4.6 mm). The mobile phase was methanol:35 mM $KH_2PO_4$ (pH 4.5) 55:45 containing 4 mM triethylamine. The flow rate was 1.2 mL/min. The compounds were monitored by UV absorption at 254 nm using a Hewlett-Packard diode-array detector (HP Model 1090). Plasma and tissue concentrations were determined from standard curves using peak area for quantitation. Plasma and tissue standard curves were prepared from plasma and tissue homogenates obtained from drug-free rats, and spiked with known amounts of A10 and B11. The results were corrected for recovery of the internal standard. The internal standard used was 5-methyl-pyrazole-4-carboxylic acid-(4-trifluoromethyl)-anilide.

Appendix 7
1. Effects of A10 on Body Weight

Athymic mice (BALB/c, nu/nu, female, 4–5 weeks old) received IP administration of A10 (20 mg/kg/day) every day in 100 μL PBTE:D5W (1:1, v:v) for 101 days. Vehicle control animals received IP administration of 100 μL PBTE:D5W (1:1, v:v) every day for 101 days, and untreated control animals received no treatments. There were eight animals in each group. Weights were measured on day 0 (one day prior to drug administration) and two times/week until experiment termination. The percent weight change was calculated as mean weight at each determination as compared to the mean weight on day 0.

2. Determination of $LD_{50}$

Groups of five to ten athymic mice (BALB/c, nu/nu, female), or BALB/c mice (male and female) were treated with A10 IP in 50 μL PBTE, 100 μL PBTE, or 50 μL DMSO. In one experiment, groups of five BALB/c female, mice received IP administration of Decadron® (dexamethasone sodium phosphate for injection, 1.5 mg/kg) once per day for seven days prior to administration of a single IP dose of A10. In an additional experiment, groups of five BALB/c female mice received IP injection of Dilantin® (phenytoin sodium for injection 20 mg/kg) once per day for seven days prior to administration of a single dose of A10. All animals wee observed for 7 to 14 days after the last dose was administered. The $LD_{50}$ was calculated from a plot of % mortality versus dose (log M) using a four parameter logistic equation.

Example 1
Inhibition of PDGF-R Autophosphorylation by A10

This example illustrates the ability of A10 to inhibit PDGF-R autophosphorylation of rat C6 glioma cells. Rat C6 glioma cells ($5\times10^5$) were plated in MCDB105 medium containing 5% FCS in a 6-well plate and incubated for 24 hours at 37° C. The cells were then placed in media with 1% FCS for another 24 hours. The cells were treated with AIO at 50, 100, or 200 mM for one hour at 37° C. The cells were then treated with 20 ng/ml of PDGF-BB for 10 minutes at 37° C. The cells were lysed in 50 mM Tris-HCl (pH 7.4) containing 2 mM EDTA, 10% glycerol, 1% NP-40, 1 mM $Na^+$ orthovanadate, 10 mM pyrophosphate, 1 mM PMSF, 10 mg/ml aprotinin and 10 mg/ml leupeptin.

Proteins were then separated by SDS-polyacrylamide gel electrophoresis (PAGE). Proteins containing phosphorylated tyrosine were identified by western blotting with an anti-phosphotyrosine antibody. The level of phosphorylated tyrosine was determined by quantitating the amount of bound anti-phosphotyrosine. Quantitation was carried out by peak area integration using a Molecular Dynamics Computing Densitometer (Model 300S), and Image Quant v3.0 software (Molecule Dynamics). Data were expressed as relative peak.intensity (phosphorylation of a receptor divided by the total amount of phosphorylated tyrosine).

PDGF-BB stimulated autophosphorylation of the PDGF-R, while A10 inhibited such stimulation. Increasing concentrations of A10 resulted in reduced PDGF stimulated receptor phosphorylation. A10 at a concentration of 200 mM reduced PDGF-R phosphorylation below that occurring in the absence of PDGF-BB stimulation.

Example 2
Selective Inhibition of PDGF-R Autophosphorylation by A10

A10 inhibits autophosphorylation of the PDGF-R in human T98G glioblastoma cells, while having little if any effect on autophosphorylation of the EGF receptor. T98G cells were plated in MCDB105 medium containing 2% FBS and incubated for 24 hours at 37° C. The media was aspirated and then replaced with MCDB105 and the cells were treated for one hour with 200, 500 or 1,000 mM A10. Cells were treated with different concentrations of A10 (0, 200, 500 and 1000 mm) and in the presence or absence of ligand. The cells were then treated with ligand for 10 minutes (20 ng/ml PDGF-BB or 50 ng/ml EGF). The cells were lysed and the level of phosphorylated receptor was quantitated as described in Example 1. A10 inhibited autophosphorylation of PDGF-R by PDGF, but had little if any effect on the ability of EGF to stimulate autophosphorylation of EGF-R.

Example 3
Inhibition of PDGF-R Phosphorylation by Various Compounds

This example illustrates the ability of various compounds to inhibit PDGF-stimulated receptor phosphorylation. U1242 MG cells were plated in 96-well plates at a concentration of $5\times10^4$ cells/well in cultured media containing 0.5% FBS. The cells were incubated for 24 hours. The cells were then treated with a particular compound for 2 hours followed by the addition of 100 ng/ml PDGF-BB and incubation for 10 minutes.

Cells were lysed in 0.2 M Hepes, 0.15 M NaCl, 10% V/V glycerol, 0.04% Triton X-100, 5 mM EDTA, 5 MM $Na^+$ vanadate and 2 nM $Na^+$ pyrophosphate. Cell lysates were then added to an ELISA plate coated with an anti-PDGF receptor antibody (Genzyme). ELISA plates were coated at 0.5 mg of antibody/well in 150 ml of PBS for 18 hours at 4° C. prior to the addition of the lysate.

The lysate was incubated in the coated plates for 1 hour and then washed four times in TBST (35 mM Tris-HCl pH 7.0, 0.15 M NaCl, 0.1% Triton X-100). Anti-phosphotyrosine antibody (100 ml in PBS) was added and the mixture was incubated for 30 minutes at room temperature. The wells were then washed four times in TBST, a secondary antibody conjugated to POD (TAGO) was added to each well, and the treated wells were incubated for 30 minutes at room temperature. The wells were then washed four times in TBST, $ABTS/H_2O_2$ solution was added to each well and the wells were incubated for two minutes. Absorbance was then measured at 410 nm.

The cytotoxicity of each drug was also determined. The cells were plated as described above. Following incubation with drug, cell survival was measured by an MTT assay as described by Mossman *J. Immunol. Methods* 65:55–63 (1983), or by measuring the amount of LDH released (Korzeniewski and Callewaert, *J. Immunol. Methods* 64:313 (1983); Decker and Lohmann-Matthes, *J. Immunol. Methods* 115:61 (1988).

The results are shown in Table IX. $IC_{50}$ valves (i.e., the dose required to achieve 50% inhibition) were determined using the ELISA screening assay. $LD_{50}$ values (i.e., the dosage which results in 50% toxicity) were determined using an MTT or LDH assay.

$IC_{50}$ values for inhibiting PDGF-stimulated receptor phosphorylation in U1242 cells ranged from 0.4 to>500 mM. As seen in Table IX most of the compounds tested inhibited PDGF-stimulated receptor phosphorylation. In all cases inhibition of receptor phosphorylation was not due to non-specific effects on cell viability as shown by the higher LDSO. Thus, these drugs are good candidates for compounds which can be used to treat cell proliferative diseases by inhibiting PDGF-R activity. G13 and G14 had the lowest $IC_{50}$ but had a $LD_{50}$ less than A10. Generally, the preferred compounds are those having the highest therapeutic index ($LD_{50}/IC_{50}$), which is a measure of the safety index.

TABLE IX

| Compound | ELISA P-TYR U1242 IC50 (mM) | CYTOXICITY LDH U1242 LD50 (mM) | CYTOXICITY MIT U1242 LD50 (mM) |
|---|---|---|---|
| A10 | 65 | >500 | 700 |
| B10 | 180 | | |
| B12 | 100 | >500 | >1351 |
| B13 | 180 | | |
| B14 | 180 | | |
| B15 | 120 | | 200 |
| B16 | 35 | | 50 |
| B17 | 125 | >1000 | >500 |
| B18 | 160 | | |
| B19 | 100 | | |
| C10 | 25 | | >500 |
| C11 | 70 | >500 | >500 |
| D11 | 8 | >441 | 90 |
| D12 | 60 | >386 | >390 |
| D13 | 30 | >500 | >500 |
| D14 | 20 | >100 | >500 |
| D15 | 20 | 400 | 80 |
| D16 | 50 | >168 | >167 |
| D17 | >100 | | |
| E10 | 45 | | |
| E11 | 90 | | |
| E12 | 180 | | |
| E13 | >100 | | |
| E14 | 100 | | |
| E15 | 5 | | >100 |
| E16 | 125 | | |
| F10 | 45 | | |
| F11 | 100 | | |
| F12 | 70 | | |
| G10 | 10 | >485 | >490 |
| G11 | 15 | 90 | 145 |
| G12 | 10 | >333 | >333 |
| G13 | 0.4 | >100 | 100 |
| G14 | 0.8 | >100 | >500 |
| G15 | 100 | | |
| G16 | 35 | | >100 |
| G17 | 100 | | |
| G18 | 10 | >100 | |
| G19 | 90 | | |
| G20 | >100 | | |
| G21 | 6 | >100 | |
| G22 | 1 | >100 | |
| H12 | 30 | | |
| I10 | 90 | >317 | >320 |

Example 4
A10 Inhibits PDGF-stimulated DNA Synthesis and Cell Cycle Progression

This example illustrates the ability of A10 to inhibit PDGF-BB stimulated DNA synthesis and cell cycle progression. The effect of A10 on DNA synthesis in T98G cells in the absence or presence of PDGF-BB was determined by measuring $^3$H-thymidine incorporation into DNA. The percentage of cells in the S phase of the cell cycle was determined by flow cytometry.

Cells were cultured as described in the appendices above. The assay conditions were essentially those described by Pollack et al., *J. Neurosurg.* 73:106–112 (1990) with some modifications. Cells (rat C6 or human T98G) in log phase growth were transferred to 96-well dishes at $2 \times 10^4$ cells in 200 ml MCDB 105 medium containing 2% FBS. After an overnight attachment period the media was changed to serum free assay media (MCDB 105 with 5 mg/ml insulin) and the cells were incubated for 18–24 hours.

DNA synthesis studies were initiated by adding 50 ng/ml of PDGF-BB alone or in combination with various concentrations of A10. The effect on basal $^3$H-thymidine incorporation was determined in the absence of PDGF. The plates were incubated at 37° C. for approximately 18 hours. $^3$H-thymidine (Amersham, 5 Ci/mmol) was added to each well to yield a final concentration of 5 mCi/ml, the plates were returned to the 37° C. incubator, after 4 hours the medium was removed and the plates were put on ice. Each well was then washed twice with 200 ml ice-cold PBS. Radioactivity incorporated into DNA was separated from unincorporated $^3$H-thymidine by precipitation with 100 ml ice-cold TCA for 10 minutes. After two washes with ice-cold TCA, the precipitate was solubilized (1% SDS in 100 ml 20 mNM Tris-base) and transferred to liquid scintillation counting vials. Six ml of cocktail (Ready Safe, Beckman) was added and radioactivity quantified in a Beckman liquid scintillation counter model LS6000 SC.

A10 decreased PDGF-stimulated DNA synthesis in both types of cells, however a greater effect was seen in human T98G glioblastoma cells than rat C6 glioma cells. To confirm these results, the effect of A10 on PDGF-stimulated entry into the S phase of the cell cycle was examined. NIH3T3 cells engineered to overexpress the human PDGF-b receptor were growth-arrested (serum-starved) followed by treatment with PDGF ligand in the presence or absence of A10. The cells were analyzed for DNA content by flow cytometry. The results of this analysis are summarized in FIG. 3. Treatment with PDGF resulted in a marked increase in cells residing in S phase (62%) relative to cells not treated with PDGF (11%). However, cells treated with A10 showed a dose-dependent decrease in the number of cells progressing to the S phase of the cell cycle in response to PDGF, indicating that PDGF-stimulated mitosis was blocked by A10.

These results contrast with the results of a similar experiment in which A10 at a concentration of 100 mM was not able to inhibit EGF-stimulated mitosis in NIH3T3 cells overexpressing the human EGF receptor. (FIG. 3). These results confirm the selectivity of A10 for PDGF-mediated signaling.

Example 5
Inhibiting the Activity of Different Receptor Kinases

The ability of different compound to inhibit different receptor tyrosine kinases was tested. The testing results are shown in Table X.

TABLE X

| Compound | PDGFR IC50 ($\mu$M) | EGFR ID50 ($\mu$M) | HER2 IC50 ($\mu$M) | FLK-1 IC50 ($\mu$M) |
|---|---|---|---|---|
| G14 | 0.8 (W) | NT | NT | >30 (W) |
| G25 | 0.9 | >50 | >50 | >50 |
| J10 | 1 (W) | >100 | >100 | NT |
| G13 | 1.5 | NT | >50 | >10 (W) |
| P10 | 3 (W) | 31 | >100 | >25 |
| J11 | 3 | >100 | >50 | >25 |
| F10 | 5 (W) | NT | NT | >50 |
| G24 | 5 | >100 | >50 | 9.3 |
| D11 | 8 (W) | NT | NT | >50 |
| G10 | 10 (W) | NT | NT | >50 |
| G12 | 10 (W) | NT | NT | >50 |
| G18 | 10 (W) | 500 (W) | NT | NT |
| E14 | 10 (W) | NT | NT | >50 |
| G22 | 14 | >100 | >50 | 4.4 |
| D20 | 14 | >50 | >50 | >50 |
| C13 | 16 | 16 | 29 | 3.3 |
| D15 | 19 (W) | NT | NT | >50 |
| G11 | 20 (W) | NT | NT | NT |
| G29 | 23 | <0.8 | 34 | 10 |
| C10 | 25 (W) | NT | NT | NT |

TABLE X-continued

| Compound | PDGFR IC50 ($\mu$M) | EGFR ID50 ($\mu$M) | HER2 IC50 ($\mu$M) | FLK-1 IC50 ($\mu$M) |
| --- | --- | --- | --- | --- |
| G23 | 25 (W) | >100 | >100 | 325.2 |
| H10 | 25 (W) | NT | NT | >50 |
| H12 | 25 (W) | NT | NT | NT |
| P12 | 25 (W) | NT | >50 | >50 |
| P14 | 26 | >50 | 10 | >200 |
| D13 | 30 (W) | NT | NT | >50 |
| P25 | 30 (W) | >100 | >100 | >500 |
| G30 | 32 | >100 | 34 | 10 |
| D18 | 34 | >50 | >50 | >50 |
| P15 | 46 | >100 | >50 | >50 |
| D14 | 47 | >100 | >50 | >50 |
| G27 | 48 | >100 | >50 | >50 |

Example 6

In vitro Efficacy

The efficacy of A10 as a direct growth inhibitor was determined on tumor cell lines, and primary tumors isolated from patients. The effects of A10 on tumor cell lines were determined by exposing cells to a range of drug concentrations and quantitating cell density after 4 days using the procedures described in Appendix 3. Table XI provides the results of testing different cell lines.

TABLE XI

Effects of A10 on Growth of Various Tumor Types

| Tumor Type | Cell Line | IC$_{50}$ ($\mu$M) |
| --- | --- | --- |
| glioma | SF763T | 0.8 |
|  | SF767T | 3 |
|  | U1242 | 19 |
|  | A172 | 32 |
|  | T98G | 62 |
|  | U87MG | 78 |
|  | SF767 | 87 |
|  | SF763 | 110 |
|  | U373MG | 115 |
|  | U118MG | 150 |
|  | U1240 | 250 |
|  | U138MG | >400 |
| ovarian | SKOV3T | 40 |
|  | PA-1 | 40 |
|  | SKOV3 | >100 |
|  | Ovcar3 | >100 |
| breast | BT474 | >100 |
|  | MCF7/HER2 | 116 |
|  | MDA MB 468 | 150 |
|  | T47D | 195 |
|  | MDA MB 361 | 200 |
|  | MCF7 | 288 |
|  | ZR75-30 | 300 |
|  | ZR 75-1 | 355 |
|  | HBL100 | >400 |
|  | BT549 | >400 |
|  | SKBR3 | >400 |
| lung | Calu-6 | 70 |
|  | A549 | 118 |
|  | Calu-3 | >400 |
| prostate | PC3 | 46 |
|  | DU145 | >100 |
| melanoma | A375 | 25 |
|  | C81-61 | 40 |
| colon | Colo 320DM | 34 |
| epidermoid | A431 | 34 |
| leukemia | K562 | 26 |

The IC$_{50}$ values for A10 ranged from 0.8 $\mu$M up to >400 $\mu$M.

The effects of A10 on in vitro growth of primary tumor cells isolated from six patients with glioblastoma multiformae (GBM) and six patients with ovarian carcinoma were tested. Specimens were obtained from newly diagnosed and previously untreated patients and evaluated as described in Example 13, Appendix 3.

A positive correlation between inhibition of tumor growth by A10 and PDGF-R expression was observed for both tumor types. As the concentration of A10 increased (from 0 to 400 mM) tumor cell growth decreased for both types of tumors. The growth inhibition was dose-dependent for both tumor types and varied among the tumor cells. the IC$_{50}$ values ranged from 39 $\mu$M to 198 $\mu$M for the GBM tumors and from 20 mM to 140 mM for the ovarian tumors.

Example 7

In vivo Efficacy Studies Using A10 and B11

This example summarizes several experiments illustrating the ability of A10 to inhibit the growth of different tumors in vivo. The first series of experiments looks at effects of different formulation and treatment regimens. The second series of experiments looks at the effects of A10 on a variety of different tumors.

Different Formulations and Treatment Regimens

C6 and SKOV-3(T) cells were grown in culture, as described in "cell growth" above, and implanted into the hind flank of a female Balb/c nu/nu mouse at 3×10$^6$ cells (for C6 experiments), or 1×10$^7$ cells (for SKOV-3 experiments) in 100 ml of PBS on Day 0. U87MG, U118MG or U373MG human glioblastoma cells (obtained from the ATCC), or A4312 were also implanted into athymic mice. Mice implanted with tumors, and non-implanted mice were administered A10 or B11 via intraperitoneal injection in a volume of 50 ml of DMSO, 100 ml PBTE:D5W, or 100 ml PBTE beginning on Day 1 or as otherwise indicated. Tumors were measured using venier calipers and tumor volume was calculated as a product of tumor length, width, and height.

In one set of experiments mice were implanted with A431, rat C6 glioma cells, SKOV-3(T) ovarian tumor cells and treated with 15 mg/kg/day of A10 (DMSO). Tumor growth progressed logarithmically in untreated, and DMSO controls. In contrast, tumor growth progressed only slightly (i.e., greater than 90% inhibition in tumor growth after 20 days compared with control) in A10 treated animals implanted with rat C6 glioma cells or SKOV-3(T) ovarian tumor cells. A10 had little (i.e. no more than 25%) effect on A431 tumor growth. Tumor growth of mice implanted with rat C6 glioma cells was inhibited with 15 mg/kg/day of B11 (DMSO) to the same extent as implanted mice treated with 15 mg/kg/day of A10 (DMSO).

In another set of experiments mice implanted with C6 glioma cells were treated with A10. Table XII summarizes the ability of A10 to inhibit rat C6 glioma cells in athymic mice using different treatment regimens. The percent inhibition refers to size of the tumor from A10 treated animals, divided by the size of the tumor from vehicle control treated animals. The different treatment regimens resulted in inhibition of 51% to greater than 95%.

TABLE XII

A10 Dosing Regimen Studies

| Dose | Regimen | % Inhibition |
| --- | --- | --- |
| 20 mg/kg (PBTE:D5W) | daily | >95% |
| 20 mg/kg (DMSO) | 2 days | 77% |
| 20 mg/kg (DMSO) | 4 days | 60% |
| 30 mg/kg (DMSO) | 2 days | 91% |

TABLE XII-continued

A10 Dosing Regimen Studies

| Dose | Regimen | % Inhibition |
|---|---|---|
| 30 mg/kg (DMSO) | 3 days | 87% |
| 40 mg/kg (PBTE) | 2 days | >95% |
| 60 mg/kg (PBTE) | weekly | 51% |
| 100 mg/kg (PBTE) | weekly | 63% |

In another set of experiments the affects different A10 dosing regimens were examined on C6 glioma cells. A10 was administered IP at different doses using different regimens beginning one day post-implantation. The total dose of A10 administered to the animals was compared to percent inhibition. These studied showed that higher doses of A10 administered less frequently have anti-tumor efficacy equivalent to that seen with lower doses administered daily provided that the total dose administered is equal. For example, 95% inhibition of tumor growth could be achieved by the administration of A10 to mice at 20 mg/kg every day, 40 mg/kg every two days, or 80 mg/kg every four days. C6 cells ($3 \times 10^6$ cells) were implanted SC into the hindflanks of BALB/c, nu/nu mice.

In another set of experiments the affect of different doses of A10 on glioblastoma were determined. Table XIII presents data illustrating the ability of A10 to inhibit glioblastoma cells in vivo.

TABLE XIII

| Cell Line | Dose (mg/kg) | % Inhibition |
|---|---|---|
| U87 | 5 | 52 |
|  | 10 | 58 |
|  | 15 | 66 |
|  | 20 | 92 |
| U118 | 15 | 57 |
| U373 | 15 | 54 |
| SF763T | 20 | 89 |
| SF767T | 20 | 70 |

The percent inhibition refers to tumor size in treated animals versus tumor size in untreated animals.

Table XIV compares the efficacy of different A10 formulations in vivo (mice implanted with C6 cells). PBTE, PBTE:D5W and DMSO formulations showed equivalent in vivo inhibition of tumor growth.

TABLE XIV

Efficacy vs. Formulation

| Dose | Formulation | % Inhibition |
|---|---|---|
| 15 mg/kg/day | DMSO | 90% |
| 20 mg/kg/day | DMSO | 95% |
| 15 mg/kg/day | PBTE | 92% |
| 20 mg/kg/day | PBTE | >95% |
| 40 mg/kg/2 days | PBTE | >95% |
| 20 mg/kg | PBTE:D5W | >95% |

The effects of A10 on animal mortality, using DMSO, PBTE, or PBTE:D5W formulations is presented in Table XV (mice implanted with C6 cells). PBTE:D5W formulations significantly reduced the mortality rate compared to DMSO formulations, and PBTE formulations.

TABLE XV

Effects of A10 on Mortality

| Dose | Treatments | Mortality | n |
|---|---|---|---|
| 20 mg/kg/day (DMSO) | 21 | 54% | 26 |
| 20 mg/kg/day (PBTE:D5W) | 27–100 | 0% | 80 |
| 25 mg/kg/day (PBTE:D5W) | 67 | 0% | 8 |
| 20 mg/kg/day (PBTE) | 20–48 | 8% | 12 |
| 30 mg/kg/day (PBTE) | 48 | 50% | 4 |
| 40 mg/kg/day (PBTE) | 48 | 75% | 4 |

Inhibition of Different Tumor Types by A10

This section describes experiments comparing the ability of A10 to inhibit the growth of different types of tumors. In one set of experiments the ability of A10 to inhibit ovarian, melanoma., prostate, lung, and mammary tumor cell lines established as SC xenografts was examined using the procedures described in the appendices. In a second set of experiments the effects of A10 on the growth of murine leukemia cell lines in a synthetic model were tested as using the procedures described in the appendices above.

Table XVI summarizes the results of the studies using SC xenografts. At doses ranging from 12 to 20 mg/kg/day, A10 effectively inhibited the growth of glioma, SKOV3T (human ovarian), PA-1 (human ovarian), A375 (human melanoma), PC-3 (human prostate), Calu-6 (human lung), and D1B and L1210 (murine leukemias). However, A10 failed to significantly inhibit the growth of A549 (human lung), MCF7 (human mammary) and A431 (human epidermoid) xenografts.

TABLE XVI

Effect of A10 on Tumor Growth

| Tumor type | Cell line | Strain | Dose mg/kg/day | % Inhibition (day)** | P < *** |
|---|---|---|---|---|---|
| glioma | C6* | nu/nu | 20 | >95 (21) | 0.00001 |
|  | C6* | nu/nu† | 20 | 84 (18) | 0.00001 |
|  | 9L* | nu/nu | 20 | 83 (20) | 0.00001 |
|  | U87MG | nu/nu | 15 | 75 (28) | 0.0092 |
|  | U118T | nu/nu | 15 | 57 (47) | 0.0027 |
|  | U373MG | nu/nu | 15 | 54 (37) | 0.0477 |
|  | SF763T | nu/nu | 20 | 85 (22) | 0.00001 |
|  | SF767T | nu/nu | 20 | 70 (22) | 0.00001 |
| ovarian | SKOV3T | nu/nu | 15 | 94 (21) | 0.0014 |
|  | PA-1 | nu/nu | 20 | 53 (36) | 0.04 |
| melanoma | A375 | nu/nu | 20 | 53 (31) | 0.03 |
|  | A375 | SCID¥ | 15 | 35 (31) | 0.002 |
| prostate | PC-3 | nu/nu | 20 | 71 (45) | 0.01 |
|  | PC-3 | SCID£ | 12 | 47 (36) | 0.001 |
| lung | Calu-6 | nu/nu | 20 | 64 (28) | 0.0001 |
|  | A549 | SCID¶ | 15 | 19 (48) | NS |
| leukemia | D1B* | DBA/2 | 20 | 95 (22) | 0.00001 |
|  | L1210* | DBA/2 | 20 | 75 (18) | 0.04 |
| epidermoid | A431 | nu/nu | 15 | 40 (15) | NS |
| mammary | MCF7 | SCID∫ | 15 | 8 (27) | NS |

Table XVI. Tumor cells were implanted SC into the indicated strains of mice. Daily treatment with vehicle or A10 was initiated on day one post-implant, with the following exceptions:
† = day, ¥ = day 9, £ = day 15, ¶ = day 29. ∫ = day 8.
*D1B and L1210 are murine tumor cell lines, C6 and 9L are rat tumor cell lines; all others are human tumor cell lines.
**Data are presented as percent inhibition of tumor growth on the day indicated as compared to vehicle control; n = 8 to 10 mice/group except D1B and L1210 where n = 4 mice/group.
***P values were calculated by Student's t-test; NS = not significant.

In the second set of experiments, A10 was found to significantly increase the survival of animals bearing SKOV3T IP Xenografts and mice bearing 7DT1 iosgrafts. In one experiment, SKOV3T cells ($2 \times 10^6$ cells) were implanted into the IP cavity of BALB/c, nu/nu mice. A10 was administered IP in 50 μL DMSO at 15 mg/kg/day for 21 days beginning one day post-implantation and mice were monitored for survival (8 animals per treatment and control group). All animals in the control group died after 27 days, while one of A10 treated animals died by 28 days and 40% of A10 treated animals were alive after 32 days.

In another experiment, 7TD1 (B-cell hybridoma) cells were implanted IP in syngeneic immunocompetent C57BL/6 mice and the animals were treated for 30 days with 15 mg/kg/day of A10 (8 animals per treatment and control group). A10 was administered IP in 50 μL DMSO at 15 mg/kg/day for 30 days beginning one day post-implantation. Dosing ceased on day 30, and surviving mice were observed for an additional 50 days. All animals in the control group died by day 9, while 3 of 8 animals in the A10-treated group survived past day 80.

Example 8

Targeting Cancer Characterized by Inappropriate PDGF-R Activity

This example illustrates the ability of A10 to inhibit cancers characterized by inappropriate PDGF-R activity while having little or no effect on tumors not characterized by PDGF-R activity. PDGF-R expression was measured qualitatively using a western blot. SRB assays assessed cell growth by determining total cellular protein using sulforhodamine-B (Skehan, T et al., *J. Natl. Cancer Inst.* 82:1107–1112 (1990). Soft agar assays (SAA) were carried out by seeding cells at colony density in a semi-solid agar medium onto a base layer of agar after two to three weeks the size and number of colonies were quantitated with an automated Omincon 3800™ tumor colony counter. SRB and SAA values are expressed as $IC_{50}$ values in mM. In vivo inhibition was determined in xenografted athymic mice. The results are shown in Table XVII.

TABLE XVII

RECEPTOR EXPRESSION vs. GROWTH INHIBITION

| Cell Line | PDGF-R Expression | SRB | SAA | In Vivo |
| --- | --- | --- | --- | --- |
| C6 | ++ | 0.3 | 0.4 | 95% |
| SF767 | − | 100 | ND | 18% |
| SF767T | ++ | 3 | 0.5–2 | 70% |
| SF763 | − | >100 | ND | 35% |
| SF763T | ++ | ND | ND | 89% |
| SKOV-3 | − | >100 | 6.3 | ND |
| SKOV-3T | ++ | 50 | 0.3 | 95% |

As seen in Table XVII growth inhibition is strongest on cells expressing high levels of PDGF-R, establishing a clear link between receptor activity and cancer cell proliferation.

Example 9

Post Implant In vivo Inhibition Using A10

This example describes the effects of A10 when administered to mice a number of days after cancer implantation.

In one experiment, SCID mice containing PC-3 prostate cell line were treated with A10 starting 15 days after tumor transplant. The weekly treatment comprised 12 mg/kg/day of A10 (PBTE:D5W) for five days and two days of no treatment. The mice were treated for three week. In another experiment, mice containing A375 melanoma were treated in the same way as those implanted with PC-3 except 15 mg/kg/day of A10 was used and treatment began 9 days after tumor implant.

In both cases, tumor growth was inhibited by A10. PC-3 tumor growth was inhibited about 50% after three weeks. A375 melanoma growth was inhibited about 40% after three weeks. Thus, this example further illustrates the utility of A10 to inhibit tumor growth by showing its ability to inhibit tumor which have been growing in a host prior to treatment (Cf. Example 7 where treatment of tumor began one day after transplant).

Example 10

Effect of A10 on Intracerebral Tumor Growth

The effect of A10 on tumor growth in brain tumor models was examined in a series of experiments.

In two separate experiments A10 was administered to athymic mice following intracerebral (IC) implantation of C6 cells, the average survival time of A10-treated animals was significantly increased compared to controls. The results of this experiment are shown in FIG. 4).

In another experiment, in which A10 was administered to athymic mice following IC implantation of U87MG cells, the mean survival of the A10-treated.animals was 65 days compared to a mean survival of 60 days in control animals an increase. that was not significant (P=0.15).

The efficacy of A10 was also tested in an IC model in athymic rats. As shown in FIG. 5, A10 had a slight but significant positive effect on the survival of athymic rats following the IC implantation of C6 tumor cells.

Example 11

Immunology Studies

The effects of A10 on several parameters of normal immune function, including proliferation of lymphocytes, generation of cytotoxic effector cells, lymphokine production, and immunoglobulin secretion, were examined. These studies involved in vivo treatment of rats and mice with A10, followed by in vitro analyses of immune function. A detailed summary of the methods used in the immunology studies are described in Appendix 5.

Effects of In vivo Administration of A10 on Immune Function of Normal Mice

Naive BALB/c mice were treated with 15 mg/kg/day of A10 or vehicle (PBTE:D5W) for 7 and 21 days. The animals were sacrificed and their spleen cells were assayed in vitro for responses to ConA (a T-cell mitogen), LPS (a T-cell independent B-cell mitogen), and alloantigens (C3H/HeJ spleen cells) as described in Appendix 5. The IL-2, IL-6, Ig content and cellular proliferation were measured after 48 hr (mitogens) or 72 hr (alloantigens). The results are summarized in Table XVIII.

TABLE XVIII

Effects of A10 on Normal Immune Function in Naive Mice

| Stimulus | IL-2 production | | IL-6 production | | Ig production | | $^3$H-thymidine uptake | |
|---|---|---|---|---|---|---|---|---|
| | d7 | d21 | d7 | d21 | d7 | d21 | d7 | d21 |
| ConA | 0 | 0 | ++ | 0 | 0 | 0 | 0 | 0 |
| LPS | 0 | 0 | 0 | 0 | + | +/− | 0 | 0 |
| Allo | 0 | 0 | 0 | 0 | 0 | 0 | 0 | 0 |

Table XVIII. Female BALB/c mice were treated with A10 for 7 or 21 days. Spleen cells were removed and stimulated in vitro with mitogens or alloantigens. Cellular proliferation, cytokine production, and Ig production were assayed as described in Appendix 5. Results are presented as a comparison between drug-treated and vehicle-treated (PBTE:D5W) animals. 0=no change; +/−=slight increase in some animals; +=moderate increase in all animals; ++=strong increase in all animals.

Two parameters appeared to be affected by A10 treatment: ConA-induced IL-6 production was higher in the A10-treated group than in controls at day 7, but this difference was not apparent at day 21. LPS-induced Ig production was slightly higher in the A10 group than in controls following 7 days of treatment, but this difference was not apparent in 3 of 4 mice treated with drug for 21 days. These data indicate that the effects of A10 on IL-6 production and Ig production by splenocytes were transient even with continued administration of A10.

Effects of In vivo Administration of A10 on Immune Function of Mice During a Primary Immunization The effect of A10 in animals responding to an active primary immunization was also examined. BALB/c mice were immunized SC with 50 μg keyhole limpet hemocyanin (KLH) suspended in complete Freund's adjuvant (CFA); control mice were mock-immunized with an emulsion of phosphate-buffered saline (PBS) in CFA. Beginning on day 1, mice were divided into three treatment groups: untreated, vehicle (PBTE:D5W) only, or A10 at 20 mg/kg/day. On day 14, all mice were sacrificed, and their spleen cells were assayed. In addition, immune e responses to KLH and tetanus toxoid were measured as described in Appendix 5.

Cytokine production (IL-2 and IL-6) by splenocytes was not significantly affected by vehicle alone or drug as summarized in Table XIX. However, A10 treatment was associated with a slight inhibition of the proliferative responses of spleen cells after restimulation with the immunizing antigen (KLH) in vitro,. (Table XIX). Similar effects were seen when the spleen cells were stimulated with LPS or allogeneic cells (Table XIX).

TABLE XIX

Effects of A10 on Normal Immune Function in Mice Responding to a Primary Immunization

| Stimulus | IL-2 production | IL-6 production | Ig production | $^3$H uptake |
|---|---|---|---|---|
| KLH | 0 | 0 | 0 | − |
| ConA | 0 | 0 | 0 | 0 |
| LPS | 0 | 0 | 0 | − |
| Allo | 0 | 0 | 0 | − |

TABLE XIX. BALB/c mice were immunized with KLH, then divided into three treatment groups; dosing began on day 1 and continued until day 14 post-immunization. Spleen cells from untreated, vehicle-treated, or A10-treated mice, a well as non-immune control mice (normal) were cultured with the indicated mitogens or alloantigens. Cellular proliferation, cytokine production, and immunoglobulin production were assayed as described in Appendix 5. Result are presented as a comparison of the responses of drug-treated animals to those of vehicle-treated (PBTE:D5W) controls. 0 = no change; −=slight decrease in all animals.

Effects of In vivo Administration of A10 on Immune Function of Tumor-Bearing Mice BALB/c mice received SC implants of syngeneic WEHI-164.13 fibrosarcoma cells on day 0. On day 1, the mice were divided into three treatment groups: untreated, daily treatment with vehicle alone (PBTE:D5W), or daily treatment with A10 at 20 mg/kg/day. On day 17, the animals were sacrificed and their spleens were removed. The spleen cells were assayed in vitro for responses to alloantigens and mitogens. Treatment with A10 did not affect the proliferation, cytokine secretion, or Ig secretion of spleen cells stimulated with alloantigen or mitogens as summarized in Table XX.

The spleen cells were also assayed for the generation of WEHI-164.13-specific cytotoxic T-lymphocytes (CTL) in the mixed lymphocyte tumor cell culture (MLTC). Spleen cells from untreated tumor-bearing animals mounted a vigorous CTL response (44% specific lysis at E:T=50:1). This response was inhibited almost completely in animals receiving the vehicle alone (13% specific lysis). The vehicle has an ethanol content of ~15% and ethanol is known to transiently effect CTL generation and activity. (Walia, et al., *Proc. Soc. Exp. Biol. Med.*, 192:177–200, 1989.)

Treatment with A10 enhanced the CTL response (78% specific lysis) compared to vehicle-treated animals; the CTL response of spleen cells from A10-treated mice was also higher than that from untreated control animals. Thus, it appears that in this immunocompetent mouse model, A10 dosing overcomes the inhibitory effect of the vehicle in the generation of CTL.

TABLE XX

Effects of A10 on Normal Immune Function in Mice Bearing a Primary Tumor

| Stimulus | IL-2 production | IL-6 production | Ig production | CTL activity |
|---|---|---|---|---|
| Tumor | 0 | 0 | 0 | ++ |
| ConA | 0 | 0 | 0 | NT |
| LPS | 0 | 0 | 0 | NT |
| Allo | 0 | 0 | 0 | NT |

Table XX. Tumor-bearing mice were treated with vehicle or A10, or left untreated, for 17 days post-implantation. Mice were sacrificed and spleen cells were cultured with the indicated mitogens, alloantigens, or mitomycin C-treated WEHI-164.13 tumor cells. Cellular proliferation, cytokine production, immunoglobulin production, and CTL activity were assayed as described in Appendix 5. Results are presented as a comparison of the responses of drug-treated animals to those of vehicle-treated (PBTE:D5W) controls. 0 =no change; ++=strong increase in all animals; NT=not tested.

Effects of In vivo Administration of A10 on Immune Function of Rats

Wistar rats received SC implants of C6 cells on day 0. Beginning on day 1, and daily thereafter, the rats received IP doses of vehicle (PBTE:D5W) or A10 at 8.4 mg/kg/day (equivalent to 20 mg/kg/day of A10 in mice). The control group was not treated after tumor implantation. On day 21, the animals were sacrificed and the spleens were removed for in vitro analyses. Splenocytes were stimulated with ConA, LPS, and alloantigen (DA rat spleen cells) as in the murine studies.

Of the parameters measured, only cellular proliferation in the syngeneic mixed lymphocyte response (MLR) appeared to be affected by A10 treatment as summarized in Table XXI. The syngeneic MLR of the untreated, vehicle-treated, or tumor-bearing animals was much higher than that of the non-tumor bearing animals. This proliferative response was reduced in one of four A10-treated tumor-bearing animals to a level similar to non-tumor bearing controls. The allogeneic response was not reduced.

The spleen cells from Wistar rats were also assayed for the generation of C6-specific CTL in the MLTC and the results summarized in Table XXI. Spleen cells from tumor-bearing, untreated animals mounted a vigorous CTL response (35% specific lysis at E:T=100:1), while cells from non-tumor bearing control rats mounted a weak response (13% specific lysis at E:T=100:1). Similar to the studies in BALB/c mice, it appeared that the vehicle inhibited the generation of CTL in a 7-day culture. In contrast to the murine studies however, A10 did not overcome the inhibitory effect of the vehicle in immunocompetent rats.

TABLE XXI

Effects of A10 on Normal Immune Function in Rats Bearing a Primary Tumor

| Stimulus | IL-2 production | IL-6 production | $^3$H-thymidine uptake | CTL activity |
|---|---|---|---|---|
| Tumor | 0 | 0 | 0 | 0 |
| ConA | 0 | 0 | 0 | NT |
| LPS | 0 | 0 | 0 | NT |
| Syn | 0 | 0 | +/− | NT |
| Allo | 0 | 0 | 0 | NT |

Table XXI. Wistar rats received SC implants of C6 cells, followed by daily treatment with vehicle or A10; tumor-bearing, untreated animals and normal, non-tumor-bearing animals were included in the study. On day 21, animals were sacrificed and their spleen cells were stimulated with the indicated mitogens (ConA, LPS), syngeneic (Syn) or alloantigens (Allo), or mitomycin C-treated C6 tumor cells. Cellular proliferation, cytokine production, and CTL activity were assayed as described in Appendix 5. Results are presented as a comparison of the responses of drug-treated animals to those of vehicle-treated (PBTE:D5W) controls. 0=no change; +/−=decrease in some drug-treated animals to levels detected in normal (non-tumor-bearing, non-drug-treated) animals; NT=not tested.

The results of these immunology studies indicate that A10 does not adversely affect the normal immune responses of immunocompetent or immunodeficient rodents during or following in vivo dosing. Furthermore, the efficacy of the drug when tested against murine tumor cell lines in syngeneic immunocompetent hosts indicates that A10 does not impair anti-tumor immunity.

Example 12
Pharmacology of A10

Several pharmacological properties of A10 have been studied in mice and rats including its metabolism and half-life in plasma and brain tissue. A detailed description of the methods utilized in studying the pharmacology of A10 can be found in Appendix 6. In addition, the pharmacokinetic profile of A10 was studied in conjunction with formal toxicity studies of the compound in rats and monkeys.

Metabolism of A10

The isoxazole ring of A10 undergoes an intramolecular rearrangement to 2-cyano-3-hydroxy-N-[4-(trifluoromethyl)phenyl]-2-butenamide (B11). The metabolism of A10 to B11 was investigated ex vivo in fresh heparinized plasma from humans or rats. The conversion of A10 to B11 was monitored using reverse-phase HPLC as described in Appendix 6. At 25° C. (ambient temperature), A10 underwent complete conversion to B11 by 21 hr in human plasma. A similar experiment was performed using rat plasma with incubation at 37° C.; A10 was completely converted to B11 after a 2 hr incubation. The conversion of A10 to B11 does not occur in heat-inactivated plasma (15 min at 60° C.) from humans or rats. Additionally, both B11 and A10 together were incubated with fresh human plasma and the concentrations monitored. No A10 was detected after 21 hr; only B11 was present The metabolite, B11, appears to be equipotent to A10 in in vitro growth assays as well as equipotent in inhibiting PDGF-stimulated DNA synthesis and PDGF-stimulated cell cycle progression. B11 is also equipotent in the inhibition of the growth of C6 tumors in vivo. These data suggest that Bil is an active metabolite of A10. The use of A10 to treat cell proliferative disorders is preferred because it is more suitable than B11 for formulation as an IV solution.

Pharmacokinetics of A10 and B11 In vivo

The pharmacokinetics of A10 and its metabolite (B11) were investigated in vivo after intraperitoneal (IP) administration of A10 to mice and rats. When athymic (BALB/c, nu/nu, female) mice received A10 (120 mg/m², 40 mg/kg), the drug was converted to Bil at 3 hr post-dose, while the concentration of the parent compound was below the limits of detection in the systemic circulation. B11 was detected in plasma for more than 48 hr and had a $t_{1/2}$ of 16 hr and $T_{max}$ of 3 hr. The area under the concentration time curve (AUC) for B11 was calculated to be 2773 µg.h/mL. The clearance rate (CL) was calculated to be 0.29 mL/hr, assuming 100% bioavailability and mean input time is zero. The volume of distribution (VD) was calculated to be 6.7 mL. In the brains of these mice, B11 exhibited a $t_{1/2}$ of 14 hr and a $T_{max}$ of 3 hr.

TABLE XXII

Pharmacokinetics of A10 and B11 in Mice and Rats After IP Administration

| | | athymic mice | | | BALB/c | Wistar |
|---|---|---|---|---|---|---|
| | | 40 mg/kg 120 mg/m² single dose | 75 mg/kg 225 mg/m² single dose | 75 mg/kg 225 mg/m² 1/week x 4 | mice 40 mg/kg 120 mg/m² single dose | rats 80 mg/kg 560 mg/m² single dose |
| Plasma | | | | | | |
| $t_{1/2}$ (hr) | B11 | 16 | 15.5 | 16.9 | 14.9 | 6 |
| | A10 | <1.5 | <1 | <1 | ND | <2 |
| $T_{max}$ (hr) | B11 | 3 | 3 | 3 | 3 | 6 |
| | A10 | <0.5 | ND | ND | ND | <2 |
| $C_{max}$ | B11 | 111 ± 14 | 249 ± 26 | 190 ± 12 | 208 ± 34 | 260 |
| | A10 | ND | ND | ND | ND | 5.0 |
| AUC (µg · hr/mL) | | 2773 | 5660 | 5012 | 4444 | 6417 |

TABLE XXII-continued

Pharmacokinetics of A10 and B11 in Mice and Rats After IP Administration

|  |  | athymic mice | | | BALB/c | Wistar |
|---|---|---|---|---|---|---|
|  |  | 40 mg/ kg 120 mg/m² single dose | 75 mg/ kg 225 mg/m² single dose | 75 mg/ kg 225 mg/m² 1/ week × 4 | mice 40 mg/kg 120 mg/m² single dose | rats 80 mg/kg 560 mg/m² single dose |
| CL (mL/hr) |  | 0.29 | 0.27 | 0.30 | 0.18 | 0.26 |
| VD (mL) |  | 6.7 | 6.4 | 8.2 | 3.1 | 5.3 |
| Brain |  |  |  |  |  |  |
| t½ (hr) | B11 | 14 | NT | NT | 2 | 6 |
|  | A10 | <1.5 | NT | NT | <1 | 20 |
| $T_{max}$ (hr) | B11 | 3 | NT | NT | 1 | 6 |
|  | A10 | 1.0 | NT | NT | 1.0 | 7 |

Table XXII. Female athymic mice (BALB/c, nu/nu; four per group) were treated IP with A10 as indicated. BALB/c mice (female, four per group) were treated IP with 120 mg/m² (40 mg/kg) A10. Wistar rats (female, one per time point) were treated IP with 560 mg/m² (80 mg/kg) A10. Plasma and brain samples were prepared and analyzed by HPLC as described in Appendix 6. All results were calculated by the method of internal standardization. NT= not tested, ND= not detected.

The pharmacokinetic profile was also determined in athymic mice for the A10 dose calculated to be the $LD_{10}$. Intraperitoneal administration of A10 at 225 mg/m² (75 mg/kg) resulted in the detection of B11 in plasma for more than 48 hr (the last time point analyzed) with a $t_{1/2}$ of 15.5 hr and $T_{max}$ of 3 hr (Table XXII). The AUC was calculated to be 5660 µg.hr/mL. The CL was calculated to be 0.27 mL/hr, assuming 100% bioavailability and mean input time is zero. The VD was calculated to be 6.4 mL.

The pharmacokinetic profile of the A10 $LD_{10}$ (75 mg/kg) was also studied in mice after four IP treatments given once every 7 days. B11 was detected in plasma for 48 hr after the last dose and had a $t_{1/2}$ of 16.9 hr and $T_{max}$ of 3 hr (Table XXII). The AUC for B11 was calculated to be 5012 µg.hr/mL. The CL was calculated to be 0.3 mL/hr, assuming 100% bioavailability and mean input time is zero. The VD was calculated to be 8.2 mL.

The pharmacokinetic profile of A10 was determined in BALB/c mice.

BALB/c mice received a single IP dose of A10 (120 mg/m², 40 mg/kg). A10 had been completely converted to B11 and was undetectable by 1 hr following drug administration. B11 was detected in plasma for more than 48 hr (the last time point analyzed) and had a $t_{1/2}$ of 14.9 hr and $T_{max}$ of 3 hr as summarized in Table XXII. The AUC was calculated to be 4444 µg.hr/mL. The CL was calculated to be 0.18 mL/hr, assuming 100% bioavailability and mean input time is zero. The VD was calculated to be 3.1 mL. In the brains of these mice, B11 exhibited a $t_{1/2}$ of 2hr and a $T_{max}$ of 1 hr (Table XXII).

When rats (Wistar, female) received a single IP dose of A10 (560 mg/m², 80 mg/kg) the drug was converted to B11 by 2 hr post dose, the first time point analyzed. However, A10 was detectable up to 8 hr post-dose. As summarized in Table XXI, A10 had a $t_{1/2}$ of <2 hr and $T_{max}$ of <2 hr. B11 was detected for greater than 24 hr post-dose and had a $t_{1/2}$ of 6 hr and $T_{max}$ of 6 hr. The AUC was calculated to be 6417 µg.hr/mL. The CL was calculated to be 0.26 mL/hr, assuming 100% bioavailability and mean input time is zero. The VD was calculated to be 5.3 mL. In the brains of these rats, B11 exhibited a $t_{1/2}$ of 6 hr and a $T_{max}$ of 6 hr while A10 exhibited a $t_{1/2}$ of 20 hr and a $T_{max\ of}$ 7 hr (Table XXII).

In vivo Plasma Levels

In vivo plasma levels of B11 were determined in athymic mice after either a single dose or repeated daily doses of A10 and the results are summarized in Table XXII. Three hours (at the $T_{max}$) after a single administration of A10 (20 mg/kg), the B11 concentration was determined to be 51.2±7.3 µg/mL (range 38.8–55.2 µg/mL) while A10 was not detected. The plasma steady-state levels of B11 were also determined in athymic mice after repeated administration (20 mg/kg/day) of A10 at 24 hr intervals (8 administrations). The steady-state maximum plasma level of B11 was 79.7±11.2 µg/mL (range 65.2–94.6 µg/mL), and the steady-state minimum or trough level was 33.6±7.3 µg/mL (range 23.4–45.8 µg/mL). The plasma level of B11 after achieving steady-state (maximum steady-state level) was 64% greater than after a single dose (Table XXII).

TABLE XXIII

Plasma Levels of B11

| | B11 Concentration (µg/mL) | | |
|---|---|---|---|
| A10 Dose | Single Dose | Multiple Doses | % Increase |
| 20 mg/kg | 51.2 ± 7.3 | 79.7 ± 11.2 | 64 |
| 40 mg/kg | 110.9 ± 15.3 | 161.1 ± 27.8 | 69 |

Table XXII. Plasma levels of B11 were determined after single or multiple daily administrations of A10 at 20 or 40 mg/kg/day in athymic mice. All data are the mean of 4 animals.

The B11 plasma concentration at $T_{max}$ was also determined after a single administration of A10 at 40 mg/kg. The B11 concentration was 110.9±15.3 µg/mL (range 93.5–131.3 µg/mL) while A10 was not detected. The plasma steady-state levels of B11 were also determined in athymic mice after repeated administration (40 mg/kg) of A10 at 24 hr intervals (6 administrations). The steady-state maximum plasma level of B11 was 161.1±27.8 µg/mL (range 119.9–204.1 µg/mL), and the steady-state minimum or trough level was 38.2±21.7 µg/mL (range 13.5–66.9 µg/mL). The plasma level of B11 after achieving steady-state was 69% greater than after a single dose (Table XXII). These data demonstrate that B11 accumulates in plasma after multiple daily administrations of A10.

In addition to plasma levels, concentrations of A10 and B11 were determined in brain tissue after administration of A10 to rats and mice. The results are summarized in Table XXIV. The brain levels of B11 and A10 differed between both species and strains. The highest level of B11 in the brain was detected in athymic mice, followed by BALB/c mice, and Wistar rats respectively. At 2 and 4 hr post-dose, there was 11 and 6.5 times, respectively, more B11 in the brains of athymic mice compared to Wistar rats. At 2 hr post-dose, there was 2 times more A10 in the brains of athymic mice as compared to Wistar rats; at 4 hr post-dose approximately equivalent amounts of A10 were detected in the brains of athymic mice and Wistar rats.

TABLE XXIV

Comparison of B11 and A10 Levels in Brain Tissue

B11 and A10 Concentration in Brain Tissue (ng/mg)

| Time Post- dose | Athymic mice | | BALB/c mice | | Wistar rats | |
|---|---|---|---|---|---|---|
| | B11 | A10 | B11 | A10 | B11 | A10 |
| 2 hr | 21.9 ± 12.7 | 19.9 ± 13.5 | 3.5 ± 2.8* | 9.1 ± 13.5* | 1.9 ± 1.5 | 8.9 ± 4.8 |
| 4 hr | 21.3 ± 19.3 | 1.8 ± 1.6 | 10.7 ± 3.7 | 3.8 ± 2.9 | 3.3 ± 1.5 | 2.1 ± 3.2 |

Table XXIV. B11 and A10 levels in brain tissue were determined as described in Appendix 6. *Determined at 2.5 hr post-dose. n=4 animals.

These pharmacology studies demonstrate that A10 is metabolized to B11 in both mice and rats. In addition, A10 and B11 can be detected in both plasma and brain tissue. However, there appears to be a difference in both the pharmacokinetics and distribution of A10 and B11 to plasma and brain between the two species examined.

Example 13
Preliminary Toxicology Studies Using A10

Preliminary toxicology studies of A10 included testing the effect of A10 on blood cells, body weight, LD50 determinations. To determine the effect of potential ancillary medications on the LD50 of A10, combination experiments were also performed. A detailed description of the methods used can be found in Appendix 7. The pharmacology and toxicology studies illustrate that A10 can be administered to animals under conditions having little if any adverse effect on the animal, particularly when PBTE:D5W formulations are used. Other suitable formulations can be obtained by one skilled in the art using this application as a guide.

Effect of A10 on Blood Cells

Many cancer therapeutics are cytotoxic in nature and have profound effects on blood cells resulting in cytopenia. The effects of A10 on the number of red blood cells, white blood cells, and the percent of lymphocytes versus polymorphonuclear cells were examined.

A10 at 15 mg/kg/day, did not appear effect blood differentials over a 21 day period for drug delivered in DMSO, PBTE or PBTE:D5W (1:1). Drug delivered in PBTE:D5W at 20 or 25 mg/kg/day did not affect the number of RBCs, WBCs or percent lymphocytes:neutrophils. However, drug delivered in PBTE alone at 30 mg/kg/day showed a slight decrease in WBCs after 2–3 weeks of treatment. Animals given 40 mg/kg/day showed both anemia and leukopenia after several weeks of treatment when given A10 in PBTE alone. No effects on blood cell were observed when A10 was administered in PBTE:D5W even after 100 days of treatment.

Effects of A10 on Body Weight

The effect of daily administration of A10 (20 mg/kg/day) on body weight was examined over a 100 day period. A10 had an initial effect on weight gain compared to controls. However, after several weeks, the animals gained weight at a rate similar to untreated or vehicle-treated animals. Over the treatment period, no mortality was observed. In addition there were no effects on blood differentials and no observable effects on major organ histopathology, including heart, liver, lung, kidneys, spleen, long bone, stomach, mesenteric lymph node, small and large intestine and pancreas.

Determination of $LD_{50}$

The lethal dose of A10 for 50% of animals ($LD_{50}$) was determined for both athymic mice (BALB/c, nu/nu, female) and BALB/c mice (male and female) using a number of dosing regimens. As shown in Table XXV, the $LD_{50}$ of A10 ranged from 83–145 mg/kg.

The effects of Dilantin® (phenytoin sodium for injection), an anti-convulsant agent, and Decadron® (dexamethasone sodium phosphate for injection), an anti-inflammatory agent, on the $LD_{50}$ of A10 were also determined (Table XXV). The $LD_{50}$ for A10 following pretreatment of animals with Decadron® or Dilantin® was 94 and 144 mg/kg, respectively.

TABLE XXV

Determination of A10 $LD_{50}$ in mice

| Dose/Regimen | Strain, sex | $LD_{50}$ (mg/kg) |
|---|---|---|
| single dose | athymic, f | 145 |
| every 4 days × 4 | athymic, f | 75 |
| every 7 days × 4 | athymic, f | 100 |
| single dose | BALB/c, f | 83 |
| single dose | BALB/c, m | 107 |
| single dose with Decadron ® pretreatment | BALB/c, f | 94 |
| single dose with Dilantin ® pretreatment | BALB/c, f | 144 |

Table XXV. Decadron® was administered at 1.5 mg/kg/day for 7 days prior to administration of a single dose of A10. Dilantin® was administered at 20 mg/kg/day for 7 days prior to administration of a single dose of AIO. The LD50 was calculated from a plot of % mortality versus dose (log M) using a four parameter logistic equation. f=female, m=male, n=5 animals per group.

Example 14
In vivo Inhibition of Tumor by a Mutated PDGF-R Receptor

This example illustrates the use of nucleic encoding a truncated PDGF-62 receptor to inhibit in vivo tumor growth. C6 rat glioma cells were infected with retroviruses; carrying a mutant gene for the human PDGF-B receptor. Seven G418-selected clones were screened for expression of the truncated receptor by Western blotting with an antibody that recognizes the extracellular domain of the human receptor but does not cross-react with the wild type rat receptor. Two clones, HiMut.1 and HiMut.2, express high levels of a protein with the predicted molecular weight for the receptor lacking most of the intracellular region. Several clones expressed low levels of the truncated receptor; LoMut.1 was chosen for further experiments. HiMut.1 expressed PDGF-R 8.3 fold higher than LoMut.1. Himut.2 expressed PDGF-R 9.4 fold higher than LoMut.1. The isolation and characterization of the clones containing the mutant receptors were carried out as described below.

Cell culture. All culture media, fetal bovine serum (FBS) and chemicals were purchased from Gibco BRL. C6 rat glioma cells were grown in Ham's/F-10 medium supplemented with 5% fetal bovine serum and 2 mM glutamine. COS cells were cultured in 10% fetal bovine serum and 2 mM glutamine in Dulbecco's Modified Eagle's medium (DMEM).

Expression of mutant PDGF-β receptor. A stop codon was introduced by site-directed mutagenesis into the gene for the human PDGF-β receptor directly upstream from the first tyrosine kinase domain. The mutant gene was cloned into a vector under the control of the murine sarcoma virus long terminal repeat (Muller, A. J., et al., *Mol. Cell. Biol.* 11:1785–1792, 1991). Four mg each of this vector and a vector containing the genes required for retroviral virus packaging (Muller, supra) were cotransfected into COS cells ($2\times10^5$ cells/60 mm plate) by calcium phosphate precipitation (Chen, C. A., and H. Okayama, *BioTech.* 6:632–638, 1988). The cells were washed with PBS and refed the following day and conditioned media collected on days 4–6 after transaction. C6 cells ($10^5$ cells/60 mm were infected with dilutions of the conditioned media containing 6 mg/ml Polybrene (Sigma). Two days later, the cells were put into selection with 800 mg/ml G418 (Gibco) and colonies picked when distinguishable. The vector control cells were prepared by the same method but with a vector lacking a gene under the LTR.

Co-immunoprecipitation of wild type and truncated receptors. Vectors control cells and cells expressing high levels of the mutant PDGF-β receptor (HiMut.1) were each seeded with $3\times10^5$ cells/well on 60 well plates. The following day, the media was changed for 0.5 ml 3% FBS in -cys -met DMEM (ICN) containing 100 mCi/ml Trans$^{35}$S-label (ICN). The cells were incubated at 37° C. for 16 hrs. They were washed twice with binding buffer (0.1% BSA, 10 mg/ml $CaCl_2.2H_2O$, 10 mg/ml $MgSO_4.7H_2O$, 10 mg/ml aprotinin and 0.2 mM PMSF in PBS), and 0.5 ml binding buffer or 0.5 ml 20 ng/ml PDGF-BB (Collaborative Research Inc.) in binding buffer was added to each well. The cells were incubated at 4° C. for 4 hrs, washed twice with PBS and lysed with 0.5 ml 1% Triton X-100 in HNTG (20 mM HEPES (pH 7.5), 150 mM NaCl, Triton X-100, 10% glycerol, 10 mg/mlh each of aprotonin, leupeptin and pepstatin, and 0.2 mM PMSF). PDGF-BB was included in the lysis buffer of cells that had been treated with PDGF. The lysates were spun at 100,000×g for 30 min at 4° C. The supernatants were transferred to new tubes and precleared with Protein A-agarose (Vector Laboratories). SDS was added to a final concentration of 0.1% to 2 PDGF-treated samples for each cell line. Duplicate samples were immunoprecipitated with either an antibody that recognizes the C-terminus of the wild type rat at receptor (UBI anti-PDGF-β receptor) or the human mutant receptor (Genzyme anti-PDGF-β receptor). Rabbit anti-mouse IgG was used as a secondary antibody for the samples incubated with the Genzyme anti-receptor. The complexes were precipitated with Protein A-agarose and washed 5 times with 0.1% Triton X-100 in HNTG. The proteins were separated by SDS-polyacrylamide gel electrophoresis on 7.5% gels under reducing conditions. The gels were fixed, treated with Amplify (Amersham) and exposed to X-ray film for 3 days.

Western blotting. Each cell line was plated in multiple wells at $5\times10^5$ cells/well on 6-well plates. The following day they were fed with 1% FBS in MCDB 105 (UCSF Cell Culture Facility) and incubated for 24 hrs in a 0% $CO_2$ environment. PDGF-AA or -BB (Collaborative Research Inc.) was added to one well of each clone to the desired final concentration. After incubating for 7 min at room temperature, the cells were washed with PBS and lysed with 50 mM Tris-HC1 (pH 7.4), 1% nonidet P-40, 10% glycerol, 2 mM EDTA, 10 mM sodium pyrophosphate, 10 mg/ml each aprotinin and leupeptin, 1 mM PMSF and 1 mM sodium orthovanadate. Equal volumes of each lysate were run on multiple 7.5% SDS polyacrylamide gels and transferred to nitrocellulose (Schleicher & Schuell). The membranes were blocked with 5 % instant nonfat milk in Tris-buffered saline/0.05% Tween-20 (TBST-T). Duplicate membranes were incubated with either polyclonal anti-phosphotyrosine 1:3000 or anti- PDGF-β receptor (UBI) 1:1000 in blocking buffer. The secondary antibody was horseradish peroxidase-conjugated goat anti-rabbit IgG (Sigma) 1:1000. To detect the truncated receptor, a monoclonal antibody against the extracellular domain of the human PDGF-b receptor (Genzyme) diluted 1:500 was utilized. The secondary antibody used was peroxidase-conjugated rabbit anti-mouse IgG (ICN) 1:1000. ECL (Amersham) was used for detection on all blots. Relative band areas were determined with a Molecular Devices Computing Densitometer. Basal levels of phosphorylation were subtracted from each point.

Adherent growth of cell lines. To determine growth densities, each cell line was seeded with $10^4$ cells/well on 5 24-well plates with triplicate samples in 1% or 5% FBS in Ham's/F-10 medium. The media was changed every 3 days. Every 2 days, the cells on one plate were trypsinized and counted on a Coulter counter. To determine cloning efficiencies, 100 cells of each cell line were plated on three 10 cm plates in 1% or 5% FBS in Ham's/F-10 medium. The media was changed every 3 days for about 12 days. The colonies were fixed, stained with methylene blue and scored.

Anchorage-independent growth of cell lines (soft agar assay). A base layer was made in 35 mm plates with 0.8% SeaPlaque agarose (FMC BioProducts), 1% FBS 2 mM glutamine, 1 mM sodium pyruvate, 10 mM HEPES and nonessential amino acids. Cells were suspended in 0.4% agarose containing the other ingredients listed above and the desired concentration of PDGF-BB (Collaborative Research Labs). The suspension was plated on the base layer with 3000 cells/plate. They were incubated for 2 weeks in a humidified chamber with 5% $CO_2$. Colonies were scored visually or with an automated Omincon 3800™ tumor colony counter.

Growth of cell lines in nude mice. Cells were expanded in roller bottles, trypsinized and resuspended in PBS. They were counted and the volume adjusted to $3\times10^7$ cells/ml. For each cell line, 4 to 8 athymic nude mice (Simonsen Labs) were injected subcutaneously with 100 ml ($3\times10^6$ cells). Tumor volumes were measured with calipers twice a week for 18 to 21 days.

Immunohistochemical staining of tumor sections. Tumors were resected from the mice and frozen in OCT (Miles Lab). Five mm thick sections were cut and fixed with acetone. The sections were blocked with 10% normal goat serum prior to incubation with 20 mg/ml biotinylated-anti-human PDGF-β receptor (Genzyme antibody, biotinylated by Molecular Probes). Peroxidase-conjugated streptavidin (Caltag) 1:100 and diminobenzidine (Sigma) with $H_2O_2$ were used for detection. For a negative control, a biotinylated monoclonal antibody to an unrelated protein was used at the same protein concentration as the anti- PDGF-β receptor. The counter stain was Harris hematoxylin (Anatech).

Using the retroviral expression system described above, a truncated PDGF-β receptor was introduced into rat C6 glioma cells. In G418-resistant clones expressing the mutant receptor, PDGF-BB-induced tyrosine phosphorylation of the wild type receptor was significantly reduced. Furthermore, these cells grew to lower density and formed smaller colonies in culture and in soft agar than the parental C6 cells.

Cells expressing the truncated receptor were significantly impaired in their ability to grow in nude mice. After 21 days, the volumes of the tumors from HiMut.1 and HiMut.2 were only 12–16% of the size of the tumors from the parental cells. Tumors derived from the C6 parental cells and vector control cells were essentially identical indicating that G418 selection of the vector control cells did not affect their ability to grow in nude mice. Tumors derived from HiMut.1 gave very dark immunological staining in at least 10% of the cells. HiMut.2-derived tumors were stained in 45–85% of the cells.

The presence of the truncated PDGF-β receptor was also confirmed by Western blotting of lysed tumor sections.

Thus, the truncated PDGF-B receptor was expressed in vivo for up to 21 days and it had to be present in at least 10% of the cells to be inhibitory. These studies demonstrate the usefulness of dominant negative mutants of PDGF-R to inhibit growth of tumors characterized by inappropriate PDGF-R activity in vivo.

Example 15
Cellular Culture and In vitro Affects of Other Compounds

This example illustrates the effect of featured compounds, other than A10 and B11, on tumor growth in cell culture or in vivo. PDGF-R activity, C6 SRB, and in vivo efficacy were measured using the procedures described in the appendices above. The results are shown in Table XXVI and XXVII. These results are preliminary data. One skilled in the art can improve the efficacy of the different compounds using factors known in the art such as different dosing regimens.

TABLE XXVI

| Compound | U1242 KINASE IC$_{50}$ ($\mu$M) | C6 SRB IC$_{50}$ ($\mu$M) | LD$_{10}$ (mg/kg) | C6 in vivo EFFICACY (% at mg/kg) | p Value | Comments |
|---|---|---|---|---|---|---|
| P10 | 3.0 (W) | 12 | | | | |
| J10 | 1 (W) >50 | 12 | 171 | 73% at 40 | | 100% mortality at d18 |
| G13 | 1.5 | >50 | not tested | 12% at 15 | | 0% mortality |
| G14 | 0.8 (W) | >50 | not tested | 36% at 15 | 0.285 | 0% mortality at d14 |
| G21 | 6.0 (W) >50 | >12 >12 | >200 no deaths | no effect at 40 | | 0% mortality |
| G22 | 0.9 (W) 14 | >6 >6 | 25 | no effect at 20 | | 0% mortality only one dose tested in MTD due to solubility problems |
| P16 | 0.8 >50 | 17 | >400 no deaths | no effect at 60 | | 0% mortality |
| F10 | 45 (W) | >12.5 | | | | |
| G24 | 0.6 5 | 1 2.2 | >200 no deaths | no effect at 20 no effect at 40 no effect at 60 | | 0% mortality 12.5% mortality at d15 100% mortality at d10 |
| G25 | 1.0 | 50 | | | | |
| P13 | 1.2 | >100 | | | | |
| P17 | 0.8/3.0 >50 | 12 | >100 no deaths | | | only one dose tested in MTD due to solubility problems |
| H10 | 25 (W) >50 | 13 | 75 | 52% at 30 | 0.006 | 14.3% mortality at d17 |
| H12 | >250 (W) 25 (W) | 19 | | | | |
| H13 | >50 >50 | 20 10.5 | >400 no deaths | 0% at 40 41% at 100 | 0.12 | 0% mortality 0% mortality |
| E15 | 5.0 (W) 10 (W) >50 | 4.4 | >400 no deaths | 66% at 15 58% at 50 0% at 100 | 0.019 0.1 | 0% mortality 12.5% mortality at d15 100% mortality at d8 |
| P19 | | >50 | | | | |
| P21 | | >25 | | | | |
| J11 | 3.1 | 14 | | | | |
| P21 | 93 | >25 | | | | |

W = done in Western assay

TABLES XXVII

| Compound | U1242 KINASE IC$_{50}$ ($\mu$M) | C6 SRB IC$_{50}$ ($\mu$M) | LD$_{10}$ (mg/kg) | Comments |
|---|---|---|---|---|
| A13 | | >>25 | >200 no deaths | ~30% inhibition at 25 $\mu$M |
| P22 | | >>25 | | ~10% inhibition at 25 $\mu$M |
| P23 | | 18 | | |
| P24 | | 14 | | |
| G28 | 16.4 (scndry) | 4.5 | | |

TABLES XXVII-continued

| Compound | U1242 KINASE IC$_{50}$ ($\mu$M) | C6 SRB IC$_{50}$ ($\mu$M) | LD$_{10}$ (mg/kg) | Comments |
|---|---|---|---|---|
| G29 | 23.2 | >13 | | killed all cells at >12.5 82 M |
| G30 | 32.5 | 2 | | |

W = done in Western assay

Example 16
Combination Therapy

Studies were conducted to look at the effect on tumor growth when PDGF-R inhibitors are used in combination with known cytotoxic drugs currently used to treat cancer. In separate experiments CALU-6 cells and MCF-7/HER2 cells were implanted subcutaneously in nude mice. In one experiment the mice were then treated with A10 alone, cisplatin alone or a combination of cisplatin and A10. A10 was given intraperitoneally twice weekly at 5/mh/kg. Cisplatin was given in a single intraperitoneal dose of 5/mg/kg on day two.

In the mice implanted with MCF-7/HER2 cells, the combination of A10 and cisplatin was better at inhibiting tumor growth than cisplatin alone or no treatment, but did not enhance tumor suppression compared to A10 alone. However, in the mice implanted with CALU-6 cells, the combination of A10 and cisplatin resulted in a significant suppression of tumor growth compared to A10 alone, cisplatin alone or no treatment.

In a second experiment with CALU-6 cells, mice were treated with A10, cisplatin or VP-16 alone (10/mg/kg on days 4, 7 and 10) or the combination of cisplatin and VP-16 or A10, cisplatin and VP-16. The combination of A10, cisplatin and VP-16 was better at suppressing tumor growth than either drug alone or the combination of cisplatin and VP-16.

Example 17
Chemical Synthesis

Some of the compounds of this invention may be prepared by employing procedures known in the literature starting from known compounds or readily made intermediates. Quinoxalines compounds were prepared by either 1) reacting 1,2 aromatic diamine with α-ketoaldehyde or a-diketone, or 2) an exchange reaction of α-bis thiosemicarbazones and a 1,2-diamine in the presence of an acid catalyst. In the following preparations the aromatic diamine was obtained commercially or prepared as described in the example. In examples where the reaction solvent is not specified, the reaction was carried out in ethanol-acetic acid. Some quinoxalines synthesized using this solvent were isolated as acid addition complexes with one molecule acetic acid, band on elemental analysis. Reactions in ethanol alone, followed by solvent evaporation and recrystallization, gave a cleaner product and higher yield.

Group 1 Compounds
A10 a10 can be prepared as in European Patent Application 0 013 376 A2. Alternatively A10 can be prepared as follows:

Step 1

Preparation of acetoacetic acid-(4-trifluoromethyl) aniline

A mixture of 4-trifluoromethylaniline (.16.1 g, 0.1 mol), 2,2,6-trimethyl-4H-1,3-dioxin-4-one (purity 95%; 14.97 g, 0.1 mol), and xylene (20 ml) was heated to reflux for 30 minutes in a bath preheated to 150° C. The resulting dark solution was cooled to room temperature to crystalize the product. The crystals were filtered and collected. More material was obtained from mother liquors (the solution remaining after the initial crystallization and filtration). The yield of crude anilide was 17.75 g (72%), the anilide had a melting point of 153–154° C.

Step 2

Preparation of 2-Ethoxymethyleneacetoacetyl-(4-trifluoromethyl)aniline

Acetoacetyl-(4-trifluoromethyl)aniline (14.11 g, 57.6 mmol), triethoxymethane (9.43 g, 63.4 mmol), and acetic anhydride (16.30 ml, 173 mmol) were mixed together and heated to reflux for 90 minutes. The resulting dark solution was evaporated to dryness. The residue was resuspended in benzene/isooctane and the produce was crystallized. More material was obtained from mother liquors. Yield of pure product was 11.93 g (72%), mp. 120–122° C.

Step 3

Preparation of A10

2-Ethoxymethyleneacetoacetyl-(4-trifluoromethyl)aniline (3.01 g, 10.4 mmol) in ethanol (6 ml) was slowly added to an ice cooled solution of hydroxylamine hydrochloride (0.77 g, 11.0 mmol) in 2 M NaOH (5.5 ml). The mixture was heated to reflux for 1 hour, cooled to room temperature and evaporated to dryness. The residue was resuspended, and distributed between ethyl acetate and water. The organic layer was separated, extracted with water, dried by sodium sulfate and the solvent was evaporated. The residue was resuspended in toluene and crystallized to yield a solid residue (2.45 g, 87%) of A10 having a melting point of 166–167° C.

A11

Preparation of 5-Methyl-isoxasole-4-carboxylic acid-(3-trifluoromethyl)-anilide was carried out in three steps:

Preparation of 5-Methyl-isoxazole-4-carboxylic acid-(3-trifluoromethyl)-anilide was carried out in three steps:

a) Preparation of Acetoacetic acid-(3-trifluoromethyl)-anilide.

In a 25 ml round bottom flask equipped with Claisen distillation head and magnetic stirrer 4 g (18.6 mM) of (α,α,α-Trifluoro-p-toluidine, 3.71 g (24.8 mM, 1 equiv.) 95% 2,2,6-trimethyl-4H-1,3-dioxin-4-one, 112 ml diethanolamine and 12.4 ml xylene was combined. The temperature of the mixture was raised to 110° C., and the mixture was stirred at this temperature for 6 hours while acetone was distilled off from the system. The progression of the reaction was monitored by TLC (plate Merck Kieselgel 60 F$_{254}$ eluent: Petroleum ether (90–100° C. fraction):acetone 2:1 visualization with 5% PMA in EtOH).

After 6 hours the xylene was distilled off at 20 Hgmm and the residue was purified with medium pressure (2 atm) liquid chromatography using Silica gel 60 as fixed phase and petroleum ether (90–110° C. fraction):acetone 2:1 as eluent.

The product fractions at R$_f$=0.3 were collected—using the TLC system used for the monitoring of the reaction—and after stripping the solvent, 3.82 g of Acetoacetic acid—(3-trifluoromethyl)-anilide was isolated. Melting point: 91–92° C.

$^1$H-NMR (ppm, acetone-d6)

| ArH | 7.36–7.87 | 4H | (m) |
|------|-----------|----|-----|
| NH | 9.41 | 1H | (s) |
| CH$_2$ | 3.62 | 2H | (s) |
| CH$_3$ | 2.64 | 3H | (s) | b) Preparation of 2-propenamide, 2-acetyl-3-ethoxy-N-[(trifluoromethyl)phenyl]

In a dried (120° C., 30 min) 50 ml round bottom flask equipped with magnetic stirrer, thermometer, rubber septum and Argon balloon on a T stopcock, 1.0 g (4.1 mM) Acetoacetic acid-(3-trifluoromethyl)-anilide, 0.85 g (5.7 mM) orthoformic acid triethylesther 1.37 g acetic anhydride and 450 mg dry zinc chloride was combined. The mixture was stirred in argon atmosphere at 60° C. for 30 minutes. The progress of the reaction was monitored by TLC (plate Merck Kieselgel 60 F$_{254}$, eluent: Petroleum ether (90–110° C. fraction):acetone 5:1. If the reaction was not complete after 30 minutes, a further 0.85 g (5.7 mM) of orthoformic acid triethylesther was added.

The reaction mixture gradually turned brown. After the completion of the reaction, the reaction mixture was stripped in vacuo, the residue was dissolved in ethyl acetate, which was washed with water, the organic phase was dried with magnesium sulfate then filtered and the ethyl acetate was distilled off in vacuo. The 1.16 g crude product was purified with medium pressure (2 atm) liquid chromatography using Silica gel 60 as fixed phase and petroleum ether (90–110° C. fraction):acetone 5:1 as eluent.

The product fractions at R$_f$=0.231 were collected—using the TLC system used for the monitoring of the reaction—and after stripping the solvent, 0.46 g of 2-propenamide, 2-acetyl-3-ethoxy-N-[(trifluoromethyl)phenyl] was isolated. Melting point: 100.5° C.

| ARH | 7.29–8.00 | 4H | (m) |
|-----|-----------|----|-----|
| NH | 11.25 | 1H | (s) |
| CH= | 8.46 | 1H | (s) |
| EtCH$_2$ | 4.37 | 2H | (s) |
| EtCH$_3$ | 1.45 | 3H | (s) |
| AcMe | 2.48 | 3H | (s) | c) Preparation of 5-Methyl-isoxazole-4-carboxylic acid-(3-trifluoromethyl)-anilide In a 25 ml round bottom flask equipped with magnetic stirrer and thermometer 0.11 g (1.58 mM) of hydroxylamine hydrochloride was dissolved in 0.5 ml of water and to this solution 64 mg (1.6 mM) sodium hydroxide was added in 0.5 ml of water. To this solution 2.2 ml of methanol was added and at room temperature 0.44 g (1.5 mM) 2-propenamide, 2-acetyl-3-ethoxy-N-[(trifluoromethyl) phenyl] was added. The progress of the reaction was monitored by TLC (plate Merck Kieselgel 60 F$_{254}$ eluent: Petroleum ether (90–110° C. fraction):acetone 4:1, visualization with 5% PMA in EtOH). After completion of the reaction, the reaction mixture was concentrated in vacuo and the residue was dissolved in ethyl acetate. The organic phase was washed with water, dried with magnesium sulfate, filtered and concentrated. The obtained 0.51 g crude product was purified with medium pressure (2 atm) liquid chromatography using Silica gel 60 as fixed phase and petroleum ether (90–110° C. fraction):acetone 4:1 as eluent.

The product fractions at R$_f$=0.162 were collected—using the TLC system used for the monitoring of the reaction—and after the stripping of the solvent, 0.22 g of 5-Methyl-isoxasole-4-carboxylic acid-(3-trifluoromethyl)-anilide was isolated. Melting point: 115–120° C.

$^1$H-NMR (ppm, acetone-d6)

| ArH + NH | 7.42–7.88 | 4H | (m) |
|----------|-----------|----|-----|
| CH= | 8.50 | 1H | (s) |
| CH | 8.50 | 1H | (s) |

A12

A12 can be prepared as described by Patterson et al., *J. Med Chem.* 35:507–510 (1992).

A13

N-trifluoromethlyphenyl 3,5-dimethylisoxazole-4-carboxamide

A mixture of 320 mg of 3,5-dimethylisoxazole-4-carbonylchloride and 1 ml of 4-trifluoromethlyaniline in 2 ml of dichloromethane was stirred at room temperature overnight. The mixture was then worked up with ethyl acetate and water. The crude was crystallized with ethanol and water to provide 330 mg of N-trifluoromethlyphenyl 3,5-dimethylisoxazole-4-carboxamide.

Group 2 Compounds

B10

B10 was synthesized in two steps.

a) Synthesis of cyanoacetyl-(4-nitro)anilide 1.38 g (10 mmol) 4-nitroaniline was dissolved in 30 ml of absolute pyridine, then cooled to −30° C., 0.43 ml (5 mmol) phosphorus trichloride was added dropwise with continuous stirring to avoid increasing the temperature above −20° C. After 0.5 hour 0.85 g cyanoacetic acid was added, and the solution was stirred for 0.5 hour at −20° C. then 12 hours at room temperature.

The solvent was evaporated in vacuum. The residue was covered with 1N HCl and extracted with ethylacetate. The ethylacetate solution was dried over Na$_2$SO$_4$, filtered and evaporated. The residue was triturated with ether filtered and dried in vacuo. 1.70 g (83%) product yield was obtained. The product had the following characteristics:

Melting point: 81–83° C.

R$_F$: 0.95 (hexane-EtOAc; 1:1)

b. Acetylation of cyanoacetyl-(4-nitro)anilide.

0.82 g (4 mmol) cyanoacetyl 4-nitroanilide was dissolved in 2 ml absolute pyridine, followed by the addition of 20 mg 4-aminopyridine catalyst and 0.50 ml tetramethylguanidine. The reaction mixture was
stirred while the nitroanilide dissolved. 5 ml of acetic anhydride was then dropped in at 0° C.

After 2 days the pyridine was evaporated, ethylacetate was added and the organic layer was extracted with 5% NaHCO$_3$ solution, in 1N HCl, and water. The organic layer was dried over Na$_2$SO$_4$ and evaporated. The residue was crystallized from ether and 210 mg (21% yield) of product was obtained. The product had the following characteristics:

Rf=0.35 (EtoAc)

Melting point: 260° C.

B11

B11 was synthesized using two different methods: method A and method B.

Method A

A mixture of 27 grams of A10 in 150 ml of ethanol was combined with 16.2 grams of 1,8-diazabicyclo[5.4.0]undec-7-ene. The reaction mixture was then stirred at room temperature for 30 minutes and ethanol was evaporated off. The resulting solid was suspended in 500 ml of ethyl ether and combined with 200 ml of 0.6 N hydrochoric acid solution. All the solids was suction filtered, washed with 200 ml ethanol and suction dried to provide 25 grams product.

Method B

2-Butenamide, 2-cyano-3-hydroxy-N-[(4-trifluoromethyl)phenyl] ($C_{12}H_{19}F_3NO_3$) was prepared in two steps as follows:

a) Preparation of Cyanoacet-(4-trifluoromethyl)-anilide

A mixture of 3 g (18.6 mM) α,α,α,-Trifluoro-p-toluidine and 3.37 g (29.8 mM, 1.6 equivalent) cyanoacetic acid ethyl ester in a 50 ml flask, equipped with magnetic stirrer, thermometer and nitrogen vent, was stirred on a 180° C. oil bath for 5 hours. The progress of the reaction was monitored by TLC (plate Merck Kieselgel 60 $F_{254}$, eluent: Petroleum ether (90–110° C. fraction):acetone 1:1). The reaction mixture was purified with medium pressure (2 atm) liquid chromatography using Silica gel 60 as fixed phase and petroleum ether (90–110° C. fraction):acetone 1:1 as eluent.

The product fractions were collected—using the TLC system used for the monitoring of the reaction—and after stripping the solvent, 2.11 g of Cyanoacet-(4-trifluoromethyl)-anilide was isolated. Melting point: 192–194° C.

| ArH | 7.68–7.85 | 4H | (dd) |
|---|---|---|---|
| NH | 9.84 | H | (s) |
| $CH_2$ | 3.90 | 2H | (s) | b) Preparation of 2-Butenamide, 2-cyano-3-hydroxy-N-[(4-trifluoromethyl)phenyl]

In a 50 ml round bottom flask equipped with magnetic stirrer, thermometer, a rubber septum and a T stopcock (with vacuum and Argon blanket balloon joints), 1.78 g (0.89 g, 37.1 mM) 50% NaH oily dispersion was suspended in 4 ml dry (from $P_2O_5$) acetonitrile. The suspension was cooled to 10° C. and while stirring at this temperature 2.72 g (11.9 mM) Cyanoacet-(4-trifluoromethyl)-anilide was added dissolved in 25 ml dry (from $LiAlH_4$) tetrahydrofuran in 10 minutes. The reaction mixture turned yellow, and was cooled down after the addition to −10° C., and then 1.05 g (13.11 mM, 1.1 equiv.) Acetylchloride was added in 20 minutes. During the addition, the temperature of the reaction mixture can not be higher than −5° C. The progress of the reaction was monitored by TLC (plate Merck Kieselgel 60 $F_{254}$, eluent: Petroleum ether (90–110° C. fraction):acetone 1:1).

When the reaction was complete, the reaction mixture was stirred at 0° C. for 30 minutes, at 350° C. for 30 minutes and at 65° C. for another 30 minutes, then the reaction mixture was stripped in vacuo. The residue was dissolved in 30 ml distilled water, charcoaled at 80° C. and filtered. The resulting pale yellow filtrate was acidified with a 10% hydrochloric acid solution, the precipitated crystals were filtered, washed with water and dried. The crude crystals (2.51 g) were purified with medium pressure (2 atm) liquid chromatography using Silica gel 60 as fixed phase and petroleum ether (90–110° C. fraction):acetone 1:1 as eluent.

The product fractions at Rf=0.138 were collected—using the TLC system used for the monitoring of the reaction—and after stripping the solvent, 1.99 g of 2-Butenamide, 2-cyano3-hydroxy-N-[(4-trifluoromethyl)phenyl] was isolated. TLC petroleum ether (90–110° C.)/acetone 1/1=0.138. 1 H-NMR (ppm, DMSO-d6)

| ArH | 7.65–7.78 | 4H | (dd) |
|---|---|---|---|
| NH | 10.85 | 1H | (s) |
| $CH_3$ | 2.26 | 3H | (s) |
| OH | 6.39 | 1H | (s) |

B12

Preparation of 2-Propenamide, 2-cyano-3-hydroxy-3-(4-fluorophenyl)-N-[(4-trifluoromethyl)phenyl] ($C_{17}H_{10}F_4N_2O_2$ MW:350.3) was carried out as follows a) Preparation of Cyanoacet-(4-trifluoromethyl)-anilide A mixture of 3 g (18.6 mM) α,α, α,-trifluoro-p-toluidine and 3.37 g (29.8 mM, 1.6 equivalent) cyanoacetic acid ethyl ester in a 50 ml flask, equipped with a magnetic stirrer, thermometer and nitrogen vent, was stirred on a 180° C. oil bath for 5 hours. The progress of the reaction was monitored by TLC (plate Merck Kieselgel 60 $F_{254}$, eluent: Petroleum ether (90–110° C. fraction):acetone 1:1). The reaction mixture was purified with medium pressure (2 atm) liquid chromatography using Silica gel 60 as fixed phase and petroleum ether (90–110° C. fraction):acetone 1:1 as eluent.

The product fractions were collected and after the stripping of the solvent, 2.11 g of cyanoacet-(4-trifluoromethyl)-anilide was isolated. The product had the following characteristics: Melting point: 192–194° C.

$^1$H-NMR (ppm, acetone-d6)

ArH 7.68–7.85, 4H (dd)

| ArH | 7.68–7.85, | 4H | (dd) |
|---|---|---|---|
| NH | 9.84 | 1H | (s) |
| $CH_2$ | 3.90 | 2H | (s) | b) Preparation of 2-Proponamide, 2-cyano-3-hydroxy-3-(4-fluorophenyl)-N-[(4-trifluoromethyl)phenyl]

In a 50 ml round bottomed flask equipped with magnetic stirrer, thermometer, a rubber septum and a T stopcock (with vacuum and Argon blanket balloon joints) 0.55 g (0.275 g, 11.4 mM) 50% NaH oily dispersion was suspended in 1 ml dry (from $P_2O_5$) acetonitrile. The suspension was cooled to 10° C. and under stirring at this temperature 1 g (4.4 mM) cyanoacet-(4-trifluoromethyl)-anilide, dissolved in 10 ml dry (from $LiAlH_4$) tetrahydrofuran, was added in 10 minutes. The reaction mixture was then cooled down to −10° C. and at this temperature 0.77 g (4.8 mM, 1.1 equiv.) 4-fluorobenzylchloride was added in 20 minutes. During the addition the temperature of the reaction was monitored by TLC (plate Merck Kieselgel 60 $F_{254}$, eluent: Petroleum ether (90–110° C. fraction):acetone 1:1).

The reaction mixture was then stirred at 0° C. for 30 minutes, at 35° C. for 30 minutes and at 65° C. for another 30 minutes, then the reaction mixture was stripped in vacuo. The residue was dissolved in 30 ml distilled water, charcoaled at 80° C. and filtered. The resulting pale yellow filtrate was acidified with 10% hydrochloric acid solution, the precipitated crystals were filtered, washed with water and dried. Crude crystals (2.47 g) were purified with medium pressure (2 atm) liquid chromatography using Silica gel 60 as fixed phase and petroleum ether (90–110° C. fraction):acetone 1:1 as eluent.

The product fractions at Rf=0.216 were collected and after the stripping of the solvent, 1.05 g of 2-Propenamide, 2-cyano-3-hydroxy-3-(4-fluorophenyl)-N-[(4-trifluoromethyl)phenyl] was isolated. The product had the following characteristics:

Melting point: 195° C. (dec).

$^1$H-NMR (ppm, acetone-d6)

| ArH | 7.36–8.13 | 8H | (m) |
| NH | 9.5 | 1H | (s) |
| OH | 16.5 | 1H | (s) |

B13

Preparation of 2-Propenamide, 2-cyano-3-hydroxy-3-cyclohexyl-N-[(4-trifluoromethyl)phenyl] ($C_{17}H_{17}F_3N_2O_2$ MW: 338.3) was carried out as described for B12 substituting 0.71 g (4.8 mM, 1.1 equiv.) cyclohexylacetyl-chloride for 4-fluorobenzoylchloride. The resulting product had the following characteristics:

TLC: $R_f$=0.265 (petroleum ether (90–110° C.):acetone, 1:1)

Melting point: 212° C. (dec.)

B14

Preparation of 2-cyano-3-hydroxy-3-(2, 2, 3, 3-tetramethylcyclopropyl)-propanol-4-(trifluoromethyl) anilide was carried out as described for B12 above using 2, 2, 3, 4-tetramethylcyclopropylcarboxyl chloride for 4-fluorobenzoylchloride.

B15

Preparation of 2-Propenamide, 2-cyano-3-hydroxy-3-(pentafluorophenyl)-N-[(4-trifluoromethyl)phenyl] was carried out as described for B12 substituting 1.5 g (6.51 mM, 1.1 equiv.) pentafluorobenzoylchloride for 4-fluorobenzoylchloride. The resulting product had the following characteristics:

TLC: $R_f$=0.360 (petroleum ether (90–110° C.):acetone, 1:1)

Melting point: 157–158° C.

B16

Preparation of 2-Propenamide, 2-cyano-3-hydroxy-3-((3-phenoxy)phenyl)-N-[(4-trifluoromethyl)phenyl] ($C_{23}H_{15}F_3N_2O_3$ MW: 424.4) was carried out as described for B12 substituting 1.65 g (4.8 mM, 1.1 equiv) 3-phenoxybenzoyl chloride for 4-fluorobenzoylchloride. The resulting product had the following characteristics:

TLC: $R_f$=0.300 (petroleum ether (90–110° C.):acetone, 1:1)

Melting point: 197–198° C.

B17

Preparation of 2-Butenamide, 2-cyano-3-hydroxy-4-phenyl-N-[(4-trifluoromethyl)phenyl] was carried out as described for B12 substituting 0.68 g (4.8 mM, 1.1 equiv.) phenyl-acetyl chloride for 4-fluorobenzoylchloride. The resulting product had the following characteristics:

TLC: $R_f$=0.165 (petroleum ether (90–110° C.):acetone, 1:1)

Melting point: 156–158° C.

B18

Preparation of 2-Hexeneamide, 2-cyano-3-hydroxy-5-methyl-N-[(4-trifluoromethyl)phenyl] ($C_{15}H_{15}F_3N_2O_2$ MW: 312.3) was carried out as described for B12 substituting 0.58 g (4.8 mM, 1.1 equiv.) isovalerylchloride for 4-fluorobenzoylchloride. The resulting product had the following characteristics:

TLC: $R_f$=0.323 (petroleum ether (90–110° C.):acetone, 1:1)

Melting point: 161–163° C.

B19

Preparation of 2-Butenamide, 2-cyano-3-hydroxy-4,4-diphenyl-N-[(4-trifluoromethyl)phenyl] ($C_{24}H_{17}F_3N_2O_2$ MW: 422.4) was carried out as described for B12 substituting 1.12 g (4.8 mM, 1.1 equiv.) diphenylacetyl-chloride for 4-fluorobenzoylchloride. The resulting product had the following characteristics:

TLC: $R_f$=0.354 (petroleum ether (90–110° C.):acetone, 1:1)

Melting point: 195–202° C.

Group 3 Compounds

C10

340 mg (1.5 mM) 1-phenyl-3-amino-4-cyano-5-cyanomethyl-2-pyrazole, 210 mg (1.5 mM) 3,4-dihydroxy benzaldehyde and 4 drops of piperidine in 30 ml ethanol were refluxed for 6 hours. Cooling and filtering gave 145 mg yellow solid. Evaporation of the solvent and trituration with $CH_2Cl_2$-acetone gave another 145 mg yellow solid (56% yield). The product had a melting point of 147° C.

NMR acetone $d_6$ d-7.87 (1H,S, Vinyl), 7.68 (1H,d, J=2.2 Hz, $H_2$) 7.66–7.45 (5H,m, Ph), 7.28 (1H,dd, J=8.3.2.2 Hz, $H_6$). 6.92 (1H,d,J=8.3 Hz, $H_5$).

C11

C11 was synthesized using a two step procedure.

a. Synthesis of 3-amino-4-cyano-5-cyanomethyl-2 pyrozole 2.2 g malononitrile dimer and 0.9 ml $N_2H_4$ in 20 ml of water were heated for 15 minutes at 100° C. Cooling and filtering gave 1.5 g (61% yield) of a white solid having a melting point of 187° C. (NMR acetone $d_6$δ83.88 (s).) (Cf. Carboni et al., *J. Am. Chem. Soc.* 80:2838 (1958), reporting m.p. 197° C.)

b. Condensation with dihydroxybenzaldehyde

To 0.28 g (2 mM) 3,4-dihydroxybenzaldehyde and 1.33 g (2.2 mM) of 3-amino-4-cyano-5-cyanomethyl-2 pyrozole in 20 ml ethanol were added three drops piperidine and the reaction was refluxed 3 hours. Cooling, filtering and washing with ethanol gave 1.3 g (56% yield) of a yellow solid having a melting point of 300° C.

C13

0.7 g, 3 mM, 3,5 di-t-butyl-4-hydroxyaldehyde 0.46 g, 3.1 mM, 3-amino 4 cyano 5-cyanomethyl pyrazole (prepared according to Carboni et al., *J. Chem. Soc.*, 80:2838, 1958) and 40-mg β-alanine were refluxed 15 hours. Cooling and filtering gave 0.5 g, 46% yield, yellow solid, mp. 255° C. NMR $CDCl_3$ δ7.92(1H,S,vinyl), 7.80(2H,S), 5.76(1H,S, OH), 3.75(2H,br,S,NH2), 1.48(18H,S). MS-364(M+1,28), 363(M+,100%), 348 (M—CH3,58), 292(M-56-CH3,31), 147(41), m/e.

Group 4 Compounds

D11

435 mg (3 mM) 3-formyl indole, 300 mg (4.5 mM) 2-thiocarboxamido acetonitrile and 20 mg β-alanine in 30 ml ethanol were refluxed for six hours. Cooling and filtering gave 0.47 g (81% yield of a yellow solid having a melting point of 238° C.).

D12

This was synthesized as for D11 except 1,1,4-tricyano-2-amino-1-propene was used instead of the acetonitrile derivative. The final product had a melting point of 293° C.

D13

This was synthesized as for D11 except 2-carboxamidoacetonitrile was used instead of the acetonitrile derivative. The final product had a melting point of 242° C.

D14

0.29 g (2 mM) 3-formyl indole, 0.29 g (2 mM), 3-amino-4-cyano-5-cyanomethyl-2-pyrazole and 20 mg β-alanine in 30 ml of ethanol were refluxed 4 hours. Cooling and filtering gave 0.34 g (62% yield) of yellow solid having a melting point of 281° C.

NMR acetone $d_6$ 8.52 (1H,S, vinyl), 8.42 (1H,S,$H_2$), 7.79 (1H,m), 7.57 (1H,m), 7.27 (2H,m), 6.17 (1H, br.S, NH).

MS-274 (M+, 100%), 219(14), 91(35), m/e.

D15

0.3 g (1.3 mM) 3-amino-4-cyano-5-cyanomethyl-2-pyrazole, 0.2 g (1.36 mM) of 1-(3-dimethylaminopropyl)-3-formyl indole and 20 mg β-alanine in 20 ml ethanol were refluxed 4 hours. Evaporation, trituration with benzene and filtering gave 0.4 g of yellow solid (94% yield) containing 10% 3-amino-4-cyano-5-cyanomethyl-2-pyrazole. 0.4 g was chromatographed on silica gel (70–220 mesh) eluting with 85:15 methylene chloride:methanol to give 0.12 g of a bright yellow solid having a melting point of 250° C.

NMR acetone $d_6$ δ8.45(1$H_1S_1$ vinyl), 8.37(1$H_1S_1$ $H_2$), 7.78(1$H_1$m), 7.60(1$H_1$m). 7.28(2$H_1$m), 4.47(2$H_1t_1$J=6.8Hz), 2.29(2$H_1t_1$J=6.8 Hz), 2.24(6H,S,N-$(CH_3)_2$). MS-360(M+1, 8%), 359(M+,31), 289(100), 261(15), 144 (6), m/e.

D16

0.4 g (1.7 mM) 3-amino-4-cyano-5-cyanomethyl-2-pyrazole, 0.3 g (1.73 mM) 1-oxo-1-(3,4-dihydroxyphenyl)-2-cyanothane and 20 mg β-alanine in 20 ml ethanol were refluxed 5 hours. Cooling and filtering gave 0.1 g of a brown solid. Preparative chromatography gave 20 mg (3% yield) of an orange solid having a melting point of 115° C.

NMR acetone $d_6$ δ8.72(1H, S, Vinyl), 8.52(1$H_1$ $S_1$ $H_2$), 7.90(1$H_1$m), 7.73(1H,m), 7.40(4H,m), 7.0(1H,d,J=8.2 Hz, $H_5$). 4.57(2H,t,J=7.2 Hz), 2.46(2H,t,J=7.2 Hz), 2.34(6H,S, N$(CH_3)_2$), 2.17(2H, quintet, J=7.2 Hz). ps D17

0.4 g (2 mM) 3-formyl indole, 0.36 g 1-oxo-1-(3,4-dihydroxyphenyl)-2-cyanothane and 3 drops of piperidine, in 25 ml ethanol, were refluxed 6 hours. Workup and trituration with benzene gave 0.36 g of a yellow solid having a melting point of 225° C.

NMR acetone $d_6$ 8.77(1H,S), 7.90(1H,m), 7.70(1H,m), 7.40(4H,m), 7.0(2H,t,J=6.7 Hz), 4.92(2H,t,J=6.8 Hz), 3.26 (2H,t,J=6.8 Hz).

D18

0.29 g, 2 mM, 3-formyl indole, 0.29, 2 mM, 3-amino-4-cyano-5-cyanomethyl-2-pyrazole,and 20 mg β-alanine in 30 ml ethanol were refluxed 4 hours. Cooling and filtering gave 0.34 g, 62% yield, yellow solid, mp. 281° C.

NMR acetone $d_6$ δ8.52 (1H,S, Vinyl), 8.42 (1H,S,$H_2$), 7.79 (1H,m), 7.75 (1H,m), 7.27 (2H,m), 6.17 (1H, Br.S, NH), MS-274 ($M^+$, 100%), 219(14), 91(35), m/e.

D20

80 mg. 0.55 mM, 3-formyl indole, 130 mg, 0.6 mM, 3-amino-4-cyano-5-cyanomethyl-1-phenylpyrazole and 2 drops of piperidine in 10 ml ethanol were refluxed 8 hours. Cooking and filtering gave 120 mg, 62% yield, yellow-green solid, mp. 258° C.

NMR acetone $d_6$ δ8.56(1H,S), 8.52(1H,S), 7.84(1H,m, 7.60–7.25(8H,m).

Group 5

Group 5 compounds were prepared in three steps.

a) Preparation of N-aryl-oxamic acid esters (= Ethyl-oxalyl anilides)

0.025 mol (3.4 ml) diethyl-oxalate and 0.1 mol of the appropriate aniline were mixed together and refluxed at 190° C. for 15 minutes. The resulting solution was cooled and left overnight to crystallize the product. The crystals were filtered, washed with ethanol and extracted with hot ethanol. The insoluble material was filtered off and the solution put in the refrigerator. The resulting crystals were filtered and dried.

TABLE XXVIII

| No. | Subs. | MP ° C. | Formula: | MW | Yield [%] |
|---|---|---|---|---|---|
| 1a | 4-N$(CH_3)_2$ | 116–118 | $C_{12}H_{16}N_2O_3$ | 236.27 | 75 |
| 1b | 3-OH | 184–185 | $C_{10}H_{11}NO_4$ | 209.20 | 86 |
| 1c | 2-OCH$_3$ | 81–82 | $C_{11}H_{13}NO_4$ | 223.23 | 60 |
| 1d | 2-OC$_2H_5$ | 74–76 | $C_{12}H_{15}NO_4$ | 237.26 | 64 |
| 1e | 3-NO$_2$ | 93–96 | $C_{10}H_{10}N_2O_5$ | 238.20 | 53 | b) Preparation of N-aryl-oxamic acid hydrazides (N-aryl-oxamoyl hydrazides)

0.05 mol of the appropriate N-aryl-oxamic acid ester (1a ... 1e) was dissolved in 200 ml of ethanol and slowly added to a well-stirred solution of 7.5 ml (~0.15 mol) hydrazine hydrate in 50 ml ethanol. The mixture was left at room temperature for 48 hours. The resulting heterogeneous solution was refluxed for 15 minutes and filtered the hot solution. After cooling to room temperature the precipitated substance was filtered washed with ethanol and dried.

TABLE XXIX

| No. | Subs. | MP ° C. | Formula: | MW | Yield [%] |
|---|---|---|---|---|---|
| 2a | 4-N$(CH_3)_2$ | 228–232 | $C_{10}H_{14}N_4O_2$ | 222.25 | 83 |
| 2b | 3-OH | 200–202 | $C_8H_9N_3O_3$ | 195.18 | 72 |
| 2c | 2-OCH$_3$ | 165–167 | $C_9H_{11}N_3O_3$ | 209.21 | 67 |
| 2d | 2-OC$_2H_5$ | 152–154 | $C_{10}H_{13}N_3O_3$ | 223.23 | 58 |
| 2e | 3-NO$_2$ | 231–234 | $C_8H_8N_4O_4$ | 224.28 | 49 | c) Preparation of N-aryl-oxamoyl hydrazones

E10

0.001 mol (0.222 g) of N-(4-dimethylamino)-phenyl-oxamoyl hydrazide (2a) was dissolved in 5 ml acetic acid and heated at 100° C. with 0.001 mol (0.138 g) of 3,4-dihydroxy benzaldehyde for 20–25 minutes in the presence of a catalytic amount of sodium acetate. The mixture then cooled and left overnight at room temperature. The separated crystals were filtered off and washed with acetic acid and water.

Yield of pure product was 0.23 g (68%) m.p. 253° C. ($C_{17}H_{18}N_4O_4$, MW:342.36)

Elemental Analysis [%]: Found C, 59.51; H, 5.28; N, 16.25. Calculated C, 59.64; H; 5.30; N, 16.37.

E11

0.001 mol (0.195 g) of N-3-hydroxy-phenyloxamoyl hydrazide (2b) was dissolved in 5 ml acetic acid and heated at 100° C. with 0.001 mol (0.138 g) of 3,4-dihydroxy benzaldehyde for 20–25 minutes in the presence of a catalytic amount of sodium acetate. The mixture was then cooled and left overnight at room temperature. The separated crystals were filtered off and washed with acetic acid and water.

Yield of pure product was 0.142 g (45%) m.p.>260° C. ($C_{15}H_{13}N_3O_5$, MW:315.29).

Elemental Analysis [%]: Found C, 57.06; H, 4.10; N, 13.20. Calculated C, 57.14; H, 4.16, N, 13.33

E12

0.001 mol (0.195 g) of N-3-hydroxyphenyl-oxamoyl hydrazide (2b) was dissolved in 5 ml acetic acid and heated at 100° C. with 0.001 mol (0.122 g) of 2-hydroxybenzaldehyde for 20–25 minutes in the presence of a catalytic amount of sodium acetate. The mixture was then cooled and left overnight at room temperature. The separated crystals were filtered off and washed with acetic acid and water.

Yield of pure product was 0.224 g (75%) m.p. 264–266° C. ($C_{15}H_{13}N_3O_4$, MW:299.29)

Elemental Analysis [%]: Found C, 60.11; H, 4.40; N, 13.76. Calculated C, 60.20; H, 4.38; N, 14.04

E13

0.001 mol (0.21 g) of N-2-methoxyphenyl-oxamoyl hydrazide (2c) was dissolved in 5 ml acetic acid and heated at 100° C. with 0.001 mol (0.138 g) of 3,4-dihydroxy-benzaldehyde for 20–25 minutes in the presence of a catalytic amount of sodium acetate. The mixture was then cooled and left overnight at room temperature. The separated crystals were filtered off and washed with acetic acid and water.

Yield of pure product was 0.21 g (64%) m.p. 232–238° C. ($C_{16}H_{15}N_3O_5$, MW:329.31). Elemental Analysis [%]: Found C, 60.01; H, 4.51; N, 12.59. Calculated C, 58.36; H, 4.59; N, 12.72.

E14

0.001 mol (0.22 g) of N-2-ethoxyphenyl-oxamoyl hydrazide (2d) was dissolved in 5 ml acetic acid and heated at 100° C. with 0.001 mol (0.138 g) of 3,4-dihydroxy-benzaldehyde for 20–25 minutes in the presence of a catalytic amount of sodium acetate. The mixture was then cooled and left overnight at room temperature. The separated crystals were filtered off and washed with acetic acid and water.

Yield of pure product was 0.15 g (44%) m.p. 208–214° C. ($C_{17}H_{17}N_3O_5$, MW:343.34). Elemental Analysis [%]: Found C, 59.78; H, 4.81; N, 12.10. Calculated C, 59.47; H, 4.99; N, 12.24

E15

0.001 mol (0.22 g) of N-3-nitrophenyl-oxamoyl hydrazide (2e) was dissolved in 5 ml acetic acid and heated at 100° C. with 0.001 mol (0.138 g) of 3,4-dihydroxy-benzaldehyde for 20–25 minutes in the presence of catalytic amount of sodium acetate. The mixture was then cooled and left overnight at room temperature. The separated crystals were filtered off and washed with acetic acid and water.

Yield of pure product was 0.19 g (56%) m.p. >260° C. ($C_{15}H_{12}N_4O_6$, MW:344.286). Elemental Analysis [%]: Found C, 52.08; H, 3.47; N, 16.10. Calculated C, 52.32; H, 3.51; N, 16.27.

E16

0.001 mol (0.22 g) of N-3-nitrophenyl-oxamoyl hydrazide (2e) was dissolved in 5 ml acetic acid and heated at 100° C. with 0.001 mol (0.122 g) of 4-hydroxy-benzaldehyde for 20–25 minutes in the presence of catalytic amount of sodium acetate. The mixture was then cooled and left overnight at room temperature. The separated crystals were filtered off and washed with acetic acid and water. Yield of pure product was 0.19 g (61%) m.p. >260° C. ($C_{15}H_{12}N_4O_5$, MW:328.29). Elemental Analysis [%]: Found C, 54.80; H, 3.59; N, 16.86. Calculated C, 54.88; H, 3.68; N, 17.07.

Group 6 compounds

F10

F10 can be prepared using a two step approach.

a) Preparation of 2-methyl-3-hydroxyethyl quinazolin-4-one 1.37 g (0.01 mol) anthranilic acid was refluxed with 8 ml acetic anhydride for 3 hours. The formed acetic acid was distilled off continuously at atmospheric pressure. After the acetic acid formation was finished the mixture was evaporated in vacuo to dryness. The resulting oil was mixed with 2 ml of ethanolamine and heated at 16 for 3 hours. After the reaction was completed the substance was cooled, mixed with alcohol and left at room temperature overnight. The precipitated crystals were collected by filtration. m.p. 159–60 1.40 g (65%).

Step b 1.08 g (0.005 mol) 2-methyl-3 hydroxyethyl-quinazolin-4-one and 0.69 g 3,4-dihydroxy-benzaldehyde were fused at 160° C. and heated for additional 30 minutes. The resulting substance was dissolved in isopropanol, decolorized by charcoal and left at room temperature overnight. The precipitated crystals were filtered and dried. Yield of pure product was 0.79 g (49%) m.p. 221–223° C. ($C_{18}H_{16}N_2O_4$, MW:324.34) Elemental Analysis [%]: Found C, 66.48 H, 4.86; N, 8.62. Calculated C, 66.66; H, 4.97; N, 8.64.

F11 and F12

1.01 g (5 mmol) of 3,4-dihydro-1,4-oxazine-[3,4-b] quinazolin-6-one were fused with 6 mmol of the corresponding benzaldehyde derivative on an oil bath at a temperature of 100–200° C. After removal of the water of reaction, the resulting mixture was dissolved in ethanol and clarified with charcoal. The solvent was evaporated and the product recrystallized.

For preparation of F11, 3,4-dihydroxybenzaldehyde was used to obtain the product (85% yield) having a melting point of 290–292° C.

For preparation of F12 3-hydroxybenzaldehyde was used to obtain the product (63% yield) having a melting point of 208–214° C.

Group 7 Compounds

Benzoylhydroxyiminoethylacetate

To 10 g benzoyl ethylacetate in 20 ml acetic acid, cooled with ice, was added 3.7 g $NaNO_2$. After 10 minutes 5 ml water was added. After 3 hours 100 ml water was added and the solid filtered to give 7.7 g, 84% yield, mp. 110° C.

NMR $CDCl_3$ $\delta 7.90(2H,m)$, 7.6–7.5(3H,m), 4.30(2H,q,J=7.4 Hz), 1.24(3H,t,J=7.4 Hz).

2-Ethoxycarbonyl-6,7-dimethyl-3-phenyl-quinoxaline 5 g, 22.6 mM benzoylhydroxyiminoethylacetate and 3.1, 22.8 mM, 4,5 dimethyl 1,2-phenylene diamine in 20 ml ethanol and 5 ml HCl were refluxed 6 hours. Workup ($H_2O$, $NaHCO_3$, $CH_2Cl_2$), chromatography and trituration with hexane gave 2 g, 29% yield, white solid, mp. 100° C. NMR CDCl$_3$ Δ 7.96(1H,S), 7.93(1H,S), 7.7(2H,m), 7.5(3H,m) 4.30(2H,q,J=7.0 Hz), 2.53(6H,S), 1.17(3H,t,J =7.0 Hz).

6.7-Dimethylquinoxalin-2-one 2 g, 15 mM, 4.5-dimethyl 1.2-diamino benzene and 1.5 g, 16 mM, glyoxalic acid hydrate in 30 ml ethanol were refluxed 2 hours. Cooling and filtering gave 1.2 g, 46% yield, white solid mp-263° C., Sl. soluble acetone.

NMR DMSO d$_6$ δ60:40 mixture major—8.07 (1H,S), 7.55(1H,S), 7.06(1H,S), 2.30(6H,S). minor—8.02 (1H,S), 7.42(1H,S), 7.28(1H,S), 2.28(6H,S). Remark—reaction of 4.1 g gave 3 g, 57%.

2-Chloro-6,7 Dimethyl Quinoxaline 1.1 g, 6.2 mM, 6,7-dimethylquinoxalin-2-one, 1 ml POCl$_3$ and 1 ml dimethyl aniline in 20 ml toluene were refluxed 2 hours. Workup (NH$_3$, CH$_2$Cl$_2$) and chromatography gave 0.4 g, 33% yield, white solid, mp-86° C. NMR CDCl$_3$ δ8.68(1H,S,H$_2$), 7.85(1H,S), 7.76(1H,S), 2.50(6H, S).

G10

0.4 g (4 mM) phenylene diamine and 0.6 g (4 mM) phenyl glyoxal monohydrate in 20 ml of ethanol, and 10 ml acetic acid was refluxed 3 hours. Workup using 50 ml H$_2$O and 80 ml CH$_2$Cl$_2$ followed by trituration with hexane gave 0.38 g (46% yield) of a white solid having a melting point of 65° C.

NMR CDCl$_3$ δ9.44 (1H,S), 8.1(4H,m), 7.8(2H,m),7.6 (3H,m). MS-206(M+,100%), 179(M—HCN, 25), 152(37), 103(M—Ph—CN, 42), m/e.

G12

To 3 ml DMF and 16 ml PCCl$_3$ was added 2.7 g (10 mM) N-(3,4-dimethoxyphenyl)phenylacetamide. The reaction was heated at 90° C. for 4 hours, decanted on ice, filtered and washed with water to give 2.9 g (96% yield) of a white solid having a melting point of 234° C.

NMR CDCl$_3$): δ8.26 (1H, s h$_4$), 8.0 (1H, s, H$_8$), 7.15 (5H, s Ph), 7.15 (1H, s, h$_5$), 4.13, 4.05 (6H, 2s, OCH$_3$).

MS: 301, 299 (M+, 33%, 100%), 286, 284 (M—CH$_3$, 2%, 6%), 258, 256, (6%, 18%), 220 (9%), 215, 213 (4%, 13%), m/e.

G11

The compound was synthesized, by the procedure used for G12, except that the reactant N-(3,4,5-trimethoxy phenyl)phenylacetamide was substituted. The final product had a melting point of 103° C.

G13

2.4 g (16 mM) phenyl glyoxal hydrate and 2.2 g (16 mM) 3,4-dimethyl-1,2-phenylene diamine in 20 ml ethanol were refluxed for 1.5 hour. Cooling and filtering gave 3.25 g (88% yield) of a white solid having a melting point of 124° C.

NMR CDCl$_3$ δ9.23(1H,S,H$_2$), 8.19(1H,d,J=1.6H$_2$), 8.15 (1H,d,J=1.7H$_2$), 7.90(2H,d,J=9.0 H$_2$), 7.57(3H,m)2.52(6H, S,CH$_3$).

MS-234(M+,100%), 219(M—CH$_3$, 11), 207(M—HCH, 12), 165(M—2HCN—CH$_3$, 2), 131(M-ph-CN,3),. m/e.

G14

7 g of veratrole (51 mM) was added to 19 ml of ice-cooled 70% HNO$_3$. After 0.5 hour in the cold, 10 ml H$_2$SO$_4$ was slowly added in 0.5 hour. The resulting dark suspension was stirred for 3 hours at room temperature and ice and water were added to the suspension to precipitate the product. Filtering, washing with water and drying gave 10.2 g (96% yield) of a yellow solid having a melting point of 120° C. (NMR CDCl$_3$ δ7.35(2H,S), 4.06(6H,S,OCH$_3$)). (Cf: *J. Org. Chem.* 12: 522 (1947), reported m.p. 130° C., and *J. Med. Chem.* 36:331 (1993) reported m.p. 122° C. The compound is sold by Lancaster Co., (reported m.p. 101° C.).

Two grams of 1,2-dinitro-4,5-dimethoxybenzene was hydrogenated over 0.3 g PtO$_2$ for 1 hour, then filtered and evaporated to give 1.5 g of a black solid (Cf. *J. Med. Chem.* 36:331 (93), reported red brown solid, m.p. 151° C.). The black solid was mixed with 1.3 g phenyl glyoxal, 15 ml absolute ethanol and 15 ml of concentrated HCl and refluxed 5 hours. Workup, as for G10, gave a dark solid which was recrystallized from ethanol to give 0.72 g (31% yield) of a white solid having a melting point of 134° C.

NMR CDCl$_3$ δ9.13 (1H,S,H$_2$), 8.16(1H,d,J=1d.6H$_2$), 7.60–7.40(5H,m),4.09(6H,S,OCH$_3$). MS-266(M+,100%), 251(M—CH$_3$,12), 223(M—CH$_3$—CO,13), 196(M—CH$_3$—CO—HCN,5), m/e.

G15

Thiophene-2-glyoxal-bis-thiosemicarbazone (3.4 mM) and 0.6 g (4 mM) o-phenylenediamine in 15 ml acetic acid were refluxed 6 hours. The solvent was removed by distillation in vacuo, and the residue was dissolved in CH$_2$Cl$_2$ and washed with H$_2$O. The organic layer was evaporated in vacuo and the residue was triturated with benzene-hexane to give a white solid (23% yield) mp 104° C.

NMR (CDCl$_3$): δ9.25(1H, s, H$_2$), 8.07, 7.72(4H, m, H$_{5-8}$), 7.85, 7.56, 7.21(3H, m, thiophene).

MS: 212(M$^+$, 100%), 185(M—HCN, 25%), 141(6%), 106(8%), m/e.

G16

2,3-diaminopyridine and phenyl glyoxal were reacted as for G13 to give a white solid (77% yield) having a melting point of 135° C.

NMR CDCl$_3$ δ9.47(1H,S,H$_2$), 9.21 8.50, 7.71 (8 line ABC m, H$_7$,H$_5$,H$_6$), 8.35(2H,m,Ph), 7.60(3H,m).

MS-207(M+,100), 180(H-HCN,8),179(11),104(23),77 (14),m/e. CDCl$_3$ δ7.67(1H, dd), 6.89(dd), 6.62(dd), 4.25, 3.30 (br.S.).

G17

G17 was synthesized in two steps as follows:

a. Synthesis of 2-methoxy-4,5-dinitro phenol 3.3 g 1,2-dimethoxy-4,5-dinitrobenzene in 20 ml of 48% HBr was refluxed for 16 hours. Water was added and the reaction was extracted with CH$_2$Cl$_2$ to give 1.1 g of an orange solid. Chromatography on silica gel, eluting with 2% CH$_3$OH in CH$_2$Cl$_2$ gave 0.42 g (13% yield) of a yellow solid which turned red with KOH.

NMR (CDCl$_3$): δ7.44(1H,s), 7.42(1H,s), 6.30(1H,s), 4.07 (3H,s).

Extraction of the aqueous phase with ethyl acetate gave 2 g of a red oil. Chromatography on silica gel, eluting with 5% CH$_3$OH in CH$_2$Cl$_2$ gave a yellow solid, 0.1 g (3.5% yield) having a melting point of 160° C. with a KOH violet color, corresponding to 1,2 dihydroxy-4,5-dinitrobenzene.

NMR (acetone-d$_6$)δ7.51(2H,s).

b. Reduction and condensation with phenylglyoxal 0.2 g 2-methoxy-4,5-dinitrophenol was hydrogenated on Pd/C in 20 ml ethanol for one hour. The Pd was filtered, 0.3 g phenyl glyoxal was added, and the reaction was refluxed for three hours. Evaporation and chromatography on silica gel, eluting with 1% CH$_3$OH in CH$_2$Cl$_2$ gave a 0.1 g of an orange oil.

NMR (CDCl$_3$): δ8.10, 7.6(7H,m), 3.54(3H,S).

G18

0.56 g (4 mM) 4,5-dimethyl 1,2-diaminobenzene and 0.6 g (4 mM) benzoyl formic acid in 15 ml ethanol were refluxed 5 hours. Cooling and filtering gave 0.8 g (80% yield) of a yellow solid having a melting point of 275° C.

NMR (CDCl$_3$): δ8.38(2H, m), 7.51(3H, m), 7.70(1H, s), 7.06(1H, s) 2.40(3H, s), 2.37(3H, s). Irradiation at 8.38 ppm gave a Singlet at 7.51 ppm.

G19

3,4-diaminotoluene and phenyl glyoxal were reacted as for G13 to give a light brown solid (31% yield) having a melting point of 114° C. NMR CDCl$_3$ δ9.29, 9.26(2S,2:1, H$_2$), 8.2, 8.17(2br.S), 8.07–7.90(3H,m), 7.60(3H,m),2.62 (3H,S).

G20

0.15 g of G14 in 5 ml 48% HBr was refluxed 23 hours. Cooling and filtering gave 95 mg (53% yield) of a green-yellow solid corresponding to the HBr salt of the quinazoline derivative, mp 280° C. HBr was determined by elemental analysis.

NMR (DMSO-d$_6$): δ9.25(1H, s, H$_2$), 8.24(1H, d, J=1.9 Hz), 8.20(1H, d, J=1, 9 Hz), 7.50(3H, m), 7.35(2H, m).

The mother liquid was neutralized with NaHCO$_3$. Extraction with EtAc gave 20 mg (15% yield) of an orange solid, mp 305° C. corresponding to the free base.

NMR (acetone d$_6$): δ9.19(1H s, H$_2$), 8.29(1H, d, J=1.5 Hz), 8.25(1H, d, J=1.5 Hz), 7.6(3H, m), 7.40(2H, m).

MS: 238(M+, 54%), 211(M—HCN, 10%), 154(7%), 108 (1,2-benzoquinone, 100%), m/e.

G21

4-Benzoyl 1,2-phenylene diamine and phenyl glyoxal were reacted as for G13 to give a white solid (69% yield) having a melting point of 133° C.

NMR: CDCl$_3$ δ9.40(1H,S,H$_2$), 8.49(1H,S,H$_5$), 8.27(4H, br,S,H$_{7,8}$H$_2$, '$_6$'), 7.90(2H,d,J=7.6 H$_2$), 7.60(6H,m).

G22

0.47 g (3 mM) 2,3-diaminoaphtalene and 0.47 g phenyl gloxal hydrate in 20 ml ethanol were refluxed for 1.5 hour. Cooling and filtering gave 0.5 g (65% yield) of a light brown solid having a melting point of 163° C.

NMR: CDCl$_3$ δ9.38(1H,S,H$_2$), 8.71,8.67(2H,2d,H$_{5,10}$), 8.25,8.10(4H,AA'BB' m.,H$_{6,9}$), 7.58(5H,m,Ph),

MS-256(H$^+$,100%), 229(H—CN, 12%), 126(71), m/e.

G23

0.6 g, 4 mM, phenyl glyoxal and 0.6 g, 4 mM, 4-nitro phenylene diamine in 15 ml ethanol were refluxed 1.5 hours. Cooling and filtering gave 0.9 g, 90% yield, white solid, mp-203° C.

NMR CDCl$_3$ δ9.49 (1H,S,H$_2$), 9.02(1H, d, J=2.5 Hz, H$_5$), 8.54(1H, dd, J=9.2, 2.5 Hz, H$_7$), 8.27(3H, m, Ph+H$_7$), 7.60 (3H, m, Ph).

G24

1.4 g, 10.3 mM, 4,5-dimethyl 1,2-phenylene diamine and 1.9 g, 10.2 mM, α-chloro 3,4-dihyroxy acetophone in 25 ml ethanol were refluxed 2 hours. Cooling and filtering gave 0.76 g, 18% yield, deep yellow solid, mp. 278° C. as the HCl salt.

G25

2.4 g 2-ethoxycarbonyl-6,7-dimethyl-3-phenyl-quinoxaline and 5 g KOH in 20 ml ethanol and 20 ml H$_2$O were stirred 20 hours at room temperature. Acidification with HCl, filtering and washing with water gave 2.1 g, 96% yield, light-yellow solid, mp. 153° C.

NMR acetone d$_6$ δ7.92(1H,S), 7.90(1H,S), 7.85(2H,m), 7.50(3H,m), 2.56(6H,S).

G27

2-(4-nitrophenyl) 6.7 dimethylquinoxaline 1. 4-nitrophenyl glyoxal 6.60 (40 mmol) 4-nitroacetophenone was dissolved in 30 ml of diozane and 5 g, (45 mmol) selenium dioxide was dissolved in 2.2 ml water and mixed. The mixture was refluxed for 16 hours with continuous stirring. The reaction mixture was passed through an alumina column to remove selenium. The solvent was evaporated in vacuum. The crude product was used in the next step without further purification.

R$_f$ 0.80(EtOAc)
Y:7.00 (85%)
IR(cm$^{-1}$): 1730 (CO), 1520, 1330 (NO$_2$)

2., 2-(4-nitrophenyl) 6,7 dimethylquinoxaline 0.50. g (3 mmol) 4-nitrophenyl glyoxal was dissolved in 20 ml ethanol. 0.34 g (2.5 mml) 1,2 dimethyl 4,5 diaminobenzene was dissolved in ethanol. The reaction mixture was stirred and refluxed for 1 hour. Product crystallized after cooling, and filtrated washing with ethanol then ether.

G28

G28 can be produced using the protocal described for G29 infra, except that 3-bromoaniline is used instead of m-iodoaniline.

G29

150 mg, 0.8 mM, 2-chloro-6,7 dimethyl quinoxaline and 0.8 g, 3.6 mM, m-iodoaniline were heated at 100° C. for 3.5 hours. Chromatography gave 100 mg, 35% yield, yellow solid, mp-185° C.

NMR CDCl$_3$ δ8.33(1H,S), 8.22(1H,m), 7.7(2H,m), 7.40 (1H,m), 7.10(2H,m), 2.45(3H,S), 2.43(3H,S).

G30

210 mg, 1.1 mM, 2-chloro-6,7 dimethyl quinoxaline and 0.8 g, 3.6 mM, p-iodoaniline were heated at 100° C. for 4 hours. Chromatography gave 245 mg, 60% yield, light green solid, mp-228° C.

NMR, CDCl$_3$ δ8.32(1H,S), 7.67(1H,S), 7.64(H,S), 7.68, 7.56(4H,ABq, Jab=9.0 Hz).

Group 8

H10

0.01 mol (1.07 g) of benzylamine and 0.01 mol (1.38 g) of 3,4-dihydroxybenzaldehyde were mixed together in 15 ml of ethanol and refluxed on a waterbath for 15 minutes then 0.01 mol (3.44 g) of 2-(1'-tosyloxyethyl)-quinazolin-4-one and one drop of pyridine were added and the mixture was refluxed for six hours. The resulting solution was evaporated and extracted with a 5% water solution of sodium bicarbonate. The remaining crystals were filtered off, washed with water and recrystallized from isopropanole.

Yield: 3.07 g (77%) M.p.:209–211° C. Formula: $C_{24}H_{21}N_3O_3$
Elemental analysis [%]

| Calculated: | C: 72.17 | H: 5.30 | N: 10.52 |
| Found: | C: 72.12 | H: 5.26 | N: 10.46 |

H11

0.01 mol (1.07 g) of benzylamine and 0.01 mol (1.22 g) of salicylaldehyde were mixed together in 15 ml of ethanol and refluxed on a waterbath for 15 minutes then 0.01 mol (3.44 g) of 2-(1'-tosyloxyethyl)-quinazolin-4-one and one drop of pyridine were added and the mixture was refluxed for six hours. The resulting solution was evaporated and extracted with a 5% water solution of sodium bicarbonate. The remaining crystals were filtered off, washed with water and recrystallized from isopropanole.

Yield: 2.99 g (78%) M.p.:189–192° C. Formula: $C_{24}H_{21}N_3O_2$
Elemental analysis [%]

| Calculated: | C: 75.18 | H: 5.52 | N: 10.96 |
| --- | --- | --- | --- |
| Found: | C: 75.09 | H: 5.49 | N: 10.90 |

H12

0.01 mol (1.07 g) of benzylamine and 0.01 mol (1.22 g) of 3-hydroxybenzaldehyde were mixed together in 15 ml of ethanol and refluxed on a waterbath for 15 minutes then 0.01 mol (3.44 g) of 2-(1'-tosyloxyethyl)-quinazolin-4-one and one drop of pyridine were added and the mixture was refluxed for six hours. The resulting solution was evaporated and extracted with a 5% water solution of sodium bicarbonate. The remaining crystals were filtered off, washed with water and recrystallized from isopropanole.

Yield: 2.72 g (71%) M.p.:184–185° C. Formula: $C_{24}H_{21}N_3O_2$

Elemental analysis [%]

| Calculated: | C: 75.18 | H: 5.52 | N: 10.96 |
| --- | --- | --- | --- |
| Found: | C: 75.02 | H: 5.45 | N: 11.08 |

H13

0.01 mol (1.07 g) of benzylamine and 0.01 mol (1.22 g) of 4-hydroxybenzaldehyde were mixed together in 15 ml of ethanol and refluxed on a waterbath for 15 minutes then 0.01 mol (3.44 g) of 2-(1'-tosyloxyethyl)-quinazolin-4-one and one drop of pyridine were added and the mixture was refluxed for six hours. The resulting solution was evaporated and extracted with a 5% water solution of sodium bicarbonate. The remaining crystals were filtered off, washed with water and recrystallized from isopropanole.

Yield: 3.40 g (89%) M.p.:217–219° C. Formula: $C_{24}H_{21}N_3O_2$

Elemental analysis [%]

| Calculated: | C: 75.18 | H: 5.52 | N: 10.96 |
| --- | --- | --- | --- |
| Found: | C: 75.26 | H: 5.47 | N: 10.88 |

H14

0.01 mol (1.07 g) of benzylamine and 0.01 mol (1.54 g) of 3,4,5-trihydroxybenzaldehyde were mixed together in 15 ml of ethanol and refluxed on a waterbath for 15 minutes then 0.01 mol (3.44 g) of 2-(1'-tosyloxyethyl)-quinazolin-4-one and one drop of pyridine were added and the mixture was refluxed for six hours. The resulting solution was evaporated and extracted with a 5% water solution of sodium bicarbonate. The remaining crystals were filtered off, washed with water and recrystallized from isopropanole.

Yield: 3.36 g (81%) M.p.:223–225° C. Formula: $C_{24}H_{21}N_3O_4$

Elemental analysis [%]

| Calculated: | C: 69.39 | H: 5.10 | N: 10.11 |
| --- | --- | --- | --- |
| Found: | C: 69.51 | H: 5.07 | N: 10.08 |

Group 9

I10

0.3 g (2 mM) 5-formyl indole and 0.4 g (2 mM), of 2-cyano-H-(1-(+) phenylethyl)acetamide in 5 ml ethanol and 2 drops piperidine were refluxed 3 hours. Water and HCl were added and the reaction extracted with ethyl acetate to give viscous oil. Chromatography on silica gel gave 0.42 g (66% yield) of pale-yellow solid having a melting point of 76° C.

MS-315 (M+, 24%), 196 (M—NCH(CH$_3$)C$_6$H$_5$, 22), 195 (25), 188 (21), 173 (24), 168 (13), 149 (57), 145 (100), 134 (92), 116 (53), m/e.

Group 10

J10

230 mg, 1.06 mM, 5-bromo 3,4,dihydroxy benzaldehyde, 76 mg, 0.53 mM, diactonitrile sulphone and 10 mg β-alanine in 10 ml ethanol were refluxed 5 hours. Cooling and filtering gave 220 mg, 76% yield, orange solid, mp>300° C.

NMR acetone d$_6$ δ8.18(2H,S, vinyl), 7.90(2H, d,J=1.6 Hz), 7.78(2H,d,J=1.6 Hz).

J11

2-(3-bromo-4.5-dihydroxyphenyl)-1-cyanomethylsulfonly ethene

A mixture of 500 mg of 5-bromo-3,4-dihydroxybenzaldehyde and 700 mg of sulfonly diacetonitrile in 6 ml of ethanol was refluxed with few drops of piperidine for 4 hours. Ethanol was removed in rotavap and the mixture worked up with ethyl acetate, diluted acid and brine. A portion of the crude was then purified by HPLC on a C-18 column to provide about 50 mg of 2-(3-bromo-4,5-dihydroxyphenyl)-1-cyano-1-cyanomethylsulfonly ethene.

Group 11

6.7-Dimethoxy quinazolin-4-one 7 g 4,5-dimethoxy 2-amino benzoic acid and 8 ml formamide were heated 2 hours at 170° C. Cold water was added and the solid filtered to give 0.9 g, 12% yield, light-brown solid, mp. 308° C.

NMR-DMSO d$_6$ δ8.0(1H,S) 7.43(1H,S), 7.12(1H,S) 3.89 (3H,S), 3.85 (3H,S).

4-Chloro-6,7, Dimethoxy Quinalozine 0.8 g, 6,7-dimethoxy quinazolin-4-one, 1 ml POCl$_3$ and 1 ml dimethyl aniline in 20 ml toluene were refluxed 3.5 hours. Workup and trituration with hexane gave 0.5 g light grey solid, 0.5 g, 57% yield, mp. 188° C.

NMR CDCl$_3$ δ8.88 (1H,S), 7.41(1H,S), 7.36(1H,S), 4.09 (3H,S), 4.08(3H,S).

P10

0.3 g, 1.4 mM, 3.4-dihydroxy 5-bromo benzaldehyde, 0.15 g, 0.7 mM, N-3-cyanomethylcarbonylamino-N-propylcyanoacetamide, and 25 mg β-alanine in 20 ml ethanol were refluxed 3 hours. Cooling and filtering gave 0.24 g, 57% yield, yellow solid, mp 283° C.

P12

Trophene-2-carboxylic acid (3,5-bis-(trifluoromethyl) anilide 0.45 ml (2.9 mmol) of 3,5-bis-(trifluoromethyl) aniline was dissolved in 5 ml of abs pyridine, then cooled to 10° C. 0.12 ml (1.5 mmol) phosphorous trichloride was added with continuous stirring dropwise. After 0.5 hour 0.51 g (4 mmol) thiophene-2-carboxylic acid was added, and stirred for 12 hours at room temperature. Solvent was evaporated in vacuum, 1N HCl was added to the residue and extracted with ethylacetate. The ethylacetate solution was extracted with bicarbonate solution, dried on sodium sulfate, filtrated and evaporated.

Product was triturated with ether, filtrated and dried in vacuum.

m.p.: 145–147° C.
Rf: 0.80 (Hexane-Et)Ac=1:1)
y:0.62 g (80%)
IR(cm$^{-1}$): 3280 (N-H): 1640 (CONH); 1560 (Car); 1130 (C-F)

P13

3 g, 20.1 mM, 3-methyl isoquinoline in 20 ml acetic acid and 5 m 1 30% $H_2O_2$ was heated at 70° C. for 14 hours. Water was added to the cooled solution and bicarbonate to neutrality. Extraction with $CH_2Cl_2$ and trituration with hexane gave 1.9 g, 57% yield, white solid, mp 128° C. (J.O.C., 21:1337(1956), mp-138° C.).

NMR CDCl$_3$ $_\delta$88.86(1H,S), 7.70–7.50(5H,m), 2.64 (3H, S).

P14 a. 0.04 g, 1.8 mM, 4-chloro-6,7, dimethoxy quinalozine and 0.19 g, 2 mM, aniline in 15 ml ethanol were refluxed for 1 hour. Cooling and filtering gave 0.445 g, 78% yield, light yellow solid, mp-268° C., as the HCl salt P14a.

b. free base—0.35 g P14a was treated with $H_2O$—$Na_2CO_3$ and extracted with $CH_2Cl_2$ to give 0.13 g, 42% yield, white solid, mp-241° C.

NMR CDCl$_3$ δ8.86 (1H,S,H$_2$), 7.67(1H,S), 7.63(1H,S), 7.4–7.14(5H,m), 3.96(3H,S), 3.93(3H,S).

P15

1-(2-Chlorophenylmethylene)-3-(3-methoxy-n-propyl)-2,4-thiazolidinedione

A solution of 400 mg of 3-(3-methoxy-n-propyl)-2,4-thiazolidinedione and 260 mg of 2-chlorobenzaldehyde in 4 ml of ethanol with one drop of piperidine was refluxed for 4 hours. The mixture was then worked up with ethyl acetate and water. The crude product was purified on a silica gel column (5 % methanol in dichloromethane) to provide 200 mg of 1-(2-chlorophenylmethylene)-3-(3-methoxy-n-propyl)-2,4-thiazolidinedione. (P15 can also be obtained from Aldrich Chemical.)

P16

0.69 g, 2.5 mM, 5-iodo vaniline, N-3-phenyl-N-propyl cyanoacetamide (prepared as described by Gazit et al., J. Med Chem 34:1896, 1991) and 50 mg β-alanine in 30 ml ethanol were refluxed 5 hours. Evaporation gave an oil which was triturated with benzenehexane and filtered to give a bright yellow solid, 0.82 g, 71% yield, mp. 83° C.
NMR CDCl$_3$ $_\delta$8.12(1H,S), 7.75(1H,d,J=2.0 Hz), 7.68(1H, d,J=2.0 Hz), 7.30–7.10(5H,m), 3.96(3H,S,O,CH$_3$), 3.45(2H, q,J=6.0 Hz), 2.70(2H,t,J=6.0 Hz) 1.95(2H, quin, J=6.0 Hz).

MS-462(M$^+$,53), 357(M—CH$_2$)$_3$Ph,18), 335(M—I,100), 327(M—NH(CH$_2$)$_3$ ph, 31), m/e

P17 a. 0.4 g, 1.8 mM, 4-chloro-6,7, dimethoxy quinalozine and 0.24 g, 2 mM, indoline in 10 ml ethanol were refluxed 2 hours, cooled and filtered to give 0.46 g, 74% yield, yellow solid (P17a), mp. 238° C.

b. free base—0.3 g P17a was treated with $H_2O$—$Na_2CO_3$ and extracted with $CH_2Cl_2$ to give 0.13 g, 48% yield, white solid, mp. 158° C.

NMR CDC$_{13}$ δ8.79 (1H,S,H$_2$), 7.30 (1H,S), 7.28 (1H,S), 7.14–680(4H,m), 4.36(2H,t,J=7.6 Hz), 4.06(3H,S,OCH$_3$), 3.85(3H,S,OCH$_3$), 3.22(2H,t,J=7.6 Hz).

P18

1-Cyano-2-(3-ethoxy-4-hydroxyphenyl)-1-methoxycarbonyl ethene

A mixture of 20 grams of 3-ethoxyl-4-hydroxybenzaldhyde and 13 grams of methyl cyanoacetate in 100 ml of ethanol was refluxed with 1 ml of piperidine for 4 hours. The crude mixture was allowed to cool down to room temperature and, with stirring, water was added until the solid began to form. This mixture was then refrigerated for 4 hours and solids was collected by suction filtration, washed with a cold mixture of ethanol and water (1:2) and suction dried to provide 25 grams of 1-cyano-2-(3-ethoxy-4-hydroxyphenyl)-1-methoxycarbonyl ethene.

19

N-2-chlorophenyl (2-cyano-2-N-morpholinocarbonyl) thioacetamide

A solution of 1.5 gram of N-morpholinyl cyanoacetamide in 20 ml of tetrahydrofuran at 0° C. was added with 680 mg of sodium ethoxide. This mixture was stirred at 0° C. for 1 hour and added with 1.7 grams of 2-chlorophenylisothiocyanate in 5 ml of tetrahydrafuran dropwise. After addition, the mixture was warmed up to room temperature and heated at 50° C. for 6 hours. Upon cooling, all the ethanol was removed and the resulting solid suspended in 10 ml of water. This was then added with 3 ml of 1N sodium hydroxide solution, shaken vigorously and washed with 50 ml of ethyl ether. The aqeous layer was then acidified with 1N hydrochoric acid until pH 1. The solid was then collected by suction filtration. This produced 750 mg of N-2-chlorophenyl (2-cyano-2-N-morpholinylcarbonyl) thioacetamide. (P19 can also be obtained from Ryan Scientific.)

P20

N-2-Chlorophenyl (2-cyano-2-N-3-trifluorophenylaminocarbonyl) thioacetamide

P20 was synthesized using similar conditions as described for P19 but starting with N-3-trifluoromethylphenyl cyanoacetamide. (P20 can also be obtained from Ryan Scientific.)

P21

N-3-methoxyphenyl (2-cyano-2-N-pyrrolidinycarbonyl) thioacetamide

P21 was synthesized using similar conditions as described for P19 but starting with N-pyrrolidinyl cyanoacetamide and 3-methoxylphenylisothiocyanate as the reagents. (P19 can also be obtained from Ryan Scientific.) P22

N-4-trifluoromethlybenzy 3,5-dimethylisoxazole-4-carboxamide

P22 was made using the same conditions as described for N-trifluoromethylphenyl 3,5-dimethylisoxazole-4-carboxamide (A13), but starting with 4-trifluoromethylbenzylamine.

P23

N-trifluoromethlybenzy 3-methylisoxazole-4-carboxamide

A solution of 3 grams of 3-methylisoxazole-4-carboxylic acid and 4.8 grams of 1,3-dicyclohexylcarbodimide in 30 ml of dichloromethane was stirred at room temperature for 30 minutes. This was then added with 8 ml of 4-trifluoromethylbenzylamine dropwise and the mixture stirred at room temperature overnight. The mixture was then diluted in ethyl acetate (100 ml) and worked up with diluted hydrochloride solution, saturated sodium bicarbonate and sodium chloride solution, dried over sodium sulfate, filtered and concentrated. The crude was then crystallized with ethanol and water to provide 1.5 grams of N-trifluoromethlybenzyl 3-methylisoxazole-4-carboxamide.

P24

1-trifluorometnlybenzylaminocarbonly-1-cyano-2-hydroxy propene

A solution of 500 mg of N-trifluormethlybenzyl 3-methylisoxazole-4-carboxamide in 5 ml of ethanol was added to 300 mg of 1,8-diazabicyclo [5.4.0]undec-7-ene. The mixture was then stirred at room temperature for 1 hour and acidified with 2 ml of 2N hydrochloride solution. The solid was collected by filtration to provide 350 mg of 1-trifluoromethylbenzylaminocarbonyl-1-cyano-2-hydroxy propene.

P25

0.42 g, 3 mM, 3,4-dihydroxy benzaldehyde, 0.6 g, 3.1 mM, N-4-flurobenzylcyanoacetamide and 2.0 mg β-alanine were refluxed 5 hours. Concentration and filtration gave 0.89 g, 95% yield, yellow solid, mp-212° C., NMR acetone $d_6$ δ8.10 (1H,S, Vinyl), 7.68(1H,d,J=2.3 Hz, $H_2$), 7.40(3H,m, $H_6,H_2,H_6$), 7.09(2H,t,J=8.8 Hz, $H_{3',5'}$) 6.98(1H,d,J=8.3 Hz,$H_5$), 4.56(2H,br,S).

MS—312($M^+$, 46%), 311(30), 295(H—OH,35), 161(17), 124(NHCH$_4$C$_6$, H$_4$F, 100%), 109 (CH$_2$C$_6$H$_4$F,73)-m/e.

Other embodiments are within the following claims.

What is claimed is:

1. A method of evaluating the susceptibility of a cancer to growth inhibition by a compound comprising the steps of:

(a) culturing cells of said cancer in medium containing PDGF;

(b) culturing cells of said cancer in medium containing PDGF and said compound; and (c) measuring and comparing the growth of said cells in (a) and (b), wherein said compound is selected from the group consisting of:
 i) a compound of Formula I:

(Formula I)

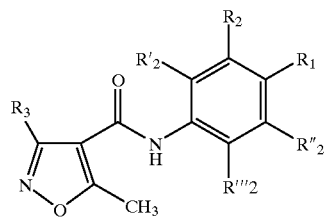

wherein
 $R_1$, $R_2$, $R'_2$, $R''_2$, and $R'''_2$ are independently selected from the group consisting of hydrogen, halogen, trihalomethyl, and $NO_2$; and
 $R_3$ is selected from the group consisting of hydrogen, carboxy, alkoxy, and carbalkoxy;

ii) a compound of Formula II:

(Formula II)

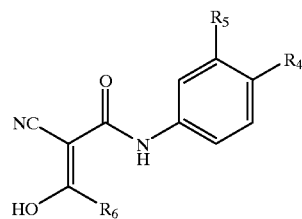

wherein
 $R_4$ and $R_5$ are independently selected from the group consisting of halogen, hydrogen, trihalomethyl, and $NO_2$; and
 $R_6$ is selected from the group consisting of aryl, alkyl, alkenyl and alkynyl;

iii) a compound of Formula III:

(Formula III)

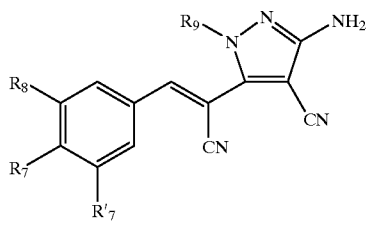

wherein
 $R_7$, $R'_7$, and $R_8$ are independently selected from the group consisting of halogen, OH, hydrogen, alkoxy, SH, $NH_2$, and $C(CH_3)_3$; and
 $R_9$ is aryl or hydrogen;

iv) a compound of Formula IV:

(Formula IV)

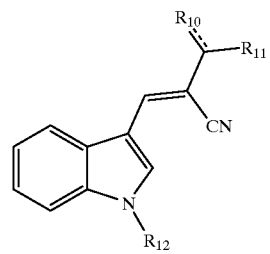

wherein
 $R_{10}$ is selected from the group consisting of =S, =O, SH, OH, and $NH_2$; $R_{11}$ is selected from the group consisting of SH, OH, $NH_2$, =C(CN)$_2$ and aryl; or $R_{10}$ and $R_{11}$ taken together are aryl; and
 $R_{12}$ is selected from the group consisting of hydrogen, aryl, alkyl, alkenyl, and alkynyl;

v) a compound of Formula V:

(Formula V)

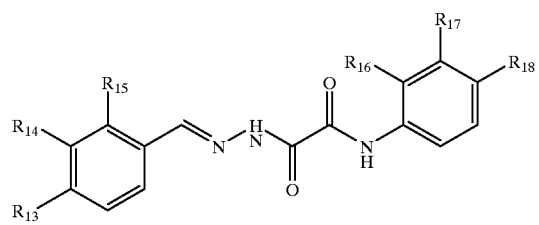

wherein $R_{13}$, $R_{14}$, $R_{15}$, $R_{16}$, $R_{17}$, and $R_{18}$ are independently selected from the group consisting of hydrogen, halogen, alkoxy, OH, amino, alkylamino, and SH;

vi) a compound of Formula VI:

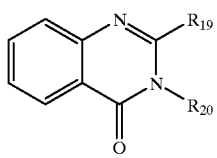
(Formula VI)

wherein $R_{19}$ is selected from the group consisting of aryl, alkyl, alkenyl and alkynyl; and $R_{20}$ is alkyl; or $R_{19}$ and $R_{20}$ are together aryl;

vii) a compound of Formula VII:

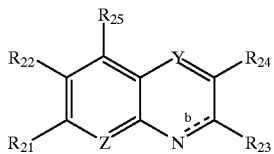
(Formula VII)

wherein b is an optional pi bond; Y and Z are independently carbon or nitrogen;

$R_{21}$ and $R_{22}$ are independently selected from the group consisting of hydrogen, halogen, OH, SH, $NH_2$, $NO_2$, alkyl, alkenyl, alkynyl, alkoxy, benzoyl, COOH, and carbalkoxy; or $R_{21}$ and $R_{22}$ are together aryl;

$R_{23}$ is selected from the group consisting of hydrogen, halogen, =O, OH, SH, $NH_2$, alkoxy, COOH, and aryl;

$R_{24}$ is H or aryl; and $R_{25}$ is selected from the group consisting of hydrogen, halogen, =S, or =O, wherein if $R_{25}$ is =O or =S then b is present as a bond;

provided that if b is not a bond, the adjacent nitrogen optionally has a substituent selected from the group consisting of hydrogen, alkyl, alkyleneamino, alkyleneaminoalkly, and alkylenecyano;

viii) a compound of Formula VIII:

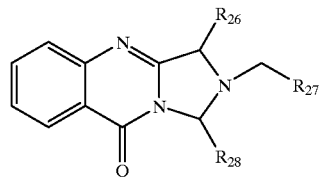
(Formula VIII)

wherein $R_{26}$ and $R_{28}$ are independently selected from the group consisting of alkyl, aryl, alkenyl, and alkynyl; and $R_{27}$ is aryl;

ix) a compound of Formula IX:

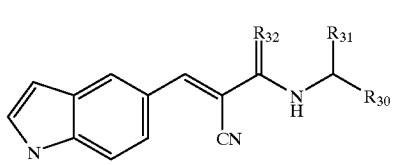
(Formula IX)

wherein $R_{30}$ is selected from the group consisting of alkyl, alkenyl, and $R_{31}$ is aryl; and $R_{32}$ is either O or S;

x) a compound of Formula X:

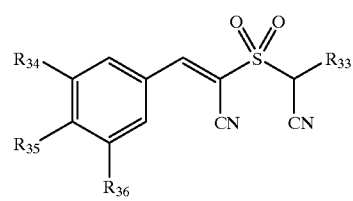
(Formula X)

wherein $R_{33}$ is alkyl or aryl;

$R_{34}$, $R_{35}$, and $R_{36}$ are independently selected from the group consisting of halogen, OH, hydrogen, alkoxy, SH, $NH_2$, and $C(CH_3)_3$; and xi) a compound of any one Formula XI(a)–Formula XI(o):

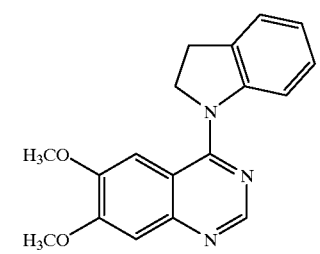
(Formula XI(a))

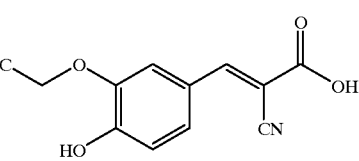
(Formula XI(b))

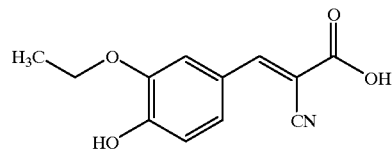
(Formula XI(c))

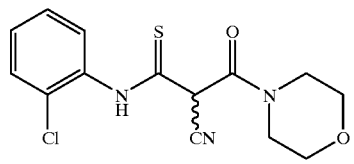
(Formula XI(d))

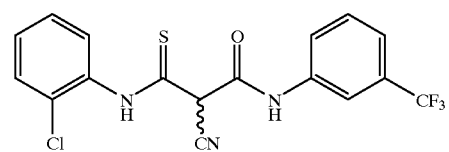

(Formula XI(e))

(Formula XI(f))

(Formula XI(g))

(Formula XI(h))

(Formula XI(i))

(Formula XI(j))

(Formula XI(k))

(Formula XI(l))

(Formula XI(m))

(Formula XI(n))

(Formula XI(o))

or a pharmaceutically acceptable salt of said compound.

2. The method of claim 1, wherein said cells are from a cancer selected from the group consisting of intra-axial brain cancer, ovarian cancer, colon cancer, prostate cancer, lung cancer, Kaposi's sarcoma, and melanoma.

3. The method of claim 2, wherein said cancer is intra-axial brain cancer.

4. The method of claim 2, wherein said cancer is ovarian cancer.

5. The method of claim 2, wherein said cancer is prostate cancer.

6. The method of claim 1, wherein said measuring of cell growth is by a colorimetic assay.

7. The method of claim 1, wherein said measuring of cell growth is by a radioactivity incorporation assay.

8. A method of evaluating the susceptibility of a cancer to growth inhibition by a compound comprising the steps of:
   (a) culturing cells of said disorder in medium containing PDGF;
   (b) culturing cells of said disorder in medium containing PDGF and said compound; and
   (c) measuring and comparing the growth of said cells in (a) and (b), wherein said compound is selected from the group consisting of:

(i) a compound of Formula I:

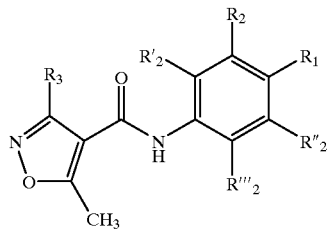

(Formula I)

wherein
R$_1$, R$_2$, R'$_2$, R'''$_2$ are independently selected from the group consisting of hydrogen, halogen, trihalomethyl, and NO$_2$; and
R$_3$ is selected from the group consisting of hydrogen, carboxy, alkoxy, and carbalkoxy;

(ii) a compound of Formula II:

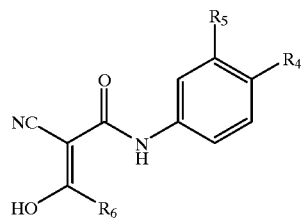

(Formula II)

wherein
R$_4$ and R$_5$ are independently selected from the group consisting halogen, hydrogen, trihalomethyl, and NO$_2$; and
R6 is selected from the group consisting of aryl, alkyl, alkenyl and alkynyl;

(iii) a compound of Formula III:

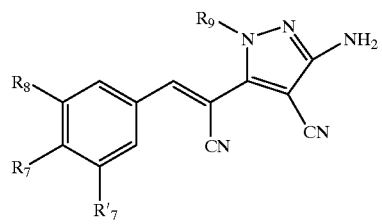

(Formula III)

wherein
R$_7$, R'$_7$ and R$_8$ are independently selected from the group consisting halogen, OH, hydrogen, alkoxy, SH, NH$_2$ and C(CH$_3$)$_3$; and
R$_9$ is aryl or hydrogen;

(iv) a compound of Formula IV:

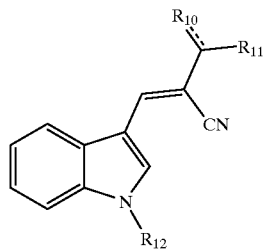

(Formula IV)

wherein
R$_{10}$ is selected from the group consisting of =S, =O, SH, OH, and NH$_2$;
R$_3$, is selected from the group consisting of SH, OH, NH$_2$, =C(CN)$_2$ and aryl; or R$_9$ and
R$_{11}$, taken together are aryl; and
R$_{12}$ is selected from the group consisting of hydrogen, aryl, alkyl, alkenyl, and alkynyl;

(v) a compound of Formula V:

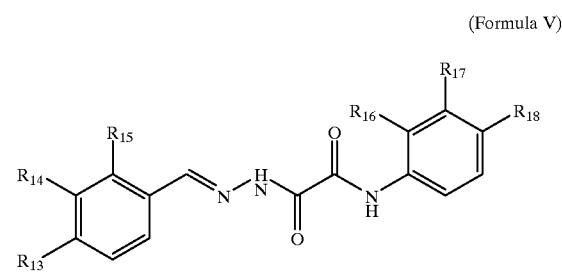

(Formula V)

wherein
R$_{13}$, R'$_{14}$, R$_{15}$, R$_{16}$, R$_{17}$ and R$_{18}$ are independently selected from the group consisting hydrogen, halogen, alkoxy, OH, amino, alkylamino, and SH;

(vi) a compound of Formula VI:

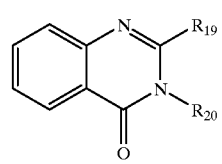

(Formula VI)

wherein
R$_{19}$ is selected from the group consisting of aryl, alkyl alkenyl and alkynyl;
and R$_{20}$ is alkyl; or R$_{19}$ and R$_{20}$ are together aryl;

(vii) a compound of Formula VII:

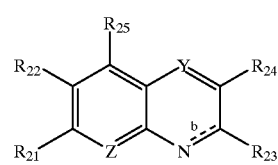

(Formula VII)

wherein b is an optional pi bond; Y and Z are indepndndtly carbon or nitrogen;

R$_{21}$, and R$_{22}$ are independently selected from the group consisting of hydrogen, halogen, OH, SH, NH$_2$, NO$_2$, alkyl, alkenyl, alkynyl, alkoxy, benzoyl, COOH, and carbalkoxy; or R$_{21}$ and R$_{22}$ are together aryl;

R$_{23}$ is selected from the group consisting of hydrogen, halogen, =O, OH, SH, NH$_2$, NO$_2$, alkoxy, alkyl, COOH, and aryl;

R$_{24}$ is H or aryl; and

R$_{25}$ is selected from the group consisting of hydrogen, halogen, =S, or =O, wherein if R$_{25}$ is =O or =S then b is present as a bond;

provided that if b is not a bond, the adjacent nitrogen optionaly has a substituent selected from the group consisting hydrogen, alkyl, alkyleneamino, alkyleneaminoalkyl, and alkylenecyano;

(viii) a compound of Formula VIII:

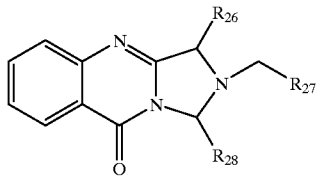

(Formula VIII)

wherein
R$_{26}$ and R$_{28}$ are independently selected from the group consisting of alkyl, aryl, alkenyl, and alkynyl; and R$_{27}$ is aryl;

(ix) a compound of Formula IX:

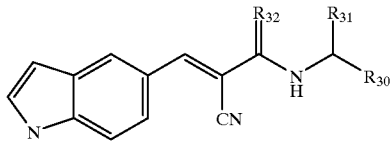

(Formula IX)

wherein
R$_{30}$ is selected from the group consisting of alkyl, alkenyl, and alkynyl;

R$_{31}$ is aryl; and

R$_{32}$ is either O or S;

(x) a compound of Formula X:

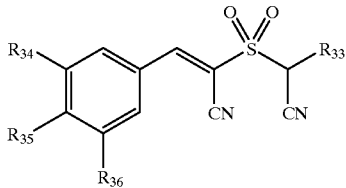

(Formula X)

wherein
R$_{33}$ is alkyl or aryl;

R$_{34}$, R$_{35}$, and R$_{36}$ are independently selected from the group consisting of halogen, OH, hydrogen, alkoxy, SH, NH$_2$, and C(CH$_3$)$_3$; and (xi) a compound of any one Formula XI(a)–Formula XI(o):

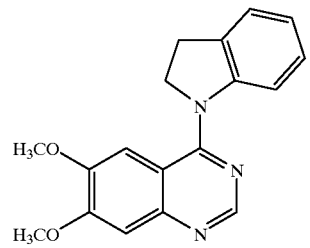

(Formula XI(a))

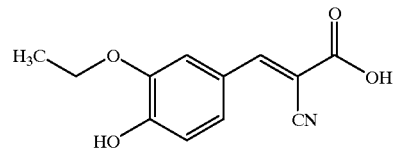

(Formula XI(b))

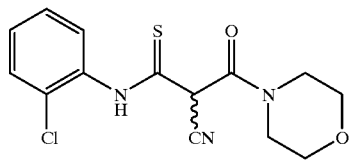

(Formula XI(c))

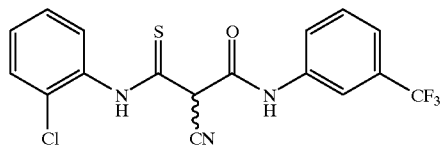

(Formula XI(d))

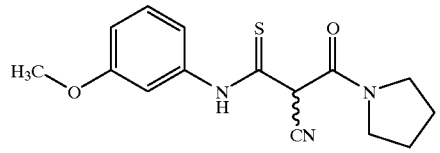

(Formula XI(e))

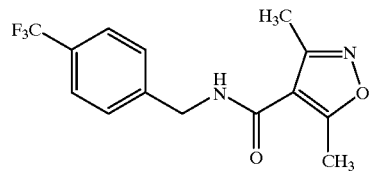

(Formula XI(f))

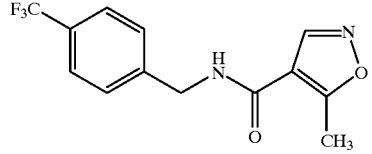

(Formula XI(g))

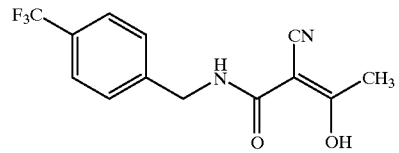

(Formula XI(h))

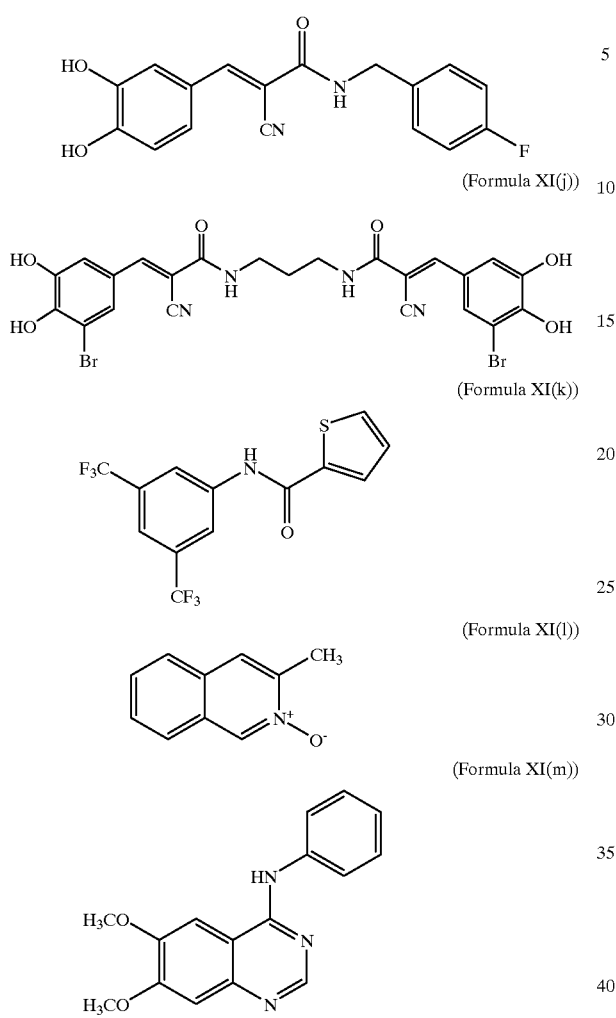

or a pharmaceutically acceptable salt of said compound.

9. The method of claim 8, wherein said disorder is a blood vessel proliferation disorder.

10. The method of claim 9, wherein said blood vessel proliferative disorder is atherosclerosis.

11. The method of claim 8, wherein said disorder is a fibrotic disorder.

12. The method of claim 11, wherein said fibrotic disorder is a hepatic fibrotic disorder.

13. The method of claim 11, wherein said fibrotic disorder is a mesangial cell proliferative disorder.

14. The method of claim 8, wherein said measuring of cell growth is by a colorimetic assay.

15. The method of claim 8, wherein said measuring of cell growth is by a radioactivity incorporation assay.

* * * * *

UNITED STATES PATENT AND TRADEMARK OFFICE
CERTIFICATE OF CORRECTION

PATENT NO.    : 6,331,555 B1                                        Page 1 of 1
DATED         : December 18, 2001
INVENTOR(S)   : Klaus Peter Hirth et al.

It is certified that error appears in the above-identified patent and that said Letters Patent is hereby corrected as shown below:

<u>Title page,</u>
Item [75], replace with the following
-- [75] Inventors: Klaus P. Hirth, San Francisco; Elaina Mann, Alameda; Laura K. Shawyer, San Francisco, all of CA (US); Axel Ullrich, Munchen (DE); Gyorgi Keri, Budapest (HU); Istvan Szekely, Dunakeszi (HU); Tamas Bajor, Budapest (HU); Janis Haimichael, Budapest (HU); Laszlo Orfi, Budapest (HU); Alex Levitzki; Aviv Gazit, both of Jerusalem (IL); Peng Cho Tang, Moraga, CA (US); Reiner Lammers, Munchen (DE). --

Signed and Sealed this

Twenty-fourth Day of September, 2002

*Attest:*

*Attesting Officer*

JAMES E. ROGAN
*Director of the United States Patent and Trademark Office*